US006515103B1

(12) United States Patent
Abogadie et al.

(10) Patent No.: US 6,515,103 B1
(45) Date of Patent: Feb. 4, 2003

(54) CONANTOKINS

(75) Inventors: Fe C. Abogadie, London (GB); Lourdes J. Cruz, Salt Lake City, UT (US); Baldomero M. Olivera, Salt Lake City, UT (US); Craig Walker, Salt Lake City, UT (US); Clark Colledge, Alpine, UT (US); David R. Hillyard, Salt Lake City, UT (US); Elsie Jimenez, Qyezan (PH); Richard T. Layer, Salt Lake City, UT (US); Li-Ming Zhou, Salt Lake City, UT (US); Gregory S. Shen, Salt Lake City, UT (US); R. Tyler McCabe, Salt Lake City, UT (US); Jean E. Rivier, La Jolla, CA (US)

(73) Assignees: University of Utah Research Foundation, Salt Lake City, UT (US); Cognetix, Inc., Salt Lake City, UT (US); Salk Institute, LaJolla, CA (US)

( * ) Notice: Subject to any disclaimer, the term of this patent is extended or adjusted under 35 U.S.C. 154(b) by 0 days.

(21) Appl. No.: 09/142,080

(22) PCT Filed: Jul. 21, 1997

(86) PCT No.: PCT/US97/12618
§ 371 (c)(1), (2), (4) Date: May 15, 2000

(87) PCT Pub. No.: WO98/03541
PCT Pub. Date: Jan. 29, 1998

Related U.S. Application Data

(63) Continuation-in-part of application No. 08/684,742, filed on Jul. 22, 1996, now abandoned.

(51) Int. Cl.[7] ............................................. A61K 38/00
(52) U.S. Cl. .................... 530/326; 530/300; 530/327; 514/13; 514/14; 514/15; 514/21
(58) Field of Search ............................. 530/327, 300, 530/326; 514/13, 21, 14, 15

(56) References Cited

U.S. PATENT DOCUMENTS

| | | |
|---|---|---|
| 4,806,543 A | 2/1989 | Choi |
| 4,959,493 A | 9/1990 | Ohfume et al. |
| 5,049,555 A | 9/1991 | Rzeszotarski et al. |
| 5,051,413 A | 9/1991 | Angst et al. |
| 5,061,721 A | 10/1991 | Cordl et al. |
| 5,086,072 A | 2/1992 | Trullas et al. |
| 5,428,069 A | 6/1995 | Skolnick et al. |
| 5,432,155 A | 7/1995 | Olivera et al. |
| 5,523,323 A | 6/1996 | Maccecchini |
| 5,830,998 A | 11/1998 | Maccecchini |
| 5,854,217 A | 12/1998 | Maccecchini |

FOREIGN PATENT DOCUMENTS

| | | |
|---|---|---|
| EP | 0514023 | 11/1992 |
| WO | 9101729 | 2/1991 |
| WO | 9304688 | 3/1993 |
| WO | 9407914 | 4/1994 |
| WO | 9611698 | 4/1996 |

OTHER PUBLICATIONS

Barinaga, M., "Science Digests the Secrets of Voracious Killer Snails", *Science* Jul. 20, 1990; 249:250–251.

Benke, T.A., et al., "N–Methyl–D–aspartate receptors are clustered and immobilized on dendrites of living cortical neurons", *Proc. Natl. Acad. Sci. USA* Aug. 1993; 90:7819–7823.

Chandler, P., et al., "Polyamine–like Actions of Peptides Derived from Conantokin–G, an N–Methyl–D–aspartate (NMDA) Antagonist", *J. of Biol. Chem.* Aug. 15, 1993; 268(23):17173–17178.

Croucher, M.J., et al., "Anticonvulsant Action of Excitatory Amino Acid Antagonists", *Science* May 21, 1982; 216:899–901.

Dichter, M.A. and Choi, D.W., "Excitatory Amino Acid Neurotransmitters and Excitotoxins", *Curr. Neurol.* 1989; 9:1–26.

Franklin, P.H. and Murray, T.F., "High Affinity [$^3$H] Dextrorphan Binding in Rat Brain Is Localized to a Noncompetitive Antagonist Site of the Activated N–Methyl–D–aspartate Receptor–Cation Channel", *Mol. Pharmacol.* Jan. 1992: 41:134–146.

Haack, J.A., et al., "γ–Carboxyglutamate Containing Peptide with N–Methyl–D–Aspartate Antagonist Activity", *J. Biol. Chem.* Apr. 15, 1990; 265(11):6025–6029.

Haack, J.A., et al., "Conantokin–G antagonism of the NMDA receptor subtype expressed in cultured cerebellar granule cells", *Neurosci. Lett.* 1993; 163:63–66.

Hammerland, L.G., et al., "Conantokin–G selectively inhibits N–methyl–D–aspartate–induced currents in Xenopus oocytes injected with mouse brain mRNA", *Eur. J. Pharmacol.—Molecular Pharmacology Section* (1992); 226:239–244.

Hernandez, J–F, et al., "Synthesis, Characterization and Biological Activity of Conantokin G Analogs", 1990 UCLA Symposia Conference on Biochemical & Bimedical Engineering Synthetic Peptides: Approaches to Biological Problem; Feb. 27–Mar. 4, 1990; Frisco, Colorado (21 pages).

Johnson, R.L. and Koerner, J.F., "Excitatory Amino Acid Neurotransmission", *J. Medicinal Chemistry* Nov. 1988; 31(11):2057–2066.

(List continued on next page.)

*Primary Examiner*—Jeffrey Fredman
(74) *Attorney, Agent, or Firm*—Rothwell, Figg, Ernst & Manbeck

(57) ABSTRACT

The present invention is directed to conantokin peptides, conantokin peptide derivatives and conantokin peptide chimeras, referred to collectively as conantokins, having 10–30 amino acids, including preferably two or more γ-carboxyglutamic acid residues. The conantokins are useful for the treatment of neurologic and psychiatric disorders, such as anticonvulsant agents, neuroprotective agents or analgesic agents.

17 Claims, 19 Drawing Sheets

OTHER PUBLICATIONS

Jones, A.W., et al., "Structure–Activity Relations of Dipeptide Antagonists of Excitatory Amino Acids", *Neuroscience* 1984; 13(2):573–581.

Kyle, D.J., "NMDA receptors: heterogeneity and agonism", 121–161 and Figs. 1.4, 6.10–6.19, 7.4, 8.5, 10.6, 10.9, 11.3 and 15.4.

Lehmann, J., et al., "Glutamate and Glycine Co–Activate While Polyamines Merely Modulate the NMDA Receptor Complex", *Prog. Neuro–Psychopharmacol. & Biol. Psychiat.* 1991; 15:183–190.

Lipton, S.A. and Rosenberg, P.A., "Excitory Amino Acids as a Final Common Pathway for Neurologic Disorders", *N. Engl. J. Med.* 1994; 330(9):613–622.

Mayer, M.L. and Miller, R.J., "Excitatory amino acid receptors, second messengers and regulation of intracellular $Ca^{2+}$ in mammalian neurons", *TiPS* Jun. 1990; 11:254–260.

McIntosh, J.M., et al., "γ–Carboxyglutamate in a Neuroactive Toxin", *J. of Biol. Chem.* Dec. 10, 1984; 259(23):14343–14346.

Mena, E.E., et al., "Conantokin–G: a novel peptide antagonist to the N–methyl–D–aspartic acid (NMDA) receptor", *Neurosci. Lett.* 1990; 118:241–244.

Moudy, A.M., et al., "Rapid Desensitization Determines the Pharmacology of Glutamate Neurotoxicity", *Neuropharmacology* Aug. 1994; 33(8):953–962.

Myers, R.A., et al., "Conus Peptides as Chemical Probes for Receptors and Ion Channels", *Chem. Rev.* 1993; 93:1923–1936.

Nishiuchi, Y., et al., "Synthesis of γ–carboxyglutamic acid–containing peptides by the Boc strategy", *Int. J. Peptide Protein Res.* 1993; 42:533–538.

Olivera, B.M., et al., "Diversity of Conus Neuropeptides", *Science* Jul. 20, 1990; 249:257–263.

Olivera, B.M., et al., "A Sleep–Inducing Peptide From *Conus geographus* Venom", *Toxicon* 1995; 23(2):277–282.

Porter, R.H.P., et al., "Modulation of [$^3$H]3 –((±)–2–carboxypiperazin–4–yl)propyl–1–phosphonic acid ([$^3$H]CPP) binding by ligands acting at the glycine and the polyamine sites of the rat brain NMDA receptor complex", *Eur. J. Pharmacol.—Molecular Pharmacology Section* 1992: 227:83–88.

Ransom, R.W., and Stec, N.L., "Cooperative Modulation of [$^3$H]MK–801 Binding to the N–Methyl–D–Aspartate Receptor–Ion Channel Complex by L–Glutamate, Glycine, and Polyamines", *J. Neurochem.* 1988; 51(3)830–836.

Rao, T.S., et al., "Polyamines Modulate Events Mediated by the N–Methyl–D–Aspartate (NMDA) Receptor Complex Through an Ifenprodil–Insensitive Pathway: In Vivo Measurements of Cyclic GMP in the Cerebellum", *Neuropharmacology* 1991; 30(6):567–573.

Reynolds, I.J. and Miller, R.J., "Ifenprodil is a Novel Type of N–Methyl–D–aspartate Receptor Antagonist: Interaction with Polyamines", *Mol. Pharmacol.* 36:758–765.

Sacaan, A.I. and Johnson, K.M., "Spermidine Reverses Arcaine's Inhibition of N–Methyl–D–Aspartate–Induced Hippocampal[$^3$H]Norepinephrine Release", *J. Pharmacology and Experimental Therapeutics* 1990; 255(3):1060–1063.

Shatz, C.J., "Dividing Up the Neocortex", *Science* Oct. 9, 1992; 258:237–238.

Simon, R.P., et al., "Blockade of N–Methyl–D–Aspartate Receptors May Protect Against Ischemic Damage in the Brain", *Science* Nov. 16, 1984; 226:850–852.

Skolnick, P., et al., "Conantokin–G and its Analogs: Novel Probes of the NMDA Receptor–Associated Polyamine Site", In Palfreyman, M.G. et al. (eds): *Direct and Allosteric Control of Glutamate Receptors*. CRC Press, Boca Raton, Florida, 1994. pp. 155–165.

Skolnick, P., et al., "Noncompetitive Inhibition of N–Methyl–D–Aspartate by Conantokin–G: Evidence for an Allosteric Interaction at Polyamine Sites", *J. Neurochem.* 1992; 59(4):1516–1521.

Trullas, R. and Skolnick, P., "Functional antagonists at the NMDA receptor complex exhibit antidepressant actions", *Eur. J. Pharmacol.* 1990; 185:1–10.

Von Lubitz, D.K.J.E., et al., "A novel treatment of global cerebral ischaemia with a glycine partial agonist", *Eur. J. Pharmacol.* Aug. 14, 1992; 219(1):153–158.

Watkins, J.C., et al., "Structure–activity relationships in the development of excitatory amino acid receptor agonists and competitive antagonists", *TiPS* Jan. 1990; 11:25–33.

Whitten, J.P., et al., "Modeling of Competitive Phosphono Amino Acid NMDA Receptor Antagonists", *J. Medicinal Chemistry* 1992; 35(9):1509–1514.

Witkin, J.M. and Tortella, F.C., "Modulators of N–Methyl–D–Aspartate Protect Against Diazepam–or Phenobarbital–Resistant Cocaine Convulsions", *Life Sciences* 1991; 48(11):51–56.

Zhou, L–M, et al., "Synthesis of N,N–3 –Substituted Piperazine and Homopiperazine Derivatives with Polyamine–Like Actions at N–Methyl–D–aspartate Receptors", *J. Med. Chem.* 1995; 38:4891–4896.

Zhou, L–M, et al., "Synthetic Analogues of Conantokin–G: NMDA Antagonists Acting Through a Novel Polyamine–Coupled Site", *J. Neurochem.* 1996; 66(2):620–628.

Sopanen et al, "Uptake of small peptides by the scutellum of germinating Barley", Febs Lett. 79(1):4–7. Jul. 1977.*

* cited by examiner

SEQUENCE LISTING (1) GENERAL INFORMATION:

(iii) NUMBER OF SEQUENCES: 71

(2) INFORMATION FOR SEQ ID NO: 1:

(i) SEQUENCE CHARACTERISTICS:
      (A) LENGTH: 17 amino acids
      (B) TYPE: amino acid
      (C) STRANDEDNESS: <Unknown>
      (D) TOPOLOGY: linear (ii) MOLECULE TYPE: peptide (vi) ORIGINAL SOURCE:
      (A) ORGANISM: Conus geographus (ix) FEATURE:
      (A) NAME/KEY: Modified-site
      (B) LOCATION: 3..14
      (D) OTHER INFORMATION: /note= "Xaa at residues 3 and 4 is
         gamma-carboxyglutamic acid; Xaa at residues 7, 10 and 14
         may be any amino acid but is preferably
         gamma-carboxyglutamic acid"

(xi) SEQUENCE DESCRIPTION: SEQ ID NO: 1:

Gly Glu Xaa Xaa Leu Gln Xaa Asn Gln Xaa Leu Ile Arg Xaa Lys Ser
1            5                  10                15

Asn (2) INFORMATION FOR SEQ ID NO: 2:

(i) SEQUENCE CHARACTERISTICS:
        (A) LENGTH: 21 amino acids
        (B) TYPE: amino acid
        (C) STRANDEDNESS: <Unknown>
        (D) TOPOLOGY: linear (ii) MOLECULE TYPE: peptide (vi) ORIGINAL SOURCE:
        (A) ORGANISM: Conus tulipa (ix) FEATURE:
        (A) NAME/KEY: Modified-site
        (B) LOCATION: 3..13
        (D) OTHER INFORMATION: /note= "Xaa at residues 3 and 4 is
            gamma-carboxyglutamic acid; Xaa at reisdues 10 and 14
            may be any amino acid but is preferably
            gamma-carboxyglutamic acid"

(xi) SEQUENCE DESCRIPTION: SEQ ID NO: 2:

Gly Glu Xaa Xaa Tyr Gln Lys Met Leu Xaa Asn Leu Arg Xaa Ala Glu
1               5                   10                  15

Val Lys Lys Asn Ala
            20

(2) INFORMATION FOR SEQ ID NO: 3:

(i) SEQUENCE CHARACTERISTICS:
        (A) LENGTH: 19 amino acids
        (B) TYPE: amino acid
        (C) STRANDEDNESS: <Unknown>
        (D) TOPOLOGY: linear (ii) MOLECULE TYPE: peptide (vi) ORIGINAL SOURCE:
        (A) ORGANISM: Conus lynceus (ix) FEATURE:
        (A) NAME/KEY: Modified-site
        (B) LOCATION: 3..15
        (D) OTHER INFORMATION: /note= "Xaa at residues 3 and 4 is
            gamma-carboxyglutamic acid; Xaa at residues 11 and 15 may
            be any amino acid, but is preferably
            gamma-carboxyglutamic acid"

(xi) SEQUENCE DESCRIPTION: SEQ ID NO: 3:

Gly Glu Xaa Xaa Val Ala Lys Met Ala Ala Xaa Leu Ala Arg Xaa Asp
1               5                   10                  15

Ala Val Asn (2) INFORMATION FOR SEQ ID NO: 4:

(i) SEQUENCE CHARACTERISTICS:
        (A) LENGTH: 27 amino acids
        (B) TYPE: amino acid
        (C) STRANDEDNESS: <Unknown>
        (D) TOPOLOGY: linear (ii) MOLECULE TYPE: peptide (vi) ORIGINAL SOURCE:
        (A) ORGANISM: Conus radiatus (ix) FEATURE:
        (A) NAME/KEY: Modified-site
        (B) LOCATION: 3..15
        (D) OTHER INFORMATION: /note= "Xaa at residues 3 and 4 is
            gamma-carboxyglutamic acid; Xaa at residues 11 and 15 may
            be any amino acid, but is preferably gamma-carboxyglutamic
            acid"

(ix) FEATURE:
            (A) NAME/KEY: Disulfide-bond
            (B) LOCATION: 21..25

(xi) SEQUENCE DESCRIPTION: SEQ ID NO: 4:

Gly Glu Xaa Xaa Val Ala Lys Met Ala Ala Xaa Leu Ala Arg Xaa Asn
1               5                   10                  15

Ile Ala Lys Gly Cys Lys Val Asn Cys Tyr Pro
            20                  25

(2) INFORMATION FOR SEQ ID NO: 5:

(i) SEQUENCE CHARACTERISTICS:
            (A) LENGTH: 24 amino acids
            (B) TYPE: amino acid
            (C) STRANDEDNESS: <Unknown>
            (D) TOPOLOGY: linear (ii) MOLECULE TYPE: peptide (vi) ORIGINAL SOURCE:
            (A) ORGANISM: Conus sulcatus (ix) FEATURE:
            (A) NAME/KEY: Modified-site
            (B) LOCATION: 3..14
            (D) OTHER INFORMATION: /note= "Xaa at residues 3 and 4 is
                gamma-carboxyglutamic acid; Xaa at residues 10 and 14 may
                be any amino acid, but is preferably gamma-carboxyglutamic
                acid"

(xi) SEQUENCE DESCRIPTION: SEQ ID NO: 5:

Gly Asp Xaa Xaa Tyr Ser Lys Phe Ile Xaa Arg Glu Arg Xaa Ala Gly
1               5                   10                  15

Arg Leu Asp Leu Ser Lys Phe Pro
            20

(2) INFORMATION FOR SEQ ID NO: 6:

(i) SEQUENCE CHARACTERISTICS:
            (A) LENGTH: 23 amino acids
            (B) TYPE: amino acid
            (C) STRANDEDNESS: <Unknown>
            (D) TOPOLOGY: linear (ii) MOLECULE TYPE: peptide (vi) ORIGINAL SOURCE:
            (A) ORGANISM: Conus orchroleucus (ix) FEATURE:
            (A) NAME/KEY: Modified-site
            (B) LOCATION: 3..19
            (D) OTHER INFORMATION: /note= "Xaa at residues 3 and 4 is
                gamma-carboxyglutamic acid; Xaa at residues 11 and 19 may
                be any amino acid, but is preferably gamma-carboxyglutamic
                acid"

(xi) SEQUENCE DESCRIPTION: SEQ ID NO: 6:

Gly Glu Xaa Xaa Tyr Arg Lys Ala Met Ala Xaa Leu Glu Ala Lys Lys
1               5                   10                  15

Ala Gln Xaa Ala Leu Lys Ala
            20

(2) INFORMATION FOR SEQ ID NO: 7:

(i) SEQUENCE CHARACTERISTICS:
            (A) LENGTH: 19 amino acids
            (B) TYPE: amino acid
            (C) STRANDEDNESS: <Unknown>

(D) TOPOLOGY: linear (ii) MOLECULE TYPE: peptide (vi) ORIGINAL SOURCE:
            (A) ORGANISM: Conus gloriamaris (ix) FEATURE:
            (A) NAME/KEY: Modified-site
            (B) LOCATION: 3..14
            (D) OTHER INFORMATION: /note= "Xaa at residue 4 is
                gamma-carboxyglutamic acid; Xaa at residues 10 and 14 may
                be any amino acid, but is preferably gamma-carboxy
                glutamic acid"

(xi) SEQUENCE DESCRIPTION: SEQ ID NO: 7:

Gly Ala Lys Xaa Asp Arg Asn Asn Ala Xaa Ala Val Arg Xaa Arg Leu
1               5                   10                  15

Glu Glu Ile (2) INFORMATION FOR SEQ ID NO: 8:

(i) SEQUENCE CHARACTERISTICS:
            (A) LENGTH: 18 amino acids
            (B) TYPE: amino acid
            (C) STRANDEDNESS: <Unknown>
            (D) TOPOLOGY: linear (ii) MOLECULE TYPE: peptide (vi) ORIGINAL SOURCE:
            (A) ORGANISM: Conus caracteristicus (ix) FEATURE:
            (A) NAME/KEY: Modified-site
            (B) LOCATION: 3..14
            (D) OTHER INFORMATION: /note= "Xaa at residues 3 and 4 is
                gamma-carboxyglutamic acid; Xaa at residues 7, 10 and 14
                may be any amino acid, but is preferably
                gamma-carboxyglutamic acid"

(xi) SEQUENCE DESCRIPTION: SEQ ID NO: 8:

Gly Tyr Xaa Xaa Asp Arg Xaa Ile Ala Xaa Thr Val Arg Xaa Leu Glu
1               5                   10                  15

Glu Ala (2) INFORMATION FOR SEQ ID NO: 9:

(i) SEQUENCE CHARACTERISTICS:
            (A) LENGTH: 18 amino acids
            (B) TYPE: amino acid
            (C) STRANDEDNESS: <Unknown>
            (D) TOPOLOGY: linear (ii) MOLECULE TYPE: peptide (vi) ORIGINAL SOURCE:
            (A) ORGANISM: Conus quercinus (ix) FEATURE:
            (A) NAME/KEY: Modified-site
            (B) LOCATION: 3..14
            (D) OTHER INFORMATION: /note= "Xaa at residues 3 and 4 is
                gamma-carboxyglutamic acid; Xaa at residues 7, 10 and 14
                may be any amino acid, but is preferably
                gamma-carboxyglutamic acid"

(xi) SEQUENCE DESCRIPTION: SEQ ID NO: 9:

Gly Tyr Xaa Xaa Asp Arg Xaa Val Ala Xaa Thr Val Arg Xaa Leu Asp
1               5                   10                  15

Ala Ala (2) INFORMATION FOR SEQ ID NO: 10:

(i) SEQUENCE CHARACTERISTICS:
        (A) LENGTH: 5 amino acids
        (B) TYPE: amino acid
        (C) STRANDEDNESS: <Unknown>
        (D) TOPOLOGY: linear (ii) MOLECULE TYPE: peptide (v) FRAGMENT TYPE: internal (xi) SEQUENCE DESCRIPTION: SEQ ID NO: 10:

Lys Pro Gly Arg Lys
1          5

(2) INFORMATION FOR SEQ ID NO: 11:

(i) SEQUENCE CHARACTERISTICS:
        (A) LENGTH: 6 amino acids
        (B) TYPE: amino acid
        (C) STRANDEDNESS: <Unknown>
        (D) TOPOLOGY: linear (ii) MOLECULE TYPE: peptide (v) FRAGMENT TYPE: internal (xi) SEQUENCE DESCRIPTION: SEQ ID NO: 11:

Lys Pro Gly Arg Lys Asn
1          5

(2) INFORMATION FOR SEQ ID NO: 12:

(i) SEQUENCE CHARACTERISTICS:
        (A) LENGTH: 4 amino acids
        (B) TYPE: amino acid
        (C) STRANDEDNESS: <Unknown>
        (D) TOPOLOGY: linear (ii) MOLECULE TYPE: peptide (v) FRAGMENT TYPE: N-terminal (ix) FEATURE:
        (A) NAME/KEY: Modified-site
        (B) LOCATION: 3..4
        (D) OTHER INFORMATION: /note= "Xaa is
            gamma-carboxyglutamic acid"

(xi) SEQUENCE DESCRIPTION: SEQ ID NO: 12:

Gly Glu Xaa Xaa
1

(2) INFORMATION FOR SEQ ID NO: 13:

(i) SEQUENCE CHARACTERISTICS:
        (A) LENGTH: 6 amino acids
        (B) TYPE: amino acid
        (C) STRANDEDNESS: <Unknown>
        (D) TOPOLOGY: linear (ii) MOLECULE TYPE: peptide (v) FRAGMENT TYPE: internal (ix) FEATURE:
        (A) NAME/KEY: Modified-site
        (B) LOCATION: 3..6
        (D) OTHER INFORMATION: /note= "Xaa is
            gamma-carboxyglutamic acid"

-continued

```
    (xi) SEQUENCE DESCRIPTION: SEQ ID NO: 13:

Leu Gln Xaa Asn Gln Xaa
1               5

(2) INFORMATION FOR SEQ ID NO: 14:

(i) SEQUENCE CHARACTERISTICS:
        (A) LENGTH: 4 amino acids
        (B) TYPE: amino acid
        (C) STRANDEDNESS: <Unknown>
        (D) TOPOLOGY: linear (ii) MOLECULE TYPE: peptide (v) FRAGMENT TYPE: internal (ix) FEATURE:
        (A) NAME/KEY: Modified-site
        (B) LOCATION: 4
        (D) OTHER INFORMATION: /note= "Xaa is
            gamma-carboxyglutamic acid"

(xi) SEQUENCE DESCRIPTION: SEQ ID NO: 14:

Leu Ile Arg Xaa
1

(2) INFORMATION FOR SEQ ID NO: 15:

(i) SEQUENCE CHARACTERISTICS:
        (A) LENGTH: 6 amino acids
        (B) TYPE: amino acid
        (C) STRANDEDNESS: <Unknown>
        (D) TOPOLOGY: linear (ii) MOLECULE TYPE: peptide (v) FRAGMENT TYPE: internal (ix) FEATURE:
        (A) NAME/KEY: Modified-site
        (B) LOCATION: 6
        (D) OTHER INFORMATION: /note= "Xaa is
            gamma-carboxyglutamic acid"

(xi) SEQUENCE DESCRIPTION: SEQ ID NO: 15:

Tyr Gln Lys Met Leu Xaa
1               5

(2) INFORMATION FOR SEQ ID NO: 16:

(i) SEQUENCE CHARACTERISTICS:
        (A) LENGTH: 4 amino acids
        (B) TYPE: amino acid
        (C) STRANDEDNESS: <Unknown>
        (D) TOPOLOGY: linear (ii) MOLECULE TYPE: peptide (v) FRAGMENT TYPE: internal (ix) FEATURE:
        (A) NAME/KEY: Modified-site
        (B) LOCATION: 4
        (D) OTHER INFORMATION: /note= "Xaa is
            gamma-carboxyglutamic acid"

(xi) SEQUENCE DESCRIPTION: SEQ ID NO: 16:

Asn Leu Arg Xaa
1
```

(2) INFORMATION FOR SEQ ID NO: 17:

(i) SEQUENCE CHARACTERISTICS:
        (A) LENGTH: 7 amino acids
        (B) TYPE: amino acid
        (C) STRANDEDNESS: <Unknown>
        (D) TOPOLOGY: linear (ii) MOLECULE TYPE: peptide (v) FRAGMENT TYPE: C-terminal (xi) SEQUENCE DESCRIPTION: SEQ ID NO: 17:

Ala Glu Val Lys Lys Asn Ala
1               5

(2) INFORMATION FOR SEQ ID NO: 18:

(i) SEQUENCE CHARACTERISTICS:
        (A) LENGTH: 7 amino acids
        (B) TYPE: amino acid
        (C) STRANDEDNESS: <Unknown>
        (D) TOPOLOGY: linear (ii) MOLECULE TYPE: peptide (v) FRAGMENT TYPE: internal (ix) FEATURE:
        (A) NAME/KEY: Modified-site
        (B) LOCATION: 7
        (D) OTHER INFORMATION: /note= "Xaa is
            gamma-carboxyglutamic acid"

(xi) SEQUENCE DESCRIPTION: SEQ ID NO: 18:

Val Ala Lys Met Ala Ala Xaa
1               5

(2) INFORMATION FOR SEQ ID NO: 19:

(i) SEQUENCE CHARACTERISTICS:
        (A) LENGTH: 4 amino acids
        (B) TYPE: amino acid
        (C) STRANDEDNESS: <Unknown>
        (D) TOPOLOGY: linear (ii) MOLECULE TYPE: peptide (v) FRAGMENT TYPE: internal (ix) FEATURE:
        (A) NAME/KEY: Modified-site
        (B) LOCATION: 4
        (D) OTHER INFORMATION: /note= "Xaa is
            gamma-carboxyglutamic acid"

(xi) SEQUENCE DESCRIPTION: SEQ ID NO: 19:

Leu Ala Arg Xaa
1

(2) INFORMATION FOR SEQ ID NO: 20:

(i) SEQUENCE CHARACTERISTICS:
        (A) LENGTH: 12 amino acids
        (B) TYPE: amino acid
        (C) STRANDEDNESS: <Unknown>
        (D) TOPOLOGY: linear (ii) MOLECULE TYPE: peptide (v) FRAGMENT TYPE: C-terminal (xi) SEQUENCE DESCRIPTION: SEQ ID NO: 20:

```
Asn Ile Ala Lys Gly Cys Lys Val Asn Cys Tyr Pro
1               5                   10
```

(2) INFORMATION FOR SEQ ID NO: 21:

(i) SEQUENCE CHARACTERISTICS:
        (A) LENGTH: 4 amino acids
        (B) TYPE: amino acid
        (C) STRANDEDNESS: <Unknown>
        (D) TOPOLOGY: linear (ii) MOLECULE TYPE: peptide (v) FRAGMENT TYPE: C-terminal (xi) SEQUENCE DESCRIPTION: SEQ ID NO: 21:

```
Asp Ala Val Asn
1
```

(2) INFORMATION FOR SEQ ID NO: 22:

(i) SEQUENCE CHARACTERISTICS:
        (A) LENGTH: 6 amino acids
        (B) TYPE: amino acid
        (C) STRANDEDNESS: <Unknown>
        (D) TOPOLOGY: linear (ii) MOLECULE TYPE: peptide (v) FRAGMENT TYPE: internal (xi) SEQUENCE DESCRIPTION: SEQ ID NO: 22:

```
Leu Gln Ala Asn Gln Ala
1               5
```

(2) INFORMATION FOR SEQ ID NO: 23:

(i) SEQUENCE CHARACTERISTICS:
        (A) LENGTH: 4 amino acids
        (B) TYPE: amino acid
        (C) STRANDEDNESS: <Unknown>
        (D) TOPOLOGY: linear (ii) MOLECULE TYPE: peptide (v) FRAGMENT TYPE: internal (xi) SEQUENCE DESCRIPTION: SEQ ID NO: 23:

```
Leu Ile Arg Ala
1
```

(2) INFORMATION FOR SEQ ID NO: 24:

(i) SEQUENCE CHARACTERISTICS:
        (A) LENGTH: 6 amino acids
        (B) TYPE: amino acid
        (C) STRANDEDNESS: <Unknown>
        (D) TOPOLOGY: linear (ii) MOLECULE TYPE: peptide (v) FRAGMENT TYPE: internal (ix) FEATURE:
        (A) NAME/KEY: Modified-site
        (B) LOCATION: 6
        (D) OTHER INFORMATION: /note= "Xaa is
            gamma-carboxyglutamic acid"

(xi) SEQUENCE DESCRIPTION: SEQ ID NO: 24:

```
Leu Gln Ala Asn Gln Xaa
 1               5
```

(2) INFORMATION FOR SEQ ID NO: 25:

(i) SEQUENCE CHARACTERISTICS:
        (A) LENGTH: 6 amino acids
        (B) TYPE: amino acid
        (C) STRANDEDNESS: <Unknown>
        (D) TOPOLOGY: linear (ii) MOLECULE TYPE: peptide (v) FRAGMENT TYPE: internal (ix) FEATURE:
        (A) NAME/KEY: Modified-site
        (B) LOCATION: 6
        (D) OTHER INFORMATION: /note= "Xaa is
            gamma-carboxyglutamic acid"

(xi) SEQUENCE DESCRIPTION: SEQ ID NO: 25:

```
Leu Gln Ser Asn Gln Xaa
 1               5
```

(2) INFORMATION FOR SEQ ID NO: 26:

(i) SEQUENCE CHARACTERISTICS:
        (A) LENGTH: 6 amino acids
        (B) TYPE: amino acid
        (C) STRANDEDNESS: <Unknown>
        (D) TOPOLOGY: linear (ii) MOLECULE TYPE: peptide (v) FRAGMENT TYPE: internal (ix) FEATURE:
        (A) NAME/KEY: Modified-site
        (B) LOCATION: 6
        (D) OTHER INFORMATION: /note= "Xaa is
            gamma-carboxyglutamic acid"

(xi) SEQUENCE DESCRIPTION: SEQ ID NO: 26:

```
Leu Gln Thr Asn Gln Xaa
 1               5
```

(2) INFORMATION FOR SEQ ID NO: 27:

(i) SEQUENCE CHARACTERISTICS:
        (A) LENGTH: 4 amino acids
        (B) TYPE: amino acid
        (C) STRANDEDNESS: <Unknown>
        (D) TOPOLOGY: linear (ii) MOLECULE TYPE: peptide (v) FRAGMENT TYPE: N-terminal (ix) FEATURE:
        (A) NAME/KEY: Modified-site
        (B) LOCATION: 3..4
        (D) OTHER INFORMATION: /note= "Xaa is
            gamma-carboxyglutamic acid"

(xi) SEQUENCE DESCRIPTION: SEQ ID NO: 27:

```
Gly Asp Xaa Xaa
 1
```

(2) INFORMATION FOR SEQ ID NO: 28:

(i) SEQUENCE CHARACTERISTICS:

```
            (A) LENGTH: 6 amino acids
            (B) TYPE: amino acid
            (C) STRANDEDNESS: <Unknown>
            (D) TOPOLOGY: linear (ii) MOLECULE TYPE: peptide (v) FRAGMENT TYPE: internal (ix) FEATURE:
            (A) NAME/KEY: Modified-site
            (B) LOCATION: 6
            (D) OTHER INFORMATION: /note= "Xaa is
                 gamma-carboxyglutamic acid"

(xi) SEQUENCE DESCRIPTION: SEQ ID NO: 28:

Tyr Ser Lys Phe Ile Xaa
1               5

(2) INFORMATION FOR SEQ ID NO: 29:

(i) SEQUENCE CHARACTERISTICS:
            (A) LENGTH: 4 amino acids
            (B) TYPE: amino acid
            (C) STRANDEDNESS: <Unknown>
            (D) TOPOLOGY: linear (ii) MOLECULE TYPE: peptide (v) FRAGMENT TYPE: internal (ix) FEATURE:
            (A) NAME/KEY: Modified-site
            (B) LOCATION: 4
            (D) OTHER INFORMATION: /note= "Xaa is
                 gamma-carboxyglutamic acid"

(xi) SEQUENCE DESCRIPTION: SEQ ID NO: 29:

Arg Glu Arg Xaa
1

(2) INFORMATION FOR SEQ ID NO: 30:

(i) SEQUENCE CHARACTERISTICS:
            (A) LENGTH: 10 amino acids
            (B) TYPE: amino acid
            (C) STRANDEDNESS: <Unknown>
            (D) TOPOLOGY: linear (ii) MOLECULE TYPE: peptide (v) FRAGMENT TYPE: C-terminal (xi) SEQUENCE DESCRIPTION: SEQ ID NO: 30:

Ala Gly Arg Leu Asp Leu Ser Lys Phe Pro
1               5                   10

(2) INFORMATION FOR SEQ ID NO: 31:

(i) SEQUENCE CHARACTERISTICS:
            (A) LENGTH: 7 amino acids
            (B) TYPE: amino acid
            (C) STRANDEDNESS: <Unknown>
            (D) TOPOLOGY: linear (ii) MOLECULE TYPE: peptide (v) FRAGMENT TYPE: internal (ix) FEATURE:
            (A) NAME/KEY: Modified-site
            (B) LOCATION: 7
            (D) OTHER INFORMATION: /note= "Xaa is
```

```
              gamma-carboxyglutamic acid"

(xi) SEQUENCE DESCRIPTION: SEQ ID NO: 31:

Tyr Arg Lys Ala Met Ala Xaa
1               5

(2) INFORMATION FOR SEQ ID NO: 32:

(i) SEQUENCE CHARACTERISTICS:
        (A) LENGTH: 8 amino acids
        (B) TYPE: amino acid
        (C) STRANDEDNESS: <Unknown>
        (D) TOPOLOGY: linear (ii) MOLECULE TYPE: peptide (v) FRAGMENT TYPE: internal (ix) FEATURE:
        (A) NAME/KEY: Modified-site
        (B) LOCATION: 8
        (D) OTHER INFORMATION: /note= "Xaa is
              gamma-carboxyglutamic acid"

(xi) SEQUENCE DESCRIPTION: SEQ ID NO: 32:

Leu Glu Ala Lys Lys Ala Gln Xaa
1               5

(2) INFORMATION FOR SEQ ID NO: 33:

(i) SEQUENCE CHARACTERISTICS:
        (A) LENGTH: 4 amino acids
        (B) TYPE: amino acid
        (C) STRANDEDNESS: <Unknown>
        (D) TOPOLOGY: linear (ii) MOLECULE TYPE: peptide (v) FRAGMENT TYPE: C-terminal (xi) SEQUENCE DESCRIPTION: SEQ ID NO: 33:

Ala Leu Lys Ala
1

(2) INFORMATION FOR SEQ ID NO: 34:

(i) SEQUENCE CHARACTERISTICS:
        (A) LENGTH: 4 amino acids
        (B) TYPE: amino acid
        (C) STRANDEDNESS: <Unknown>
        (D) TOPOLOGY: linear (ii) MOLECULE TYPE: peptide (v) FRAGMENT TYPE: N-terminal (ix) FEATURE:
        (A) NAME/KEY: Modified-site
        (B) LOCATION: 3..4
        (D) OTHER INFORMATION: /note= "Xaa is
              gamma-carboxyglutamic acid"

(xi) SEQUENCE DESCRIPTION: SEQ ID NO: 34:

Gly Tyr Xaa Xaa
1

(2) INFORMATION FOR SEQ ID NO: 35:

(i) SEQUENCE CHARACTERISTICS:
        (A) LENGTH: 6 amino acids
        (B) TYPE: amino acid
```

```
            (C) STRANDEDNESS: <Unknown>
            (D) TOPOLOGY: linear (ii) MOLECULE TYPE: peptide (v) FRAGMENT TYPE: internal (ix) FEATURE:
            (A) NAME/KEY: Modified-site
            (B) LOCATION: 3..6
            (D) OTHER INFORMATION: /note= "Xaa is
                gamma-carboxyglutamic acid"

(xi) SEQUENCE DESCRIPTION: SEQ ID NO: 35:

Asp Arg Xaa Val Ala Xaa
1               5

(2) INFORMATION FOR SEQ ID NO: 36:

(i) SEQUENCE CHARACTERISTICS:
            (A) LENGTH: 4 amino acids
            (B) TYPE: amino acid
            (C) STRANDEDNESS: <Unknown>
            (D) TOPOLOGY: linear (ii) MOLECULE TYPE: peptide (v) FRAGMENT TYPE: internal (ix) FEATURE:
            (A) NAME/KEY: Modified-site
            (B) LOCATION: 4
            (D) OTHER INFORMATION: /note= "Xaa is
                gamma-carboxyglutamic acid"

(xi) SEQUENCE DESCRIPTION: SEQ ID NO: 36:

Thr Val Arg Xaa
1

(2) INFORMATION FOR SEQ ID NO: 37:

(i) SEQUENCE CHARACTERISTICS:
            (A) LENGTH: 4 amino acids
            (B) TYPE: amino acid
            (C) STRANDEDNESS: <Unknown>
            (D) TOPOLOGY: linear (ii) MOLECULE TYPE: peptide (v) FRAGMENT TYPE: C-terminal (xi) SEQUENCE DESCRIPTION: SEQ ID NO: 37:

Leu Asp Ala Ala
1

(2) INFORMATION FOR SEQ ID NO: 38:

(i) SEQUENCE CHARACTERISTICS:
            (A) LENGTH: 6 amino acids
            (B) TYPE: amino acid
            (C) STRANDEDNESS: <Unknown>
            (D) TOPOLOGY: linear (ii) MOLECULE TYPE: peptide (v) FRAGMENT TYPE: internal (ix) FEATURE:
            (A) NAME/KEY: Modified-site
            (B) LOCATION: 3..6
            (D) OTHER INFORMATION: /note= "Xaa is
                gamma-carboxyglutamic acid"
```

(xi) SEQUENCE DESCRIPTION: SEQ ID NO: 38:

Asp Arg Xaa Ile Ala Xaa
1               5

(2) INFORMATION FOR SEQ ID NO: 39:

(i) SEQUENCE CHARACTERISTICS:
            (A) LENGTH: 4 amino acids
            (B) TYPE: amino acid
            (C) STRANDEDNESS: <Unknown>
            (D) TOPOLOGY: linear (ii) MOLECULE TYPE: peptide (v) FRAGMENT TYPE: C-terminal (xi) SEQUENCE DESCRIPTION: SEQ ID NO: 39:

Leu Glu Glu Ala
1

(2) INFORMATION FOR SEQ ID NO: 40:

(i) SEQUENCE CHARACTERISTICS:
            (A) LENGTH: 4 amino acids
            (B) TYPE: amino acid
            (C) STRANDEDNESS: <Unknown>
            (D) TOPOLOGY: linear (ii) MOLECULE TYPE: peptide (v) FRAGMENT TYPE: N-terminal (ix) FEATURE:
            (A) NAME/KEY: Modified-site
            (B) LOCATION: 4
            (D) OTHER INFORMATION: /note= "Xaa is
                gamma-carboxyglutamic acid"

(xi) SEQUENCE DESCRIPTION: SEQ ID NO: 40:

Gly Ala Lys Xaa
1

(2) INFORMATION FOR SEQ ID NO: 41:

(i) SEQUENCE CHARACTERISTICS:
            (A) LENGTH: 6 amino acids
            (B) TYPE: amino acid
            (C) STRANDEDNESS: <Unknown>
            (D) TOPOLOGY: linear (ii) MOLECULE TYPE: peptide (v) FRAGMENT TYPE: internal (ix) FEATURE:
            (A) NAME/KEY: Modified-site
            (B) LOCATION: 6
            (D) OTHER INFORMATION: /note= "Xaa is
                gamma-carboxyglutamic acid"

(xi) SEQUENCE DESCRIPTION: SEQ ID NO: 41:

Asp Arg Asn Asn Ala Xaa
1               5

(2) INFORMATION FOR SEQ ID NO: 42:

(i) SEQUENCE CHARACTERISTICS:
            (A) LENGTH: 4 amino acids
            (B) TYPE: amino acid
            (C) STRANDEDNESS: <Unknown>
            (D) TOPOLOGY: linear (ii) MOLECULE TYPE: peptide (v) FRAGMENT TYPE: internal (ix) FEATURE:
             (A) NAME/KEY: Modified-site
             (B) LOCATION: 4
             (D) OTHER INFORMATION: /note= "Xaa is
                 gamma-carboxyglutamic acid"

(xi) SEQUENCE DESCRIPTION: SEQ ID NO: 42:

Ala Val Arg Xaa
1

(2) INFORMATION FOR SEQ ID NO: 43:

(i) SEQUENCE CHARACTERISTICS:
             (A) LENGTH: 5 amino acids
             (B) TYPE: amino acid
             (C) STRANDEDNESS: <Unknown>
             (D) TOPOLOGY: linear (ii) MOLECULE TYPE: peptide (v) FRAGMENT TYPE: C-terminal (xi) SEQUENCE DESCRIPTION: SEQ ID NO: 43:

Arg Leu Glu Glu Ile
1               5

(2) INFORMATION FOR SEQ ID NO: 44:

(i) SEQUENCE CHARACTERISTICS:
             (A) LENGTH: 17 base pairs
             (B) TYPE: nucleic acid
             (C) STRANDEDNESS: single
             (D) TOPOLOGY: linear (ii) MOLECULE TYPE: other nucleic acid
             (A) DESCRIPTION: /desc = "probe"

(xi) SEQUENCE DESCRIPTION: SEQ ID NO: 44:

CARGARAAYC ARGARYT                                                17

(2) INFORMATION FOR SEQ ID NO: 45:

(i) SEQUENCE CHARACTERISTICS:
             (A) LENGTH: 718 base pairs
             (B) TYPE: nucleic acid
             (C) STRANDEDNESS: single
             (D) TOPOLOGY: linear (ii) MOLECULE TYPE: DNA (cDNA)

(vi) ORIGINAL SOURCE:
             (A) ORGANISM: Conus geographus (ix) FEATURE:
             (A) NAME/KEY: CDS
             (B) LOCATION: 110..409

(xi) SEQUENCE DESCRIPTION: SEQ ID NO: 45:

GCGCCTTGCC TGAGGAACGA CGTGTCTTCC CCTGCCCTCT CTGTCTTCCT GACTGCAGCC      60

TTGAGCCACC CAGCCGTCAT CTCTACCATC GACTTCACCC TGATTGGCG ATG CAC        115
                                                      Met His
                                                        1

CTG TAC ACG TAT CTG TAT CTG CTG GTG CCC CTG GTG ACC TTC CAC CTA      163
Leu Tyr Thr Tyr Leu Tyr Leu Leu Val Pro Leu Val Thr Phe His Leu
      5                  10                  15

```
ATC CTA GGC ACG GGC ACA CTA GAT GAT GGA GGC GCA CTG ACT GAA CGC      211
Ile Leu Gly Thr Gly Thr Leu Asp Asp Gly Gly Ala Leu Thr Glu Arg
        20                  25                  30

CGT TCA GCT GAC GCC ACA GCG CTG AAA GCT GAG CCT GTC CTC CTG CAG      259
Arg Ser Ala Asp Ala Thr Ala Leu Lys Ala Glu Pro Val Leu Leu Gln
 35                  40                  45                  50

AAA TCC GCT GCC CGC AGC ACC GAC GAC AAT GGC AAG GAC AGG TTG ACT      307
Lys Ser Ala Ala Arg Ser Thr Asp Asp Asn Gly Lys Asp Arg Leu Thr
                 55                  60                  65

CAG ATG AAG AGG ATT CTC AAA CAG CGA GGA AAC AAA GCC AGA GGC GAA      355
Gln Met Lys Arg Ile Leu Lys Gln Arg Gly Asn Lys Ala Arg Gly Glu
                     70                  75                  80

GAA GAA GTT CAA GAG AAT CAG GAA TTG ATC AGA GAA AAA AGT AAT GGA      403
Glu Glu Val Gln Glu Asn Gln Glu Leu Ile Arg Glu Lys Ser Asn Gly
             85                  90                  95

AAA AGA TAATCAAGCT GGTGTTCCAC GTTATACCCG TCAGTTCTAA AATCCCCAGA       459
Lys Arg
    100

TAGATCGTTC CCTATTTTTG CCACATTCTT TCTTTCTCTT TCATTTAAT TCCCCAAATA     519

TTTCATGTTT ATTCTCACGT AATTGTAAAA TTTTTAGGAG GAATGGTGTG TGTGTATGTG    579

CAAACTGTAT CATACATAAA TAATGCGAAT TTAAGGAAGA AATTTTGCAG ATCCATGCAC    639

AGAAAGTCGT TAAAGACAAA TTGTATGAAT AACCAAATTT GATTTGAATC AATAAAGAAC    699

CCACTAAGTG AAAAAAAA                                                  718

(2) INFORMATION FOR SEQ ID NO: 46:

(i) SEQUENCE CHARACTERISTICS:
        (A) LENGTH: 100 amino acids
        (B) TYPE: amino acid
        (D) TOPOLOGY: linear (ii) MOLECULE TYPE: protein (xi) SEQUENCE DESCRIPTION: SEQ ID NO: 46:

Met His Leu Tyr Thr Tyr Leu Tyr Leu Leu Val Pro Leu Val Thr Phe
 1               5                  10                  15

His Leu Ile Leu Gly Thr Gly Thr Leu Asp Asp Gly Gly Ala Leu Thr
                 20                  25                  30

Glu Arg Arg Ser Ala Asp Ala Thr Ala Leu Lys Ala Glu Pro Val Leu
             35                  40                  45

Leu Gln Lys Ser Ala Ala Arg Ser Thr Asp Asp Asn Gly Lys Asp Arg
 50                  55                  60

Leu Thr Gln Met Lys Arg Ile Leu Lys Gln Arg Gly Asn Lys Ala Arg
 65                  70                  75                  80

Gly Glu Glu Glu Val Gln Glu Asn Gln Glu Leu Ile Arg Glu Lys Ser
             85                  90                  95

Asn Gly Lys Arg
            100

(2) INFORMATION FOR SEQ ID NO: 47:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "probe"
```

(xi) SEQUENCE DESCRIPTION: SEQ ID NO: 47:

CCYTTNGCDA TRTTYTC                                                   17

(2) INFORMATION FOR SEQ ID NO: 48:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "probe"

(xi) SEQUENCE DESCRIPTION: SEQ ID NO: 48:

GCCGTGCCTA GGATTA                                                    16

(2) INFORMATION FOR SEQ ID NO: 49:

(i) SEQUENCE CHARACTERISTICS:
        (A) LENGTH: 580 base pairs
        (B) TYPE: nucleic acid
        (C) STRANDEDNESS: single
        (D) TOPOLOGY: linear (ii) MOLECULE TYPE: DNA (cDNA)

(vi) ORIGINAL SOURCE:
        (A) ORGANISM: Conus radiatus (ix) FEATURE:
        (A) NAME/KEY: CDS
        (B) LOCATION: 127..447

(xi) SEQUENCE DESCRIPTION: SEQ ID NO: 49:

TTCTGTCAGT TCAGATTTCG CCGTGCCCGA GGAACGACGT GTCTTCCCTT GCTCTCTCCA     60

TCTTCCTGAC AGCAGCTTTG AGCCACCCAG CCGTCATCTC TGCCGTCGAC TTCACCCTGA   120

TTGGCG ATG CAA CTG TAC ACG TAT CTG TAT CTG CTG GTG TCC CTG GTG     168
       Met Gln Leu Tyr Thr Tyr Leu Tyr Leu Leu Val Ser Leu Val
        1               5                  10

ACC TTC TAC CTA ATC CTA GGC ACG GGC ACG CTA GGT CAT GGA GGC GCA    216
Thr Phe Tyr Leu Ile Leu Gly Thr Gly Thr Leu Gly His Gly Gly Ala
 15                  20                  25                  30

CTG ACT GAA CGC CGT TCG ACT GAC GCC ACA GCA CTG AAA CCT GAA CCT    264
Leu Thr Glu Arg Arg Ser Thr Asp Ala Thr Ala Leu Lys Pro Glu Pro
                 35                  40                  45

GTC CTC CTG CAG AAA TCC TCT GCC CGC AGC ACC GAC GAC AAT GGC AAC    312
Val Leu Leu Gln Lys Ser Ser Ala Arg Ser Thr Asp Asp Asn Gly Asn
         50                  55                  60

GAC AGG TTG ACT CAG ATG AAG AGG ATT CTC AAA AAG CGA GGA AAC AAA    360
Asp Arg Leu Thr Gln Met Lys Arg Ile Leu Lys Lys Arg Gly Asn Lys
     65                  70                  75

GCC AGA GGA GAA GAA GAA GTT GCA AAA ATG GCG GCA GAG CTT GCC AGA    408
Ala Arg Gly Glu Glu Glu Val Ala Lys Met Ala Ala Glu Leu Ala Arg
 80                  85                  90

GAA AAC ATT GCA AAA GGC TGT AAA GTT AAT TGT TAC CCG TGACACTCGT     457
Glu Asn Ile Ala Lys Gly Cys Lys Val Asn Cys Tyr Pro
 95                 100                 105

CAGTTCTAAA GTCCCCAGAT AGATCGTTCC CTATTTTTGC CACATTCTTT CTTTCTCTTT   517

TCATTTAATT CCCCAAATCT TTCATGTCTA TTCTCACGTA AAGAATTTAA TTGTAGAATT   577

TTT                                                                 580

(2) INFORMATION FOR SEQ ID NO: 50:

(i) SEQUENCE CHARACTERISTICS:
        (A) LENGTH: 107 amino acids
        (B) TYPE: amino acid
        (D) TOPOLOGY: linear (ii) MOLECULE TYPE: protein (xi) SEQUENCE DESCRIPTION: SEQ ID NO: 50:

```
Met Gln Leu Tyr Thr Tyr Leu Tyr Leu Leu Val Ser Leu Val Thr Phe
 1               5                  10                  15

Tyr Leu Ile Leu Gly Thr Gly Thr Leu Gly His Gly Gly Ala Leu Thr
                20                  25                  30

Glu Arg Arg Ser Thr Asp Ala Thr Ala Leu Lys Pro Glu Pro Val Leu
            35                  40                  45

Leu Gln Lys Ser Ser Ala Arg Ser Thr Asp Asp Asn Gly Asn Asp Arg
        50                  55                  60

Leu Thr Gln Met Lys Arg Ile Leu Lys Lys Arg Gly Asn Lys Ala Arg
65                  70                  75                  80

Gly Glu Glu Glu Val Ala Lys Met Ala Ala Glu Leu Ala Arg Glu Asn
                85                  90                  95

Ile Ala Lys Gly Cys Lys Val Asn Cys Tyr Pro
                100                 105
```

(2) INFORMATION FOR SEQ ID NO: 51:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 51:

TGCTCGAATA AACATGAAAG ATTTGGGGAA                                         30

(2) INFORMATION FOR SEQ ID NO: 52:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 52:

TCTGCGATGC AACTGTACAC GTATCTG                                           27

(2) INFORMATION FOR SEQ ID NO: 53:

(i) SEQUENCE CHARACTERISTICS:
        (A) LENGTH: 394 base pairs
        (B) TYPE: nucleic acid
        (C) STRANDEDNESS: single
        (D) TOPOLOGY: linear (ii) MOLECULE TYPE: DNA (cDNA)

(vi) ORIGINAL SOURCE:
        (A) ORGANISM: Conus ochroleucus

-continued

```
    (ix) FEATURE:
          (A) NAME/KEY: CDS
          (B) LOCATION: 1..294

(xi) SEQUENCE DESCRIPTION: SEQ ID NO: 53:

TAT CTG CTG GTG CCC CTG GTG ACC TTC CTC CTA ATC CTA GGC ACG GGC      48
Tyr Leu Leu Val Pro Leu Val Thr Phe Leu Leu Ile Leu Gly Thr Gly
 1               5                  10                  15

ACA CTA GAT CAT GGA GGC GCA CTG ACT GAA CGC CGT TCG ACT GAC GCC      96
Thr Leu Asp His Gly Gly Ala Leu Thr Glu Arg Arg Ser Thr Asp Ala
                20                  25                  30

ATA GCA CTG AAA CCT GAG CCT GTC CTC CTG CAG AAA TCC TCT GCC CGC     144
Ile Ala Leu Lys Pro Glu Pro Val Leu Leu Gln Lys Ser Ser Ala Arg
        35                  40                  45

AGC ACC GAC GAC AAT GGC GGC GAC AGG TTG ACT CAG ATG AAG AGG ATT     192
Ser Thr Asp Asp Asn Gly Gly Asp Arg Leu Thr Gln Met Lys Arg Ile
    50                  55                  60

CTC AAA AAG CGA GGA AAC AAA GCC AGA GGC GAA GAA GAA TAT AGA AAA     240
Leu Lys Lys Arg Gly Asn Lys Ala Arg Gly Glu Glu Glu Tyr Arg Lys
65                  70                  75                  80

GCG ATG GCA GAG CTC GAA GCT AAA AAA GCT CAA GAA GCT CTA AAG GCG     288
Ala Met Ala Glu Leu Glu Ala Lys Lys Ala Gln Glu Ala Leu Lys Ala
                85                  90                  95

GGA CGA TAATCAAGTT GGGTGTTCCA CGTGACACTC GTCAGTTCTA AAGTCCCCAG      344
Gly Arg

ATAGATCGTT CCCTATTTTT GCCACATTCT TTCTTTCTCT TTTCATTTAA              394

(2) INFORMATION FOR SEQ ID NO: 54:

(i) SEQUENCE CHARACTERISTICS:
          (A) LENGTH: 98 amino acids
          (B) TYPE: amino acid
          (D) TOPOLOGY: linear (ii) MOLECULE TYPE: protein (xi) SEQUENCE DESCRIPTION: SEQ ID NO: 54:

Tyr Leu Leu Val Pro Leu Val Thr Phe Leu Leu Ile Leu Gly Thr Gly
 1               5                  10                  15

Thr Leu Asp His Gly Gly Ala Leu Thr Glu Arg Arg Ser Thr Asp Ala
                20                  25                  30

Ile Ala Leu Lys Pro Glu Pro Val Leu Leu Gln Lys Ser Ser Ala Arg
        35                  40                  45

Ser Thr Asp Asp Asn Gly Gly Asp Arg Leu Thr Gln Met Lys Arg Ile
    50                  55                  60

Leu Lys Lys Arg Gly Asn Lys Ala Arg Gly Glu Glu Glu Tyr Arg Lys
65                  70                  75                  80

Ala Met Ala Glu Leu Glu Ala Lys Lys Ala Gln Glu Ala Leu Lys Ala
                85                  90                  95

Gly Arg (2) INFORMATION FOR SEQ ID NO: 55:

(i) SEQUENCE CHARACTERISTICS:
          (A) LENGTH: 472 base pairs
          (B) TYPE: nucleic acid
          (C) STRANDEDNESS: single
          (D) TOPOLOGY: linear (ii) MOLECULE TYPE: DNA (cDNA)

(vi) ORIGINAL SOURCE:
```

-continued

```
        (A) ORGANISM: Conus sulcatus (ix) FEATURE:
         (A) NAME/KEY: CDS
         (B) LOCATION: 6..314

(xi) SEQUENCE DESCRIPTION: SEQ ID NO: 55:

GGGCG ATG CAA CTG TAC ACG TAT CTG TAT CTG CTG GTG CCC CTG GTG         47
      Met Gln Leu Tyr Thr Tyr Leu Tyr Leu Leu Val Pro Leu Val
       1               5                  10

ACC TTC CAC CTA ATC CTA GGC ACG GGC ACA CTA GAT CAT GGA GGC GCA       95
Thr Phe His Leu Ile Leu Gly Thr Gly Thr Leu Asp His Gly Gly Ala
 15                  20                  25                  30

CTG ACT GAA CGC CGT TCG ACT GAC GCC ACA GCA CTG AAA CCT GAG CCT      143
Leu Thr Glu Arg Arg Ser Thr Asp Ala Thr Ala Leu Lys Pro Glu Pro
                 35                  40                  45

GTC CTG CAG AAA TCC GCT GCC CGC AGC ACC GAC GAC AAT GGC AAG GAC      191
Val Leu Gln Lys Ser Ala Ala Arg Ser Thr Asp Asp Asn Gly Lys Asp
             50                  55                  60

AGG CTG ACT CAG ATG AAG AGG ATT CTC AAA AAG CGA GGA AAG AAT GCC      239
Arg Leu Thr Gln Met Lys Arg Ile Leu Lys Lys Arg Gly Lys Asn Ala
         65                  70                  75

CGT GGC GAT GAA GAA TAT TCA AAG TTT ATA GAG AGA GAA CGC GAA GCA      287
Arg Gly Asp Glu Glu Tyr Ser Lys Phe Ile Glu Arg Glu Arg Glu Ala
     80                  85                  90

GGA AGA CTG GAT TTG TCA AAA TTC CCG TGACACTCGT CAGTTCTAAA            334
Gly Arg Leu Asp Leu Ser Lys Phe Pro
 95                 100

ATCCCCAGAT AGATCGTTCC CTATTTTTGT CACATTCTTT CTTTCTTTTT TCATTAATTC    394

CCCAAATCTT TCATGTTTAT TCTCACGTAA TGAATTTAAT TGTAGAATTT TTAGGGGGAA    454

GGGGGGGGGG CGAAACTG                                                  472

(2) INFORMATION FOR SEQ ID NO: 56:

(i) SEQUENCE CHARACTERISTICS:
         (A) LENGTH: 103 amino acids
         (B) TYPE: amino acid
         (D) TOPOLOGY: linear (ii) MOLECULE TYPE: protein (xi) SEQUENCE DESCRIPTION: SEQ ID NO: 56:

Met Gln Leu Tyr Thr Tyr Leu Tyr Leu Leu Val Pro Leu Val Thr Phe
 1               5                  10                  15

His Leu Ile Leu Gly Thr Gly Thr Leu Asp His Gly Gly Ala Leu Thr
             20                  25                  30

Glu Arg Arg Ser Thr Asp Ala Thr Ala Leu Lys Pro Glu Pro Val Leu
         35                  40                  45

Gln Lys Ser Ala Ala Arg Ser Thr Asp Asp Asn Gly Lys Asp Arg Leu
     50                  55                  60

Thr Gln Met Lys Arg Ile Leu Lys Lys Arg Gly Lys Asn Ala Arg Gly
 65                  70                  75                  80

Asp Glu Glu Tyr Ser Lys Phe Ile Glu Arg Glu Arg Glu Ala Gly Arg
                 85                  90                  95

Leu Asp Leu Ser Lys Phe Pro
             100

(2) INFORMATION FOR SEQ ID NO: 57:

(i) SEQUENCE CHARACTERISTICS:
```

(A) LENGTH: 379 base pairs
    (B) TYPE: nucleic acid
    (C) STRANDEDNESS: single
    (D) TOPOLOGY: linear (ii) MOLECULE TYPE: DNA (cDNA)

(vi) ORIGINAL SOURCE:
    (A) ORGANISM: Conus lynceus (ix) FEATURE:
    (A) NAME/KEY: CDS
    (B) LOCATION: 1..282

(xi) SEQUENCE DESCRIPTION: SEQ ID NO: 57:

```
TAT CTG CTG GTG CCC CTG GTG ACC TTC CAC CTA ATC CTA GGC ACG GGC         48
Tyr Leu Leu Val Pro Leu Val Thr Phe His Leu Ile Leu Gly Thr Gly
 1               5                  10                  15

ACA CTA GAT CAT GGA GGC GCA CTG ACT GAA CGC CGT TCG ACT GAC GCC         96
Thr Leu Asp His Gly Gly Ala Leu Thr Glu Arg Arg Ser Thr Asp Ala
            20                  25                  30

ATA GCA CTG AAA CCT GAG CCT GTC CTC CTG CAG AAA TCC TCT GCC CGC        144
Ile Ala Leu Lys Pro Glu Pro Val Leu Leu Gln Lys Ser Ser Ala Arg
        35                  40                  45

AGC ACC GAC GAC AAT GGC AAC GAC AGG TTG ACT CAG ATG AAG AGG ATT        192
Ser Thr Asp Asp Asn Gly Asn Asp Arg Leu Thr Gln Met Lys Arg Ile
 50                  55                  60

CTC AAA AAG CGA GGA AAC AAA GCC AGA GGC GAA GAG GAA GTT GCA AAA        240
Leu Lys Lys Arg Gly Asn Lys Ala Arg Gly Glu Glu Glu Val Ala Lys
 65                  70                  75                  80

ATG GCG GCA GAG CTT GCC AGA GAA GAC GCT GTA AAT GGG AAA                282
Met Ala Ala Glu Leu Ala Arg Glu Asp Ala Val Asn Gly Lys
                 85                  90

TGATAATCAA GTTGGGTGTT CCACGTGACA CTCGTCAGTT CTAAAGTCCC CAGATAGATC      342

GTGCCCTATT TTTGCCACAT TCTTTCTTTC TCTTTTT                              379
```

(2) INFORMATION FOR SEQ ID NO: 58:

(i) SEQUENCE CHARACTERISTICS:
        (A) LENGTH: 94 amino acids
        (B) TYPE: amino acid
        (D) TOPOLOGY: linear (ii) MOLECULE TYPE: protein (xi) SEQUENCE DESCRIPTION: SEQ ID NO: 58:

```
Tyr Leu Leu Val Pro Leu Val Thr Phe His Leu Ile Leu Gly Thr Gly
 1               5                  10                  15

Thr Leu Asp His Gly Gly Ala Leu Thr Glu Arg Arg Ser Thr Asp Ala
            20                  25                  30

Ile Ala Leu Lys Pro Glu Pro Val Leu Leu Gln Lys Ser Ser Ala Arg
        35                  40                  45

Ser Thr Asp Asp Asn Gly Asn Asp Arg Leu Thr Gln Met Lys Arg Ile
 50                  55                  60

Leu Lys Lys Arg Gly Asn Lys Ala Arg Gly Glu Glu Glu Val Ala Lys
 65                  70                  75                  80

Met Ala Ala Glu Leu Ala Arg Glu Asp Ala Val Asn Gly Lys
                 85                  90
```

(2) INFORMATION FOR SEQ ID NO: 59:

(i) SEQUENCE CHARACTERISTICS:
        (A) LENGTH: 31 base pairs (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 59:

GGAATTCAAT AAACATGAAA GATTTGGGGA A                                  31

(2) INFORMATION FOR SEQ ID NO: 60:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 60:

GGAATTCGCG ATGCAACTGT ACACGTATCT G                                  31

(2) INFORMATION FOR SEQ ID NO: 61:

(i) SEQUENCE CHARACTERISTICS:
        (A) LENGTH: 386 base pairs
        (B) TYPE: nucleic acid
        (C) STRANDEDNESS: single
        (D) TOPOLOGY: linear (ii) MOLECULE TYPE: DNA (cDNA)

(vi) ORIGINAL SOURCE:
        (A) ORGANISM: Conus gloriamaris (ix) FEATURE:
        (A) NAME/KEY: CDS
        (B) LOCATION: 1..285

(xi) SEQUENCE DESCRIPTION: SEQ ID NO: 61:

TGT CTG CTG GTG CCC CTG GTG ACC CTC TAC GTA ATT CTA GGC ACG GGC    48
Cys Leu Leu Val Pro Leu Val Thr Leu Tyr Val Ile Leu Gly Thr Gly
 1               5                  10                  15

ACA CTA GCT CAT GGA GGC GCA CTG ACC GAA CGC CGT TTG GCT CAC GCC    96
Thr Leu Ala His Gly Gly Ala Leu Thr Glu Arg Arg Leu Ala His Ala
            20                  25                  30

AGA GCA ATG GAA CCT GAT CCT GTC CTC CTG CAG AAA TCC GCT GCC CGC   144
Arg Ala Met Glu Pro Asp Pro Val Leu Leu Gln Lys Ser Ala Ala Arg
        35                  40                  45

AGC ACC GAC GAC AAC GGC AAG GAC AGG ATG ACA CAG AGG AAG AGG ATT   192
Ser Thr Asp Asp Asn Gly Lys Asp Arg Met Thr Gln Arg Lys Arg Ile
 50                  55                  60

CTC AAA AAG CGA GGA AAC ACG GCC AGA GGC GCG AAA GAA GAT AGA AAT   240
Leu Lys Lys Arg Gly Asn Thr Ala Arg Gly Ala Lys Glu Asp Arg Asn
 65                  70                  75                  80

AAT GCG GAG GCT GTT AGA GAA AGA CTC GAA GAA ATA GGA AAA AGA       285
Asn Ala Glu Ala Val Arg Glu Arg Leu Glu Glu Ile Gly Lys Arg
                 85                  90                  95

TAATCAAGCT GGGTGTTTCA CGTGACACTC ATCAGTTCTA AAGTCCCCAG ATAGATCGTT  345

CCCTATTTTT GCCATATTTC TTTCTTTCTC TTTTCATTTA A                    386

(2) INFORMATION FOR SEQ ID NO: 62:

(i) SEQUENCE CHARACTERISTICS:

(A) LENGTH: 95 amino acids
        (B) TYPE: amino acid
        (D) TOPOLOGY: linear (ii) MOLECULE TYPE: protein (xi) SEQUENCE DESCRIPTION: SEQ ID NO: 62:

Cys Leu Leu Val Pro Leu Val Thr Leu Tyr Val Ile Leu Gly Thr Gly
 1               5                  10                  15

Thr Leu Ala His Gly Gly Ala Leu Thr Glu Arg Arg Leu Ala His Ala
             20                  25                  30

Arg Ala Met Glu Pro Asp Pro Val Leu Leu Gln Lys Ser Ala Ala Arg
         35                  40                  45

Ser Thr Asp Asp Asn Gly Lys Asp Arg Met Thr Gln Arg Lys Arg Ile
 50                  55                  60

Leu Lys Lys Arg Gly Asn Thr Ala Arg Gly Ala Lys Glu Asp Arg Asn
 65                  70                  75                  80

Asn Ala Glu Ala Val Arg Glu Arg Leu Glu Glu Ile Gly Lys Arg
                 85                  90                  95

(2) INFORMATION FOR SEQ ID NO: 63:

(i) SEQUENCE CHARACTERISTICS:
        (A) LENGTH: 356 base pairs
        (B) TYPE: nucleic acid
        (C) STRANDEDNESS: single
        (D) TOPOLOGY: linear (ii) MOLECULE TYPE: DNA (cDNA)

(vi) ORIGINAL SOURCE:
        (A) ORGANISM: Conus caracteristicus (ix) FEATURE:
        (A) NAME/KEY: CDS
        (B) LOCATION: 1..279

(xi) SEQUENCE DESCRIPTION: SEQ ID NO: 63:

TAT CTG CTG GTG CCC CTG GTG GCC TTC CAC CTA ATC CTA GGC ACG GGC        48
Tyr Leu Leu Val Pro Leu Val Ala Phe His Leu Ile Leu Gly Thr Gly
 1               5                  10                  15

ACG CTA GCT CAT GGA GAC GCA CTG ACT GAA CGC CGT TCG GCT GAT GCC        96
Thr Leu Ala His Gly Asp Ala Leu Thr Glu Arg Arg Ser Ala Asp Ala
             20                  25                  30

ACA GCA CTG AAA CCT GAG CCT GTC CTC CTG CAG AAA TCC GCT GCC CGC       144
Thr Ala Leu Lys Pro Glu Pro Val Leu Leu Gln Lys Ser Ala Ala Arg
         35                  40                  45

AGC ACT GAC GAC AAT GGC AAG GAC AGG TTG ACT CAG AGG AAG AGG ACT       192
Ser Thr Asp Asp Asn Gly Lys Asp Arg Leu Thr Gln Arg Lys Arg Thr
 50                  55                  60

CTC AAA AAG CGA GGA AAC ATG GCC AGA GGC TAC GAA GAA GAT AGA GAG       240
Leu Lys Lys Arg Gly Asn Met Ala Arg Gly Tyr Glu Glu Asp Arg Glu
 65                  70                  75                  80

ATT GCG GAG ACT GTT AGA GAA CTC GAA GAA GCA GGA AAA TGAAAAAGAT        289
Ile Ala Glu Thr Val Arg Glu Leu Glu Glu Ala Gly Lys
                 85                  90

AGTTCTAAAG TCCCCAGATA TATCGTTCCC TATTTTTGCC ACATTCTTTC TTTCTCTTTT     349

ATTTTAA                                                               356

(2) INFORMATION FOR SEQ ID NO: 64:

(i) SEQUENCE CHARACTERISTICS:
        (A) LENGTH: 93 amino acids (B) TYPE: amino acid
            (D) TOPOLOGY: linear (ii) MOLECULE TYPE: protein (xi) SEQUENCE DESCRIPTION: SEQ ID NO: 64:

Tyr Leu Leu Val Pro Leu Val Ala Phe His Leu Ile Leu Gly Thr Gly
 1               5                  10                  15

Thr Leu Ala His Gly Asp Ala Leu Thr Glu Arg Arg Ser Ala Asp Ala
             20                  25                  30

Thr Ala Leu Lys Pro Glu Pro Val Leu Leu Gln Lys Ser Ala Ala Arg
         35                  40                  45

Ser Thr Asp Asp Asn Gly Lys Asp Arg Leu Thr Gln Arg Lys Arg Thr
 50                  55                  60

Leu Lys Lys Arg Gly Asn Met Ala Arg Gly Tyr Glu Asp Arg Glu
 65                  70                  75                  80

Ile Ala Glu Thr Val Arg Glu Leu Glu Glu Ala Gly Lys
             85                  90

(2) INFORMATION FOR SEQ ID NO: 65:

(i) SEQUENCE CHARACTERISTICS:
        (A) LENGTH: 390 base pairs
        (B) TYPE: nucleic acid
        (C) STRANDEDNESS: single
        (D) TOPOLOGY: linear (ii) MOLECULE TYPE: DNA (cDNA)

(vi) ORIGINAL SOURCE:
        (A) ORGANISM: Conus quercinus (ix) FEATURE:
        (A) NAME/KEY: CDS
        (B) LOCATION: 1..285

(xi) SEQUENCE DESCRIPTION: SEQ ID NO: 65:

TAT CTG CTG GTG CCC CTG GTG GCC TTC CAC CTA ATC CTA GGC ACG GGC      48
Tyr Leu Leu Val Pro Leu Val Ala Phe His Leu Ile Leu Gly Thr Gly
 1               5                  10                  15

ACG CTA GCT CAT GGA GAC GCA CGG ACT GAA CGC CGT TCG GCT GAC GCC      96
Thr Leu Ala His Gly Asp Ala Arg Thr Glu Arg Arg Ser Ala Asp Ala
             20                  25                  30

ACA GCG CTG AAA CCT GAG CCT GTC CTC CTG CAG AAA TCC GCT GCC CGC     144
Thr Ala Leu Lys Pro Glu Pro Val Leu Leu Gln Lys Ser Ala Ala Arg
         35                  40                  45

AGC ACT GAC GAC AAT GAC AGG GAC AGG TTG ACT CAG ATG AAG AGG ATT     192
Ser Thr Asp Asp Asn Asp Arg Asp Arg Leu Thr Gln Met Lys Arg Ile
 50                  55                  60

CTC AAA AAG CGA GGA AAC ACG GCC AGA GGC TAC GAA GAA GAT AGA GAG     240
Leu Lys Lys Arg Gly Asn Thr Ala Arg Gly Tyr Glu Glu Asp Arg Glu
 65                  70                  75                  80

GTT GCG GAG ACT GTC AGA GAA CTC GAC GCA GCA GGA AAA AGA AAA          285
Val Ala Glu Thr Val Arg Glu Leu Asp Ala Ala Gly Lys Arg Lys
             85                  90                  95

TGATTAATCA AGCTGGGTGT TCCACTTGAC ACTCGTCAGT TCTAAAGTCA CCAGATAGAT    345

CGTTCCCTGT TTTTGCCCGT TTTTTCTCTT TCACTTTTCA TTTAA                   390

(2) INFORMATION FOR SEQ ID NO: 66:

(i) SEQUENCE CHARACTERISTICS:
        (A) LENGTH: 95 amino acids
        (B) TYPE: amino acid (D) TOPOLOGY: linear (ii) MOLECULE TYPE: protein (xi) SEQUENCE DESCRIPTION: SEQ ID NO: 66:

Tyr Leu Leu Val Pro Leu Val Ala Phe His Leu Ile Leu Gly Thr Gly
 1               5                  10                  15

Thr Leu Ala His Gly Asp Ala Arg Thr Glu Arg Arg Ser Ala Asp Ala
            20                  25                  30

Thr Ala Leu Lys Pro Glu Pro Val Leu Leu Gln Lys Ser Ala Ala Arg
        35                  40                  45

Ser Thr Asp Asp Asn Asp Arg Asp Arg Leu Thr Gln Met Lys Arg Ile
    50                  55                  60

Leu Lys Lys Arg Gly Asn Thr Ala Arg Gly Tyr Glu Glu Asp Arg Glu
 65                  70                  75                  80

Val Ala Glu Thr Val Arg Glu Leu Asp Ala Ala Gly Lys Arg Lys
                85                  90                  95

(2) INFORMATION FOR SEQ ID NO: 67:

(i) SEQUENCE CHARACTERISTICS:
        (A) LENGTH: 16 amino acids
        (B) TYPE: amino acid
        (C) STRANDEDNESS: <Unknown>
        (D) TOPOLOGY: linear (ii) MOLECULE TYPE: peptide (v) FRAGMENT TYPE: N-terminal (ix) FEATURE:
        (A) NAME/KEY: Modified-site
        (B) LOCATION: 2
        (D) OTHER INFORMATION: /note= "Xaa is His or Gln"

(ix) FEATURE:
        (A) NAME/KEY: Modified-site
        (B) LOCATION: 12
        (D) OTHER INFORMATION: /note= "Xaa is Pro or Ser"

(ix) FEATURE:
        (A) NAME/KEY: Modified-site
        (B) LOCATION: 15
        (D) OTHER INFORMATION: /note= "Xaa is Thr or Ala"

(ix) FEATURE:
        (A) NAME/KEY: Modified-site
        (B) LOCATION: 16
        (D) OTHER INFORMATION: /note= "Xaa is Leu or Phe"

(xi) SEQUENCE DESCRIPTION: SEQ ID NO: 67:

Met Xaa Leu Tyr Thr Tyr Leu Tyr Leu Leu Val Xaa Leu Val Xaa Xa
 1               5                  10                  15

(2) INFORMATION FOR SEQ ID NO: 68:

(i) SEQUENCE CHARACTERISTICS:
        (A) LENGTH: 17 amino acids
        (B) TYPE: amino acid
        (C) STRANDEDNESS: <Unknown>
        (D) TOPOLOGY: linear (ii) MOLECULE TYPE: peptide (vi) ORIGINAL SOURCE:
        (A) ORGANISM: Conus caracteristicus (ix) FEATURE:
        (A) NAME/KEY: Modified-site
        (B) LOCATION: 10..16

(D) OTHER INFORMATION: /note= "Xaa at residues 10, 12, 13 and
                16 may be any amino acid, but is preferably
                gamma-carboxyglutamic acid"

(xi) SEQUENCE DESCRIPTION: SEQ ID NO: 68:

Gly Asn Asp Val Asp Arg Lys Leu Ala Xaa Leu Xaa Xaa Leu Tyr Xa
1               5                   10                  15

Ile (2) INFORMATION FOR SEQ ID NO: 69

(i) SEQUENCE CHARACTERISTICS:
        (A) LENGTH: 4 amino acids
        (B) TYPE: amino acid
        (C) STRANDEDNESS: <Unknown>
        (D) TOPOLOGY: linear (ii) MOLECULE TYPE: peptide (v) FRAGMENT TYPE: N-terminal (xi) SEQUENCE DESCRIPTION: SEQ ID NO: 69:

Gly Asn Asp Val
1

(2) INFORMATION FOR SEQ ID NO: 70:

(i) SEQUENCE CHARACTERISTICS:
        (A) LENGTH: 6 amino acids
        (B) TYPE: amino acid
        (C) STRANDEDNESS: <Unknown>
        (D) TOPOLOGY: linear (ii) MOLECULE TYPE: peptide (v) FRAGMENT TYPE: internal (ix) FEATURE:
        (A) NAME/KEY: Modified-site
        (B) LOCATION: 6
        (D) OTHER INFORMATION: /note= "Xaa is
            gamma-carboxyglutamic acid"

(xi) SEQUENCE DESCRIPTION: SEQ ID NO: 70:

Asp Arg Lys Leu Ala Xaa
1               5

(2) INFORMATION FOR SEQ ID NO: 71:

(i) SEQUENCE CHARACTERISTICS:
        (A) LENGTH: 4 amino acids
        (B) TYPE: amino acid
        (C) STRANDEDNESS: <Unknown>
        (D) TOPOLOGY: linear (ii) MOLECULE TYPE: peptide (v) FRAGMENT TYPE: C-terminal (ix) FEATURE:
        (A) NAME/KEY: Modified-site
        (B) LOCATION: 6
        (D) OTHER INFORMATION: /note= "Xaa is
            gamma-carboxyglutamic acid"

(xi) SEQUENCE DESCRIPTION: SEQ ID NO: 71:

Leu Tyr Xaa Ile
1

CONANTOKINS

CROSS-REFERENCE TO RELATED APPLICATIONS

The present application is a 35 U.S.C. §371 of PCT/US/97/12618 filed on Jul. 21, 1997, which is a continuation-in-part application of U.S. patent application Ser. No. 08/684,742 filed on Jul. 22, 1996 now abandoned.

This invention was made with Government support under Grant No. PO1 GM48677 awarded by the National Institute of General Medical Sciences, National Institutes of Health, Bethesda, Md. The United States Government has certain rights in the invention.

BACKGROUND OF THE INVENTION

The invention relates to relatively short peptides (termed conantokins herein), about 10–30 residues in length, which are naturally available in minute amounts in the venom of the cone snails or analogous to the naturally available-peptides, and which include preferably one to two or more γ-carboxyglutamic acid residues. The conantokins are useful for the treatment of neurologic and psychiatric disorders, such as anticonvulsant agents, as neuroprotective agents or for the management of pain.

The publications and other materials used herein to illuminate the background of the invention, and in particular, cases to provide additional details respecting the practice, are incorporated by reference, and for convenience are referenced in the following text by author and date and are listed alphabetically by author in the appended bibliography.

The predatory cone snails (Conus) have developed a unique biological strategy. Their venom contains relatively small peptides that are targeted to various neuromuscular receptors and may be equivalent in their pharmacological diversity to the alkaloids of plants or secondary metabolites of microorganisms. Many of these peptides are among the smallest nucleic acid-encoded translation products having defined conformations, and as such, they are somewhat unusual. Peptides in this size range normally equilibrate among many conformations. Proteins having a fixed conformation are generally much larger.

The cone snails that produce these peptides are a large genus of venomous gastropods comprising approximately 500 species. All cone snail species are predators that inject venom to capture prey, and the spectrum of animals that the genus as a whole can envenomate is broad. A wide variety of hunting strategies are used, however, every Conus species uses fundamentally the same basic pattern of envenomation.

Several peptides isolated from Conus venoms have been characterized. These include the α-, μ- and ω-conotoxins which target nicotinic acetylcholine receptors, muscle sodium channels, and neuronal calcium channels, respectively (Olivera et al., 1985). Conopressins, which are vasopressin analogs, have also been identified (Cruz et al., 1987). In addition, peptides named conantokins have been isolated from *Conus geographuis* and *Conus tulipa* (Mena et al., 1990; Haack et al., 1990). These peptides have unusual age-dependent physiological effects: they induce a sleep-like state in mice younger than two weeks and hyperactive behavior in mice older than 3 weeks (Haack et al., 1990).

The conantokins are structurally unique. In contrast to the well characterized conotoxins from Conus venoms, most conantokins do not contain disulfide bonds. However, they contain 4–5 residues of the unusual modified amino acid γ-carboxyglutamic acid. The occurrence of this modified amino acid, which is derived post-translationally from glutamate in a vitamin K-dependent reaction, was unprecedented in a neuropeptide. It has been established that the conantokins have N-methyl-D-aspartate (NMDA) antagonist activity, and consequently target the NMDA receptor. The conantokins reduce glutamate (or NMDA) mediated increases in intracellular $Ca^{2+}$ and cGMP without affecting kainate-mediated events (Chandler et al., 1993). Although these peptides have actions through polyamine responses of the NMDA receptors, the neurochemical profile of these polypeptides is distinct from previously described noncompetitive NMDA antagonists (Skolnick et al., 1992).

The previously identified conantokins are Conantokin G (Con G) and Conantokin T (Con T). Con G has the formula Gly-Glu-$Xaa_1$-$Xaa_1$-Leu-Gln-$Xaa_2$-Asn-Gln-$Xaa_2$-Leu-Ile-Arg-$Xaa_2$-Lys-Ser-Asn (SEQ ID NO:1), wherein $Xaa_1$ and $Xaa_2$ are γ-carboxyglutamic acid (Gla). The C-terminus preferably contains an amide group. Con T has the formula Gly-Glu-$Xaa_1$-$Xaa_1$-Tyr-Gln-Lys-Met-Leu-$Xaa_2$-Asn-Leu-Arg-$Xaa_2$-Ala-Glu-Val-Lys-Lys-Asn-Ala (SEQ ID NO:2), wherein $Xaa_1$ and $Xaa_2$ are γ-carboxyglutamic acid. The C-terminus preferably contains an amide group. Analogues of Conantokin G have been synthesized and analyzed for their biological activity (Chandler et al., 1993; Zhou et al., 1996). It has been discovered that substitution of the Gla residue at position 4 of Con G destroys its NMDA antagonist properties. Substitution of the Gla residue at position 3 of Con G greatly reduces its NMDA antagonist activity. However, substitutions of the Gla residues at positions 7, 10 and 14 of Con G do not adversely affect potency of the peptide and may even enhance it. (Zhou et al., 1996).

Ischemic damage to the central nervous system (CNS) may result form either global or focal ischemic conditions. Global ischemia occurs under conditions in which blood flow to the entire brain ceases for a period of time, such as may result from cardiac arrest. Focal ischemia occurs under conditions in which a portion of the brain is deprived of its normal blood supply, such as may result from thromboembolytic occlusion of a cerebral vessel, traumatic head or spinal cord injury, edema or brain or spinal cord tumors. Both global and focal ischemic conditions have the potential for widespread neuronal damage, even if the global ischemic condition is transient or the focal condition affects a very limited area.

Epilepsy is a recurrent paroxysmal disorder of cerebral function characterized by sudden brief attacks of altered consciousness, motor activity, sensory phenomena or inappropriate behavior caused by abnormal excessive discharge of cerebral neurons. Convulsive seizures, the most common form of attacks, begin with loss of consciousness and motor control, and tonic or clonic jerking of all extremities but any recurrent seizure pattern may be termed epilepsy. The term primary or idiopathic epilepsy denotes those cases where no cause for the seizures can be identified. Secondary or symptomatic epilepsy designates the disorder when it is associated with such factors as trauma, neoplasm, infection, developmental abnormalities, cerebrovascular disease, or various metabolic conditions. Epileptic seizures are classified as partial seizures (focal, local seizures) or generalized seizures (convulsive or nonconvulsive). Classes of partial seizures include simple partial seizures, complex partial seizures and partial seizures secondarily generalized. Classes of generalized seizures include absence seizures, atypical absence seizures, myoclonic seizures, clonic seizures, tonic seizures, tonic-clonic seizures (grand mal) and atonic seizures. Therapeutics having anticonvulsant properties are used in the treatment of seizures. Most therapeutics used to abolish or attenuate seizures act at least through effects that reduce the spread of excitation from seizure foci and prevent detonation and disruption of function of normal aggregates of neurons. Traditional anticonvulsants that have been utilized include phenytoin, phenobarbital, primidone, carbamazepine, ethosuximide, clonazepam and valproate. Several novel and chemically diverse anticonvulsant medications recently have been approved for marketing, including lamotrigine, feribamate, gabapentin and topiramate. For further details of seizures and their therapy, see Rall & Schleifer (1985) and *The Merck Manual* (1992).

It has been shown that neurotransmission mediated through the NMDA receptor complex is associated with seizures (Bowyer, 1982; McNamara et al., 1988), ischemic neuronal injury (Simon et al., 1984; Park et al., 1988) and other phenomena including synaptogenesis (Cline et al., 1987), spatial learning (Morris et al., 1986) and long-term potentiation (Collinridge et al., 1983; Harris et al., 1984; Morris et al., 1986). Regulation of these neuronal mechanisms by NMDA-mediated processes may involve activation of a receptor-gated calcium ion channel (Nowak et al., 1984; Mayer et al., 1987; Ascher and Nowak, 1988).

The NMDA channel is regulated by glycine. This amino acid increases NMDA-evoked currents in various tissues [Johnson and Ascher, 1987; Kleckner and Dingledine, 1988] by increasing the opening frequency of the NMDA channel [Johnson and Ascher, 1987]. Thus, NMDA-induced calcium influx and intracellular accumulation may be stimulated by glycine [Reynolds et al., 1987; Wroblewski et al., 1989], which interacts with its own distinct site [Williams et al., 1991]. Furthermore, accumulation of intracellular calcium may be implicated in the aforementioned neuropathologies.

The NMDA receptor is also involved in a broad spectrum of CNS disorders. For example, during brain ischemia caused by stroke or traumatic injury, excessive amounts of the excitatory amino acid glutamate are released from damaged or oxygen deprived neurons. This excess glutamate binds the NMDA receptor which opens the ligand-gated ion channel thereby allowing $Ca^{2+}$ influx producing a high level of intracellular $Ca^{2+}$, which activates biochemical cascades resulting in protein, DNA and membrane degradation leading to cell death. This phenomenon, known as excitotoxicity, is also thought to be responsible for the neurological damage associated with other disorders ranging from hypoglycemia and cardiac arrest to epilepsy. In addition, there are reports indicating similar involvement in the chronic neurodegeneration of Huntington's, Parkinson's and Alzheimer's diseases.

Parkinson's disease is a progressive, neurodegenerative disorder. The etiology of the disorder is unknown in most cases, but has been hypothesized to involve oxidative stress. The underlying neuropathology in Parkinsonian patients is an extensive degenerations of the pigmented dopamine neurons in the substantia nigra. These neurons normally innervate the caudate and putamen nuclei. Their degeneration results in a marked loss of the neurotransmitter dopamine in the caudate and putamen nuclei. This loss of dopamine and its regulation of neurons in the caudate-putamen leads to the bradykinesia, rigidity, and tremor that are the hallmarks of Parkinson's disease. An animal model has been developed for Parkinson's disease (Zigmond et al., 1987) and has been used to test agents for anti-Parkinsonian activity (Ungerstedt et al., 1973).

The dopamine precursor, L-Dopa, is the current therapy of choice in treating the symptoms of Parkinson's disease. However, significant side effects develop with continued use of this drug and with disease progression, making the development of novel therapies important. Recently, antagonists of the NMDA subtype of glutamate receptor have been proposed as potential anti-Parkinsonian agents. (Borman, 1989; Greenamyre and O'Brien, 1991; Olney et al., 1987). In addition, antagonists of NMDA receptors potentiate the behavioral effects of L-Dopa and D1 dopamine receptor stimulation in animal models of Parkinson's disease. (Starr, 1995). These data suggest that NMDA receptor antagonists may be useful adjuncts to L-Dopa therapy in Parkinson's disease by decreasing the amount of L-Dopa required and thereby reducing undesirable side effects. In addition, antagonists of NMDA receptors have been shown to attenuate free radical mediated neuronal death. Thus, NMDA receptor antagonists may also prevent further degeneration of dopamine neurons in addition to providing symptomatic relief. Finally, NMDA receptor antagonists have been shown to potentiate the contralateral rotations induced by L-Dopa or D1 dopamine receptor antagonists in the animal model.

Pain, and particularly, persistent pain, is a complex phenomenon involving many interacting components. Numerous studies, however, have demonstrated a role for NMDA receptors in mediating persistent pain, and further that NMDA antagonists are effective in animal models of persistent pain. First, administration of NMDA (the agonist) mimics many of the physiological and behavioral effects of painful stimuli (Chapman et al., 1994; Dougherty and Willis, 1991; Coderre and Melzack, 1992; Malmberg and Yaksh, 1992; Bach et al., 1994; Liu et al., 1997). Second, various classes of NMDA antagonists block the "wind up" (progressive augmentation of response caused by repetitive stimulation) of small primary afferent C fibers of the dorsal horn (Davies and Lodge, 1987; Dickenson and Sullivan, 1987; Thompson et al., 1990). Third, release of glutamate and aspartate (agonists at NMDA and non-NMDA glutamatergic receptors) is increased in spinal cord in animal models of persistent pain (Sluka and Westlund, 1992; Malmberg and Yaksh, 1992; Yang et al., 1995). Fourth, NMDA antagonists are effective in animal models of persistent pain (Neugebauer et al., 1993; Coderre, 1993; Coderre and Van Empel, 1994; Yamamoto and Yaksh, 1992; Chaplan et al., 1997; Millan and Seguin, 1994; Rice and McMahon, 1994). Moreover, NMDA antagonists appear to be effective in reducing the tolerance to opioid analgesics seen after chronic administration in animal models of pain (Bilsky et al., 1996; Lufty et al., 1996; Shimoyama et al., 1996; Wong et al., 1996; Elliot et al., 1994; Mao et al., 1994; Dunbar and Yaksh, 1996; Lufty et al., 1995; Trujillo and Akil, 1994; Tiseo et al., 1994; Gutstein and Trujillo, 1993; Kest et al., 1993; Tiseo and Inturrisi, 1993). Finally, severe or prolonged tissue or nerve injury can induce hyperexcitability of dorsal horn neurons of the spinal cord, resulting in persistent pain, an exacerbated response to noxious stimuli (hyperalgesia) and a lowered pain threshold (allodynia). These changes are mediated by NMDA-type glutamate receptors in the spinal cord, whose activation causes release of Substance P, a peptide neurotransmitter made by small-diameter, primary, sensory pain fibres. Injection of NMDA in the cerebrospinal fluid of the rat spinal cord mimicked the changes that occur with persistent injury and produced pain (Liu et al., 1997).

Neuropsychiatric involvement of the NMDA receptor has also been recognized. Blockage of the NMDA receptor Ca2+ channel by the animal anesthetic phencyclidine produces a psychotic state in humans similar to schizophrenia (Johnson et al., 1990). Further, NMDA receptors have also been implicated in certain types of spatial learning (Bliss et al., 1993). In addition, numerous studies have demonstrated a role for NMDA receptors in phenomena associated with addiction to and compulsive use of drugs or ethanol. Furthermore, antagonists of NMDA receptors may be useful for treating addiction-related phenomena such as tolerance, sensitization, physical dependence and craving (for review see, Popik et al., 1995; Spanagel and Zieglgansberger, 1997; Trujillo and Akil, 1995).

There are several lines of evidence which suggest that NMDA antagonists may be useful in the treatment of HIV infection. First, the levels of the neurotoxin and NMDA agonist quinolinic acid are elevated in the cerebrospinal fluid of HIV-positive subjects (Heyes et al., 1989) and in murine retrovirus-induced immunodeficiency syndrome (Sei et al., 1996). Second, the envelope glycoprotein of HIV-1 alters NMDA receptor function (Sweetnam et al., 1993). Thirdly, NMDA antagonists can reduce the effects and neurotoxicity of GP-120 (Muller et al., 1996; Raber et al., 1996; Nishida et al., 1996). Fourth, GP-120 and glutamate act synergistically to produce toxicity in vitro (Lipton et al., 1991). And finally, memantine, an NMDA antagonist, protects against HIV infection in glial cells in vitro (Rytik et al., 1991). For a review of the use of NMDA antagonists in treating HIV infection, see Lipton (1994; 1996).

It is desired to identify additional conantokin peptides and related compounds which target the NMDA receptor. It is further desired to identify compounds which are useful as anticonvulsant, neuroprotective, neuropsychiatric or analgesic agents.

SUMMARY OF THE INVENTION

The present invention is directed to conantokin peptides, conantokin peptide derivatives and conantokin peptide chimeras, referred to collectively as conantokins (unless the context dictates otherwise), having 10–30 amino acids, including preferably one to two or more γ-carboxyglutamic acid residues. The conantokins are useful for the treatment of neurologic or psychiatric disorders, such as anticonvulsant agents, as neuroprotective agents or for the management of pain. The conantokins are administered to patients as described further below.

More specifically, the present invention is directed to conantokin peptides, which include but are not limited to, G, T, L, R, S1, Oc, Gm, Ca2, Ca1 and Qu. Conantokin G (Con G) has the formula Gly-Glu-$Xaa_1$-$Xaa_1$-Leu-Gln-$Xaa_2$-Asn-Gln-$Xaa_2$-Leu-Ile-Arg-$Xaa_2$-Lys-Ser-Asn (SEQ ID NO:1), wherein $Xaa_1$ and $Xaa_2$ are preferably γ-carboxyglutamic acid (Gla). The C-terminus contains a carboxyl or an amide, preferably an amide group. Conantokin T (Con T) has the formula Gly-Glu-$Xaa_1$-$Xaa_1$-Tyr-Gln-Lys-Met-Leu-$Xaa_2$-Asn-Leu-Arg-$Xaa_2$-Ala-Glu-Val-Lys-Lys-Asn-Ala (SEQ ID NO:2), wherein $Xaa_1$ and $Xaa_2$ are preferably γ-carboxyglutamic acid. The C-terminus contains a carboxyl or an amide, preferably an amide group. Conatokin L (Con L), has the formula Gly-Glu-$Xaa_1$-$Xaa_1$-Val-Ala-Lys-Met-Ala-Ala-$Xaa_2$-Leu-Ala-Arg-$Xaa_2$-Asp-Ala-Val-Asn (SEQ ID NO:3), wherein $Xaa_1$ and $Xaa_2$ are preferably γ-carboxyglutamic acid. The C-terminus contains a carboxyl or an amide, preferably an amide group. Conantokin R (Con R) has the formula: Gly-Glu-$Xaa_1$-$Xaa_1$-Val-Ala-Lys-Met-Ala-Ala-$Xaa_2$-Leu-Ala-Arg-$Xaa_2$-Asn-Ile-Ala-Lys-Gly-Cys-Lys-Val-Asn-Cys-Tyr-Pro (SEQ ID NO:4), wherein $Xaa_1$ and $Xaa_2$ are preferably γ-carboxyglutamic acid. The C-terminus contains a carboxyl or an amide, preferably a carboxyl group. The cysteine residues form a disulfide bridge. Conantokin S1 (Con S1) has the formula: Gly-Asp-$Xaa_1$-$Xaa_1$-Tyr-Ser-Lys-Phe-Ile-$Xaa_2$-Arg-Glu-Arg-$Xaa_2$-Ala-Gly-Arg-Leu-Asp-Leu-Ser-Lys-Phe-Pro (SEQ ID NO:5), wherein $Xaa_1$ and $Xaa_2$ are preferably γ-carboxyglutamic acid. The C-terminus contains a carboxyl or amide, preferably a carboxyl group. Conantokin Oc (Con Oc) has the formula: Gly-Glu-$Xaa_1$-$Xaa_1$-Tyr-Arg-Lys-Ala-Met-Ala-$Xaa_1$-Leu-Glu-Ala-Lys-Lys-Ala-Gln-$Xaa_2$-Ala-Leu-Lys-Ala (SEQ ID NO:6), wherein $Xaa_1$ and $Xaa_2$ are preferably γ-carboxyglutamic acid. The C-terminus contains a carboxyl or amide, preferably an amide group. Conantokin Gm (Con Gm) has the formula: Gly-Ala-Lys-$Xaa_1$-Asp-Arg-Asn-Asn-Ala-$Xaa_2$-Ala-Val-Arg-$Xaa_2$-Arg-Leu-Glu-Glu-Ile(SEQIDNO:7), $Xaa_1$ and $Xaa_2$ are preferably γ-carboxyglutamic acid. The C-terminus contains a carboxyl or amide, preferably an amide group. Conantokin Ca2 (Con Ca2) has the formula: Gly-Tyr-$Xaa_1$-$Xaa_1$-Asp-Arg-$Xaa_2$-Ile-Ala-$Xaa_2$-Thr-Val-Arg-$Xaa_2$-Leu-Glu-Glu-Ala (SEQ ID NO:8), wherein $Xaa_1$ and $Xaa_2$ are preferably γ-carboxyglutamic acid. The C-terminus contains a carboxyl or amide, preferably an amide group. Conantokin Qu (Con Qu) has the formula: Gly-Tyr-$Xaa_1$-$Xaa_1$-Asp-Arg-$Xaa_2$-Val-Ala-$Xaa_2$-Thr-Val-Arg-$Xaa_2$-Leu-Asp-Ala-Ala (SEQ ID NO:9), wherein $Xaa_1$ and $Xaa_2$ are preferably γ-carboxyglutamic acid. The C-terminus contains a carboxyl or amide, preferably an amide group. Conantokin Ca1 (Con Ca1) has the formula: Gly-Asn-Asp-Val-Asp-Arg-Lys-Leu-Ala-$Xaa_2$-Leu-$Xaa_2$-$Xaa_2$-Leu-Tyr-$Xaa_2$-Ile (SEQ ID NO:68), wherein $Xaa_2$ is preferably γ-carboxyglutamic acid. The C-terminus contains a carboxyl or amide, preferably an amide group.

The present invention is also directed to conantokin peptide derivatives. Examples of conantokin peptide derivatives include conantokin peptides in which the γ-carboxyglutamic acid at the $Xaa_2$ residues in these peptides is replaced by any other amino acids such that their NMDA antagonist activity is not adversely affected. Examples of such replacements include, but are not limited to Ser, Ala, Glu and Tyr. In addition, glutamic acid residues in the peptide can be modified to γ-carboxyglutamate residues. Other derivatives are produced by modification of the amino acids within the conantokin structure. Modified amino acids include those which are described in Roberts et al. (1983). Other derivatives include conantokin peptides in which one or more residues have been deleted.

The present invention is also directed to conantokin peptide chimeras. Suitable conantokin chimeras are produced by recombination of different segments of two or more conantokin peptides, conantokin peptide derivatives or a peptide encoded by exon 5 of the NMDA receptor, e.g. Lys-Pro-Gly-Arg-Lys (SEQ ID NO:10) or Lys-Pro-Gly-Arg-Lys-Asn (SEQ ID NO:11).

DETAILED DESCRIPTION OF THE PREFERRED EMBODIMENT

Figure 1:
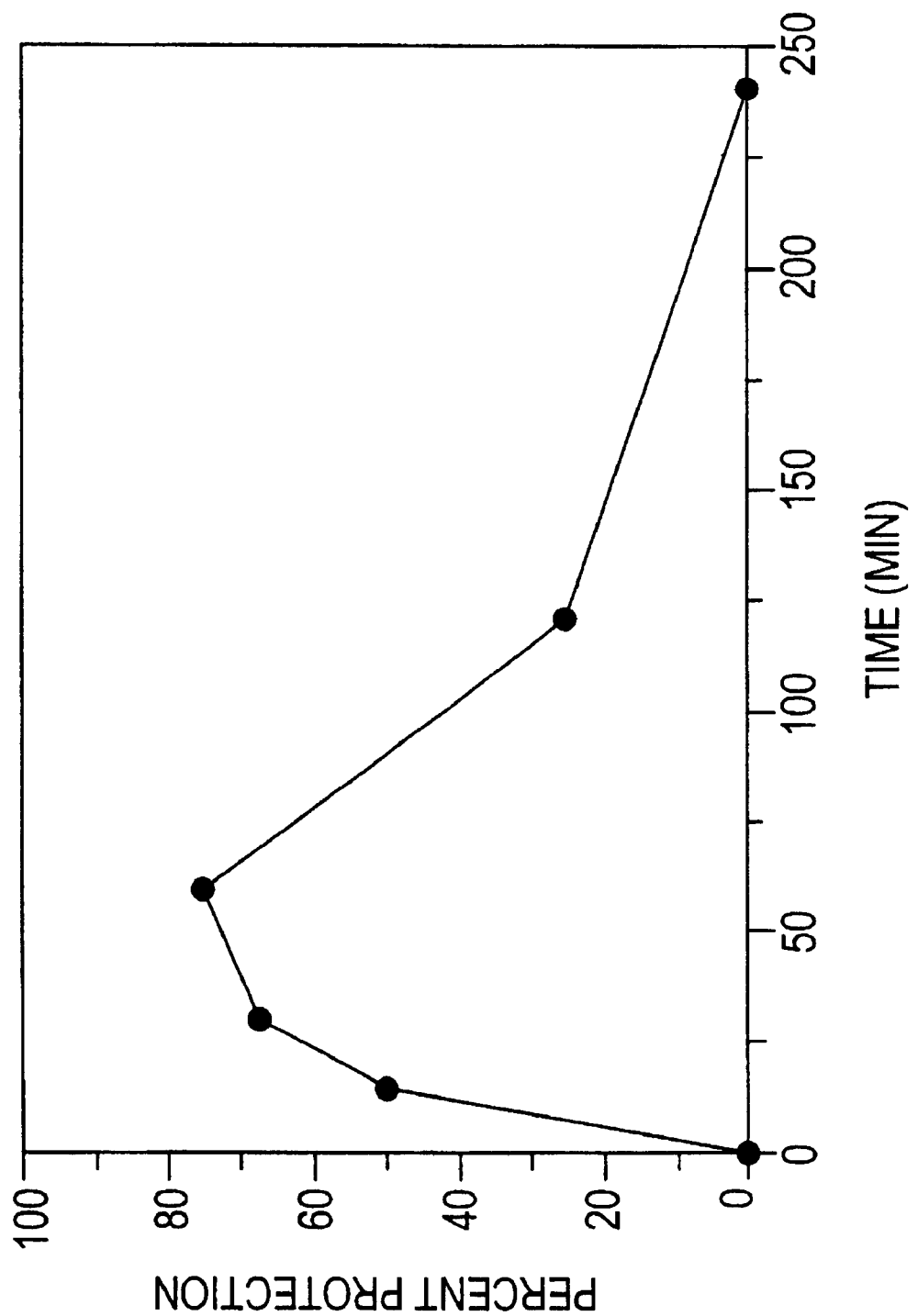
FIG. 1 shows the time-dependent inhibition of audiogenic seizures by Con R following intracerebroventricular (i.c.v.) administration to Frings audiogenic mice.

The present invention is directed to conantokin peptides, conantokin peptide derivatives and conantokin peptide chimeras, referred to collectively as conantokins (unless the context dictates otherwise), having 10–30 amino acids, including preferably one to two or more γ-carboxyglutamnic acid residues. The conantokins are useful for the treatment of neurologic and psychiatric disorders, such as anticonvulsant agents, as neuroprotective agents or for the management of pain, e.g. as analgesic agents. Neurologic disorders and psychiatric disorders as used herein are intended to include such disorders as grouped together in *The Merck Manual of Diagnosis and Therapy,* inclusive of the disorders discussed herein.

More specifically, the present invention is directed to conantokins which are useful for the treatment and alleviation of epilepsy and as a general anticonvulsant agent. The present invention is also directed to conantokins which are useful for reducing neurotoxic injury associated with conditions of hypoxia, anoxia or ischemia which typically follows stroke, cerebrovascular accident, brain or spinal cord trauma, myocardial infarct, physical trauma, drowning, suffocation, perinatal asphyxia, or hypoglycemic events. The present invention is further directed to conantokins useful for treating neurodegeneration associated with Alzheimer's disease, senile dementia, Amyotrophic Lateral Sclerosis, Multiple Sclerosis, Parkinson's disease, Huntington's disease, Down's Syndrome, Korsakoff's disease, schizophrenia, AIDS dementia, multi-infarct dementia, Binswanger dementia and neuronal damage associated with uncontrolled seizures. The present invention is also directed to conantokins which are useful for treating chemical toxicity, such as addiction, drug craving, alcohol abuse, morphine tolerance, opioid tolerance and barbiturate tolerance. The present invention is further directed to conantokins useful for treating psychiatric disorders, such as anxiety, major depression, manic-depressive illness, obsessive-compulsive disorder, schizophrenia and mood disorders (such as bipolar disorder, unipolar depression, dysthymia and seasonal effective disorder). The conantokins are also useful for treating ophthalmic disorders. The present invention is also directed to conantokins useful for treating additional neurological disorders, such as dystonia (movement disorder), sleep disorder, muscle relaxation and urinary incontinence. In addition, the conantokins are useful for memory/cognition enhancement, i.e., treating memory, learning or cognitive deficits. The present invention is also useful in the treatment of HIV infection. Finally, the present invention is directed to conantokins useful for controlling pain, e.g. as analgesic agents, and the treatment of migraine, acute pain or persistent pain. They can be used prophylactically and also to relieve the symptoms associated with a migraine episode.

The present invention is directed to conantokin peptides, which include but are not limited to G, T, L, R, S1, Oc, Gm, Ca2, Ca1 and Qu. Conantokin G (Con G) has the formula Gly-Glu-Xaa$_1$-Xaa$_1$-Leu-Gln-Xaa$_2$-Asn-Gln-Xaa$_2$-Leu-Ile-Arg-Xaa$_2$-Lys-Ser-Asn (SEQ ID NO:1), wherein Xaa$_1$ and Xaa$_2$ are preferably γ-carboxyglutamic acid (Gla). The C-terminus contains a carboxyl or an amide, preferably an amide group. Conantokin T (Con T) has the formula Gly-Glu-Xaa$_1$-Xaa$_1$-Tyr-Gln-Lys-Met-Leu-Xaa$_2$-Asn-Leu-Arg-Xaa$_2$-Ala-Glu-Val-Lys-Lys-Asn-Ala (SEQ ID NO:2), wherein Xaa$_1$ and Xaa$_2$ are preferably γ-carboxyglutamic acid. The C-termninus contains a carboxyl or an aamide, preferably an amide group. Conatokin L (Con L), has the formula Gly-Glu-Xaa$_1$-Xaa$_1$-Val-Ala-Lys-Met-Ala-Ala-Xaa$_2$-Leu-Ala-Arg-Xaa$_1$-Asp-Ala-Val-Asn (SEQ ID NO:3), wherein Xaa$_1$ and Xaa$_2$ are preferably γ-carboxyglutamic acid. The C-terminus contains a carboxyl or an amide, preferably an amide group. Conantokin R (Con R) has the formula: Gly-Glu-Xaa$_1$-Xaa$_1$-Val-Ala-Lys-Met-Ala-Ala-Xaa$_2$-Leu-Ala-Arg-Xaa$_2$-Asn-Ile-Ala-Lys-Gly-Cys-Lys-Val-Asn-Cys-Tyr-Pro (SEQ ID NO:4), wherein Xaa$_1$ and Xaa$_2$ are preferably γ-carboxyglutamic acid. The C-terminus contains a carboxyl or an amide, preferably a carboxyl group. The cysteine residues form a disulfide bridge. Conantokin S1 (Con S1) has the formula: Gly-Asp-Xaa$_1$-Xaa$_1$-Tyr-Ser-Lys-Phe-Ile-Xaa$_2$-Arg-Glu-Arg-Xaa$_2$-Ala-Gly-Arg-Leu-Asp-Leu-Ser-Lys-Phe-Pro (SEQ ID NO:5), wherein Xaa$_1$ and Xaa$_2$ are preferably γ-carboxyglutamic acid. The C-terminus contains a carboxyl or amide, preferably a carboxyl group. Conantokin Oc (Con Oc) has the formula: Gly-Glu-Xaa$_1$-Xaa$_1$-Tyr-Arg-Lys-Ala-Met-Ala-Xaa$_2$-Leu-Glu-Ala-Lys-Lys-Ala-Gln-Xaa$_2$-Ala-Leu-Lys-Ala (SEQ ID NO:6), wherein Xaa$_1$ and Xaa$_2$ are preferably γ-carboxyglutamic acid. The C-terminus contains a carboxyl or amide, preferably an amide group. Conantokin Gm (Con Gm) has the formula: Gly-Ala-Lys-Xaa$_1$-Asp-Arg-Asn-Asn-Ala-Xaa$_2$-Ala-Val-Arg-Xaa$_2$-Arg-Leu-Glu-Glu-Ile (SEQ ID NO:7), wherein Xaa$_1$ and Xaa$_2$ are preferably γ-carboxyglutamic acid. The C-terminus contains a carboxyl or amide, preferably an amide group. Conantokin Ca2 (Con Ca2) has the formula: Gly-Tyr-Xaa$_1$-Xaa$_1$-Asp-Arg-Xaa$_2$-Ile-Ala-Xaa$_2$-Thr-Val-Arg-Xaa$_2$-Leu-Glu-Glu-Ala (SEQ ID NO:8), wherein Xaa$_1$ and Xaa$_2$ are preferably γ-carboxyglutamic acid. The C-terminus contains a carboxyl or amide, preferably an amide group. Conantokin Qu (Con Qu) has the formula: Gly-Tyr-Xaa$_1$-Xaa$_1$-Asp-Arg-Xaa$_2$-Val-Ala-Xaa$_2$-Thr-Val-Arg-Xaa$_2$-Leu-Asp-Ala-Ala (SEQ ID NO:9), wherein Xaa$_1$ and Xaa$_2$ are preferably γ-carboxyglutamic acid. The C-terminus contains a carboxyl or amide, preferably an amide group. Conantokin Ca1 (Con Ca1) has the formula: Gly-Asn-Asp-Val-Asp-Arg-Lys-Leu-Ala-Xaa$_2$-Leu-Xaa$_2$-Xaa$_2$-Leu-Tyr-Xaa$_2$-Ile (SEQ ID NO:68), wherein Xaa$_2$ is preferably γ-carboxyglutamic acid. The C-terminus contains a carboxyl or amide, preferably an amide group.

The present invention is further directed to conantokin peptide derivatives. Examples of suitable derivatives include, but are not limited to those described herein. In one embodiment, the γ-carboxyglutamic acid at the Xaa$_2$ residues in the above peptides may be replaced by any other amino acids without adversely affecting their NMDA antagonist activity. Examples of such amino acid replacements include, but are not limited to, Ser, Ala, Glu and Tyr. In addition, glutamic acid residues in the peptide can be modified to γ-carboxyglutamate residues. Substitutions of one amino acid for another can be made at one or more additional sites within the above conantokin peptides, and may be made to modulate one or more of the properties of the peptides. Substitutions of this kind are preferably conservative, i.e., one amino acid is replaced with one of similar shape and charge. Conservative substitutions are well known in the art and include, for example: alanine to serine, arginine to lysine, asparagine to glutamine or histidine, glycine to proline, leucine to valine or isoleucine, serine to threonine, phenylalanine to tyrosine, and the like. Other derivatives are produced by modification of the amino acids within the conantokin structure. Modified amino acids include those which are described in Roberts et al. (1983). Other derivatives include conantokin peptides in which one or more residues have been deleted. For example, one such derivative is conantokin G in which the five C-terminal amino acids have been deleted. The activity of such derivatives can easily be determined in assays known in the art, including but not limited to the assays disclosed herein.

Finally, the present invention is directed to conantokin peptide chimeras. Suitable conantokin peptide chimeras are produced by recombination of different segments of two or more conantokin peptides, conantokin peptide derivatives or the peptide encoded by exon 5 of the NMDA receptor, e.g. Lys-Pro-Gly-Arg-Lys (SEQ ID NO:10) or Lys-Pro-Gly-Arg-Lys-Asn (SEQ ID NO:11). The conantokin peptides and conantokin peptide derivatives can be divided into, for example, four domains as shown in Table 1. Table 1 is not meant to be exclusive and domains of conantokin peptides or conantokin peptide derivatives not set forth in Table 1 can also be easily identified. The SEQ ID NOs are in parentheses. "γ" is γ-carboxyglutamic acid.

TABLE 1

Domains of Conantokin Peptides and Derivatives

| Conantokin | I | II | III | IV |
|---|---|---|---|---|
| Con G | GEγγ (12) | LQγNQγ (13) | LIRγ (14) | KSN |
| Con T | GEγγ (12) | YQKMLγ (15) | NLRγ (16) | AEVKKNA (17) |
| Con R | GEγγ (12) | VAKMAAγ (18) | LARγ (19) | NIAKGCKVNCYP (20) |
| Con L | GEγγ (12) | VAKMAAγ (18) | LARγ (19) | DAVN (21) |
| A$^{7,10,14}$ Con G | GEγγ (12) | LQANQA (22) | LIRA (23) | KSN |
| A$^7$ Con G | GEγγ (12) | LQANQγ (24) | LIRγ (14) | KSN |
| S$^7$ Con G | GEγγ (12) | LQSNQγ (25) | LIRγ (14) | KSN |
| T$^7$ Con G | GEγγ (12) | LQTNQγ (26) | LIRγ (14) | KSN |
| Con S1 | GDγγ (27) | YSKFIγ (28) | RERγ (29) | AGRLDLSKFP (30) |
| Con Oc | GEγγ (12) | YRKAMAγ (31) | LEAKKAQγ (32) | ALKA (33) |
| Con Qu | GYγγ (34) | DRγVAγ (35) | TVRγ (36) | LDAA (37) |
| Con Ca2 | GYγγ (12) | DRγIAγ (38) | TVRγ (36) | LEEA (39) |
| Con Gm | GAKγ (40) | DRNNAγ (41) | AVRγ (42) | RLEEI (43) |
| Con Ca1 | GNDV (69) | DRKLAγ (70) | Lγγ | LYγI (71) |

The conantokin peptide chimeras are prepared by combining any one of the individual elements of each domain with any one of the elements of the other domains. Thus, conatokin peptide chimeras are prepared by combining (a) any one of domain I, (b) any one of domain II, (c) any one of domain III and (d) any one of domain IV. Additional conantokin peptide chimeras are prepared by combining domain I to the C terminal end of a peptide encoded by exon 5 of the NMDA receptor. Examples of the latter peptide include Lys-Pro-Gly-Arg-Lys (SEQ ID NO:10) and Lys-Pro-Gly-Arg-Lys-Asn (SEQ ID NO:1). The activity of such chimeras can easily be determined in assays known in the art, including but not limited to the assays disclosed herein.

In view of the definitions for conantokin peptides, conantokin peptide derivatives and conantokin peptide chimeras, a generic formula for conantokins of the present invention is derived. This generic formula is as follows:

$$(X_1)_m\text{-}G\text{-}X_2\text{-}X_3\text{-}X_4\text{-}(X_5)_n\text{-}(X_6)_p\text{-}(X_7)_q$$

wherein

X$_1$ is Lys-Pro-Gly-Arg-Lys (SEQ ID NO:10) or Lys-Pro-Gly-Arg-Lys-Asn (SEQ ID NO:11),

X$_2$ is any amino acid,

X$_3$ is any amino acid,

X$_4$ is any amino acid,

X$_5$ is a peptide having 1–7 amino acid residues,

X$_6$ is a peptide having 1–4 amino acid residues,

X$_7$ is a peptide having 1–12 amino acid residues, m, n, p, and q are independently 0 or 1, with the proviso that when m is 1, then n, p and q are each 0.

It is preferred that X$_2$ is Glu, Asp, Tyr, Ala or Asn, X$_3$ is Lys, Glu, Gla, Asp, Tyr, Ala, Ser or phosphoserine, X$_4$ is Glu, Gla, Asp, Ala, Ser or phosphoserine and n is 1. More preferably, X$_4$ is Gla, and most preferably, X$_3$ and X$_4$ are each Gla.

The conantokin peptides, conantokin peptide derivatives, conantokin peptide chimeras and conantokins of the generic formula above, collectively referred to as conantokins, have anticonvulsant activity in Frings audiogenic seizure susceptible mice and in syndrome-specific seizure animal models. These conantokins also have activity in animal pain models. These conantokins further have activity in in vitro assays for protection from neurotoxicity. These conantokins also have activity in animal models for Parkinson's disease. Thus, the conantokins of the present invention are useful as anticonvulsant agents, as neuroprotective agents, as analgesic agents, for managing pain and for treating neurodegenerative disorders. The conantokins of the present inventions are particularly useful as such agents for treating neurologic disorders and psychiatric disorders that result from an overstimulation of excitatory amino acid receptors. That is, the invention pertains to disorders in which the pathophysiology involves excessive excitation of nerve cells by excitatory amino acids or agonists of the NMDA receptor(s). The conantokins are administered to patients as described further below.

These peptides, derivatives and chimeras are sufficiently small to be chemically synthesized. General chemical syntheses for preparing the foregoing conantokin peptides, conantokin peptide derivatives and conantokin peptide chimeras are described hereinafter, along with specific chemical synthesis of one conantokin peptide and indications of biological activities of these synthetic products. Various ones of the conantokin peptides can also be obtained by isolation and purification from specific Conus species using the technique described in U.S. Pat. No. 4,447,356 (Olivera et al., 1984), the disclosure of which is incorporated herein by reference.

Although the conantokin peptides of the present invention can be obtained by purification from cone snails, because the amounts of conantokin peptides obtainable from individual snails are very small, the desired substantially pure conantokin peptides are best practically obtained in commercially valuable amounts by chemical synthesis using solid-phase strategy. For example, the yield from a single cone snail may be about 10 micrograms or less of conantokin peptide. By "substantially pure" is meant that the peptide is present in the substantial absence of other biological molecules of the same type; it is preferably present in an amount of at least about 85% purity and preferably at least about 95% purity. Chemical synthesis of biologically active conantokin peptides depends of course upon correct determination of the amino acid sequence.

The conantokin peptides can also be produced by recombinant DNA techniques well known in the art. Such techniques are described by Sambrook et al. (1979). The peptides produced in this manner are isolated, reduced if necessary, and oxidized to form the correct disulfide bonds.

One method of forming disulfide bonds in the conantokin peptides of the present invention is the air oxidation of the linear peptides for prolonged periods under cold room temperatures or at room temperature. This procedure results in the creation of a substantial amount of the bioactive, disulfide-linked peptides. The oxidized peptides are fractionated using reverse-phase high performance liquid chromatography (HPLC) or the like, to separate peptides having different linked configurations. Thereafter, either by comparing these fractions with the elution of the native material or by using a simple assay, the particular fraction having the correct linkage for maximum biological potency is easily determined. However, because of the dilution resulting from the presence of other fractions of less biopotency, a somewhat higher dosage may be required.

The peptides are synthesized by a suitable method, such as by exclusively solid-phase techniques, by partial solid-phase techniques, by fragment condensation or by classical solution couplings.

In conventional solution phase peptide synthesis, the peptide chain can be prepared by a series of coupling reactions in which constituent amino acids are added to the growing peptide chain in the desired sequence. Use of various coupling reagents, e.g., dicyclohexylcarbodiimide or diisopropylcarbonyldimidazole, various active esters, e.g., esters of N-hydroxyphthalimide or N-hydroxy-succinimide, and the various cleavage reagents, to carry out reaction in solution, with subsequent isolation and purification of intermediates, is well known classical peptide methodology. Classical solution synthesis is described in detail in the treatise, "Methoden der Organischen Chemie (Houben-Weyl): Synthese von Peptiden," (1974). Techniques of exclusively solid-phase synthesis are set forth in the textbook, "Solid-Phase Peptide Synthesis," (Stewart and Young, 1969), and are exemplified by the disclosure of U.S. Pat. No. 4,105,603 (Vale et al., 1978). The fragment condensation method of synthesis is exemplified in U.S. Pat. No. 3,972,859 (1976). Other available syntheses are exemplified by U.S. Pat. No. 3,842,067 (1974) and U.S. Pat. No. 3,862,925 (1975). The synthesis of peptides containing γ-carboxyglutamic acid residues is exemplified by Rivier et al. (1987), Nishiuchi et al. (1993) and Zhou et al. (1996).

Common to such chemical syntheses is the protection of the labile side chain groups of the various amino acid moieties with suitable protecting groups which will prevent a chemical reaction from occurring at that site until the group is ultimately removed. Usually also common is the protection of an α-amino group on an amino acid or a fragment while that entity reacts at the carboxyl group, followed by the selective removal of the α-amino protecting group to allow subsequent reaction to take place at that location. Accordingly, it is common that, as a step in such a synthesis, an intermediate compound is produced which includes each of the amino acid residues located in its desired sequence in the peptide chain with appropriate side-chain protecting groups linked to various ones of the residues having labile side chains.

As far as the selection of a side chain amino protecting group is concerned, generally one is chosen which is not removed during deprotection of the α-amino groups during the synthesis. However, for some amino acids, e.g., His, protection is not generally necessary. In selecting a particular side chain protecting group to be used in the synthesis of the peptides, the following general rules are followed: (a) the protecting group preferably retains its protecting properties and is not split off under coupling conditions, (b) the protecting group should be stable under the reaction conditions selected for removing the α-amino protecting group at each step of the synthesis, and (c) the side chain protecting group must be removable, upon the completion of the synthesis containing the desired amino acid sequence, under reaction conditions that will not undesirably alter the peptide chain.

It should be possible to prepare many, or even all, of these peptides using recombinant DNA technology. However, when peptides are not so prepared, they are preferably prepared using the Merrifield solid-phase synthesis, although other equivalent chemical syntheses known in the art can also be used as previously mentioned. Solid-phase synthesis is commenced from the C-terminus of the peptide by coupling a protected α-amino acid to a suitable resin. Such a starting material can be prepared by attaching an α-amino-protected amino acid by an ester linkage to a chloromethylated resin or a hydroxymethyl resin, or by an amide bond to a benzhydrylamine (BHA) resin or paramethylbenzhydrylamine (MBHA) resin. Preparation of the hydroxymethyl resin is described by Bodansky et al. (1966). Chloromethylated resins are commercially available from Bio Rad Laboratories (Richmond, Calif.) and from Lab. Systems, Inc. The preparation of such a resin is described by Stewart et al. (1969). BHA and MBHA resin supports are commercially available, and are generally used when the desired polypeptide being synthesized has an unsubstituted amide at the C-terminus. Thus, solid resin supports may be any of those known in the art, such as one having the formulae —O—$CH_2$-resin support, -NH BHA resin support, or -NH-MBHA resin support. When the unsubstituted amide is desired, use of a BHA or MBHA resin is preferred, because cleavage directly gives the amide. In case the N-methyl amide is desired, it can be generated from an N-methyl BHA resin. Should other substituted amides be desired, the teaching of U.S. Pat. No. 4,569,967 (Kornreich et al., 1986) can be used, or should still other groups than the free acid be desired at the C-terminus, it may be preferable to synthesize the peptide using classical methods as set forth in the Houben-Weyl text (1974).

The C-terminal amino acid, protected by Boc or Fmoc and by a side-chain protecting group, if appropriate, can be first coupled to a chloromethylated resin according to the procedure set forth in K. Horiki et al. (1978), using KF in DMF at about 60° C. for 24 hours with stirring, when a peptide having free acid at the C-terminus is to be synthesized. Following the coupling of the BOC-protected amino acid to the resin support, the α-amino protecting group is removed, as by using trifluoroacetic acid (TFA) in methylene chloride or TFA alone. The deprotection is carried out at a temperature between about 0° C. and room temperature. Other standard cleaving reagents, such as HCl in dioxane, and conditions for removal of specific α-amino protecting groups may be used as described in Schroder & Lubke (1965).

After removal of the α-amino-protecting group, the remaining α-amino- and side chain-protected amino acids are coupled step-wise in the desired order to obtain the intermediate compound defined hereinbefore, or as an alternative to adding each amino acid separately in the synthesis, some of them may be coupled to one another prior to addition to the solid phase reactor. Selection of an appropriate coupling reagent is within the skill of the art. Particularly suitable as a coupling reagent is N,N'-dicyclohexylcarbodiimide (DCC, DIC, HBTU, HATU, TBTU in the presence of HoBt or HoAt).

The activating reagents used in the solid phase synthesis of the peptides are well known in the peptide art. Examples of suitable activating reagents are carbodiimides, such as N,N'-diisopropylcarbodiimide and N-ethyl-N'-(3-dimethylaminopropyl)carbodiimide. Other activating reagents and their use in peptide coupling are described by Schroder & Lubke (1965) and aKapoor (1970).

Each protected amino acid or amino acid sequence is introduced into the solid-phase reactor in about a twofold or more excess, and the coupling may be carried out in a medium of dimethylformamide (DMF):$CH_2Cl_2$ (1:1) or in DMF or $CH_2Cl_2$ alone. In cases where intermediate coupling occurs, the coupling procedure is repeated before removal of the α-amino protecting group prior to the coupling of the next amino acid. The success of the coupling reaction at each stage of the synthesis, if performed manually, is preferably monitored by the ninhydrin reaction, as described by Kaiser et al. (1970). Coupling reactions can be performed automatically, as on a Beckman 990 automatic synthesizer, using a program such as that reported in Rivier et al. (1978).

After the desired amino acid sequence has been completed, the intermediate peptide can be removed from the resin support by treatment with a reagent, such as liquid hydrogen fluoride or TFA (if using Fmoc chemistry), which not only cleaves the peptide from the resin but also cleaves all remaining side chain protecting groups and also the α-amino protecting group at the N-terminus if it was not previously removed to obtain the peptide in the form of the free acid. If Met is present in the sequence, the Boc protecting group is preferably first removed using trifluoroacetic acid (TFA)/ethanedithiol prior to cleaving the peptide from the resin with HF to eliminate potential S-alkylation. When using hydrogen fluoride or TFA for cleaving, one or more scavengers such as anisole, cresol, dimethyl sulfide and methylethyl sulfide are included in the reaction vessel.

Cyclization of the linear peptide is preferably affected, as opposed to cyclizing the peptide while a part of the peptidoresin, to create bonds between Cys residues. To effect such a disulfide cyclizing linkage, fully protected peptide can be cleaved from a hydroxymethylated resin or a chloromethylated resin support by ammonolysis, as is well known in the art, to yield the fully protected amide intermediate, which is thereafter suitably cyclized and deprotected. Alternatively, deprotection, as well as cleavage of the peptide from the above resins or a benzhydrylamine (BHA) resin or a methylbenzhydrylamine (MBHA), can take place at 0° C. with hydrofluoric acid (HF) or TFA, followed by oxidation as described above.

The peptides are also synthesized using an automatic synthesizer. Amino acids are sequentially coupled to an MBHA Rink resin (typically 100 mg of resin) beginning at the C-terminus using an Advanced Chemtech 357 Automatic Peptide Synthesizer. Couplings are carried out using 1,3-diisopropylcarbodimide in N-methylpyrrolidinone (NMP) or by 2-(1H-benzotriazole-1-yl)-1,1,3,3-tetramethyluronium hexafluorophosphate (HBTU) and diethylisopropylethylamine (DIEA). The FMOC protecting group is removed by treatment with a 20% solution of piperidine in dimethylformamide(DMF). Resins are subsequently washed with DMF (twice), followed by methanol and NMP.

The conantokins are antagonists of the NMDA receptor subunits and are useful as anticonvulsant agents, as neuroprotective agents, as analgesic agents, for managing pain and for treating neurodegenerative disorders. The conantokins of the present inventions are particularly useful as such agents for treating neurologic disorders and psychiatric disorders that result from an overstimulation of excitatory amino acid receptors. That is, the invention pertains particularly to disorders in which the pathophysiology involves excessive excitation of nerve cells by excitatory amino acids or agonists of the NMDA receptor(s). Thus, the conantokins of the present invention are useful for the treatment and alleviation of epilepsy and as a general anticonvulsant agent. The use of conantokins in these conditions includes the administration of a conantokin in a therapeutically effective amount to patients in need of treatment. The conantokins can be used to treat the seizures, to reduce their effects and to prevent seizures.

The conantokins are also useful to reduce neurotoxic injury associated with conditions of hypoxia, anoxia or ischemia which typically follows stroke, cerebrovascular accident, brain or spinal chord trauma, myocardial infarct, physical trauma, drownings, suffocation,, perinatal asphyxia, or hypoglycemic events. To reduce neurotoxic injury, the conantokins should be administered in a therapeutically effective amount to the patient within 24 hours of the onset of the hypoxic, anoxic or ischemic condition in order for the conantokins to effectively minimize the CNS damage which the patient will experience.

The conantokins are further useful for the treatment of Alzheimer's disease, senile dementia, Amyotrophic Lateral Sclerosis, Multiple Sclerosis, Parkinson's disease, Huntington's disease, Down's Syndrome, Korsakoff's disease, schizophrenia, AIDS dementia, multi-infarct dementia, Binswanger dementia and neuronal damage associated with uncontrolled seizures. The administration of the conantokins in a therapeutically effective amount to a patient experiencing such conditions will serve to either prevent the patient from experiencing further neurodegeneration or it will decrease the rate at which neurodegeneration occurs. In addition, the conantokins can be administered in adjunct with conventional treatment agents to reduce the amount of such agents which need to be used.

The conantokins are also useful for treating chemical toxicity (such as addiction, morphine tolerance, opiate tolerance, opioid tolerance and barbiturate tolerance), anxiety, major depression, manic-depressive illness, obsessive-compulsive disorder, schizophrenia, mood disorders (such as bipolar disorder, unipolar depression, dysthymia and seasonal effective disorder), dystonia (movement disorder), sleep disorder, muscle relaxation, urinary incontinence, HIV infection and ophthalmic indications. In treating these conditions, a therapeutically effective amount of one or more conantokins is administered to a patient to completely treat the condition or to ease the effects of the condition. In addition, the conantokins are useful for memory/cognition enhancement (treating memory, learning or cognitive deficits), in which case a therapeutically effective amount of the conantokins is administered to enhance memory or cognition.

The conantokins are further useful in controlling pain, e.g., as analgesic agents, and the treatment of migraine, acute pain or persistent pain. They can be used prophylactically or to relieve the symptoms associated with a migraine episode, or to treat acute or persistent pain. For these uses, the conantokins are administered in a therapeutically effective amount to overcome or to ease the pain.

The anticonvulsant effects of conantokins have been demonstrated in animal models. In rodents, conantokins are effective against supramaximal tonic extension seizures produced by maximal electroshock and threshold seizures induced by subcutaneous (s.c.) pentylenetetrazole or picrotoxin. As described in further detail below, Conantokin R was found to have an antiseizure activity greater than 400,000-fold higher than the standard commercial antiepileptic drug, valproic acid. In addition, Conantokin R was found to have a protective index at least eight times better than that of valproic acid. Conantokins are also effective against focal seizures induced by aluminum hydroxide injection into the pre- and post-central gyri of rhesus monkeys. Conantokins, when administered to patients with refractory complex partial seizures, may markedly reduce seizure frequency and severity. Thus, conantokins are useful as anticonvulsant agents. Moreover, the clinical utility of conantokins as a therapeutic agent for epilepsy may include generalized tonic-clonic and complex partial seizures.

The neuroprotective effects of conantokins have been demonstrated in laboratory animal models. Conantokins protected against hypoxic damage to the hippocampal slice in vitro. In neonate rats, conantokins reduced the size of cortical infarcts and amount of hippocampal necrosis following bilateral carotid ligation and hypoxia. Thus, conantokins are useful as neuroprotective agents. Whereas other anticonvulsants may exhibit neuroprotectant properties (Aldrete et al., 1979; Abiko et al., 1986; Nehlig et al., 1990), these effects often occurred only at high, clinically achievable doses associated with considerable toxicity (Troupin et al., 1986; Wong et al., 1986). In contrast, conantokins exhibit both anticonvulsant and neuroprotectant effects at doses well tolerated by animals and humans.

The analgesic or anti-pain activity of conantokins is demonstrated in animal models of pain and in animal models of persistent pain. In these models, conantokins are (a) effective in nerve injury model studies; (b) effective in reducing the tolerance to opiate analgesics after chronic administration and (c) effective in inhibiting activation of NMDA receptors and thereby inhibiting the release of Substance P by small-diameter, primary, sensory pain fibers. Thus, conantokins are useful as analgesic agents and anti-pain agents for the treatment of acute and persistent pain. The conantokins are also useful for treating addiction, morphine/opiate/opioid tolerance or barbiturate tolerance.

The anti-neurodegenerative disease or neuroprotective activity of conantokins is demonstrated in animal models of Parkinson's disease. The conantokins are effective in reversing the behavioral deficits induce by dopamine depletion. The conantokins show behavioral potentiation, especially locomotor activity. The conantokins enhance the effect of L-DOPA in reversing the behavioral deficits induce by dopamine depletion. Thus, conantokins are effective neuroprotective agents and anti-neurodegenerative disease agents.

The effect of conantokins on muscle control is demonstrated in animals. At low doses, the conantokins are effective in hampering voiding at the level of the urethra. At higher doses, the conantokins are effective in eliminating all lower urinary tract activity. In the animal studies, it appears that the conantokins are more discriminatory in their inhibitory effects on striated sphincter than on bladder when compared with other NMDA antagonists. Thus, the conantokins can be dosed in such a way so as to selectively decrease bladder/sphincter dyssynergia, especially in spinal cord injured patients, and are therefore useful for treating urinary incontinence and muscle relaxation.

Pharmaceutical compositions containing a compound of the present invention as the active ingredient can be prepared according to conventional pharmaceutical compounding techniques. See, for example, *Remington's Pharmaceutical Sciences,* 17th Ed. (1985, Mack Publishing Co., Easton, Pa.). Typically, an antagonistic amount of active ingredient will be admixed with a pharmaceutically acceptable carrier.

The carrier may take a wide variety of forms depending on the form of preparation desired for administration, e.g., intravenous, oral, parenteral or intrathecally.

For oral administration, the compounds can be formulated into solid or liquid preparations such as capsules, pills, tablets, lozenges, melts, powders, suspensions or emulsions. In preparing the compositions in oral dosage form, any of the usual pharmaceutical media may be employed, such as, for example, water, glycols, oils, alcohols, flavoring agents, preservatives, coloring agents, suspending agents, and the like in the case of oral liquid preparations (such as, for example, suspensions, elixirs and solutions), or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form, in which case solid pharmaceutical carriers are obviously employed. If desired, tablets may be sugar-coated or enteric-coated by standard techniques. The active agent must be stable to passage through the gastrointestinal tract. If necessary, suitable agents for stable passage can be use and may include phospholipids or lecithin derivatives described in the literature, as well as liposomes, microparticles (including microspheres and macrospheres).

For parenteral administration, the compound may dissolved in a pharmaceutical carrier and administered as either a solution of a suspension. Illustrative of suitable carriers are water, saline, dextrose solutions, fructose solutions, ethanol, or oils of animal, vegetative or synthetic origin. The carrier may also contain other ingredients, for example, preservatives, suspending agents, solubilizing agents, buffers and the like. When the compounds are being administered intracerebroventricularly or intrathecally, they may also be dissolved in cerebrospinal fluid.

The conantokins can also be administered in a cell based delivery system in which a DNA sequence encoding a conantokin is introduced into cells designed for implantation in the body of the patient, especially in the spinal cord region. Suitable delivery systems are described in U.S. Pat. No. 5,550,050 and published PCT Application Nos. WO 92/19195, WO 94/25503, WO 95/01203, WO 95/05452, WO 96/02286, WO 96/02646, WO 96/40871, WO 96/40959 and WO 97/12635.

The conantokins are administered in an amount sufficient to antagonize the effects of excitatory amino acids or other agonists upon the NMDA receptor complex. The dosage range at which these conantokins exhibit this antagonistic effect can vary widely depending upon the particular disease or condition being treated, the severity of the patient's disease or condition, the patient, the specific conantokin being administered, the route of administration and the presence of other underlying disease states within the patient. Typically the conantokins exhibit their therapeutic effect at a dosage range from about 0.015 mg/kg to about 200 mg/kg, preferably from about 0.02 mg/kg to about 100 mg/kg of the active ingredient, more preferably from about 0.03 mg/kg to about 75 mg/kg of the active ingredient, and most preferably from about 0.03 mg/kg to about 50 mg/kg of the active ingredient. A suitable dose can be administered in multiple subdoses per day. Typically, a dose or sub-dose may contain from about 0.1 mg to about 500 mg of the active ingredient per unit dosage form. A more preferred dosage will contain from about 0.5 mg to about 100 mg of active ingredient per unit dosage form.

For newly diagnosed patients with a seizure disorder and patients with seizure disorders for whom changes in drugs are being made, a relatively low dosage of drug is started and increased over a week or so to a standard therapeutic dosage. After about a week at such dosage, blood levels are obtained to determine the patient's pharmacokinetic response and, if appropriate, whether the effective therapeutic level has been reached. If seizures continue, the daily dosage is increased by small increments as dosage rises above the usual. Once seizures are brought under control, the drug should be continued without interruption at least one seizure-free year. At that time, discontinuation of the drug should be considered, since about 50% of such patients will remain seizure free without drugs. Patients whose attacks initially were difficult to control, those who failed a therapy-free trial and those with important social reasons for avoiding seizures should be treated indefinitely.

EXAMPLES

The present invention is described by reference to the following Examples, which are offered by way of illustration and are not intended to limit the invention in any manner. Standard techniques well known in the art or the techniques specifically described below were utilized. The examples demonstrate the purification and chemical synthesis of conantokin R. Conantokin Oc, conantokin S1, conantokin L, conantokin Gm, conantokin Ca1, conantokin Ca2 and conantokin Qu are purified and synthesized in a similar manner. Conantokin derivatives and conantokin chimeras are made in conventional manner, such as chemically synthesizing the desired derivative or chimera.

Example 1

Methods

Sequence analysis. All sequence analyses were performed on the Applied Biosystems Model 477A pulsed liquid phase automated protein sequencer using the Nonnal-1 cycles. Peptides were immobilized on a glass fiber filter treated with TFA, in the presence of 3 mg Polybrene and 0.2 mg NaCl. PTH-amino acid derivatives were analyzed by RP-HPLC with an on-line Applied Biosystems Model 120A analyzer, and identified by retention time.

Pyridylethylation. The peptide (20 to 300 pmoles) was dissolved in 50 $\mu$l 0.25 M TRIS-HCl, 6 M in guanidine hydrochloride, and 2 mM in EDTA, pH 7.5. Reduction was then carried out by adding 2 $\mu$l 10% mercaptoethanol, aq., and incubating at room temperature for 30 min. The peptide was then alkylated by adding 2 $\mu$l of a 20% solution of 4-vinyl pyridine in ethanol and incubating the mixture at room temperature, in the dark, for 15 min. The solution was acidified prior to de-salting by RP-HPLC with 5 $\mu$l of 10% TFA.

HPLC. Analytical and micro-preparative HPLC were performed on the Hewlett-Packard Model 1090M system equipped with a diode array detector, using a Brownlee Aquapore RP-300 C-8 column, 2.1×100 mm and a TFA/acetonitrile system.

Amino acid analysis. Hydrolysis was performed in 4 N methanesulfonic acid at 110° C. for 24 hrs. The hydrolysates were then analyzed on a Perkin-Elmer HPLC-based amino acid analyzer utilizing automated post-column OPA derivatization and fluorescence detection. Separation of the amino acids was done on an Interaction A-111 column at 55° C.

Total synthesis. Chemical synthesis of conantokin R and its C-terminal amidated analog was carried out essentially as described for conantokin G by Rivier et al. (1987), and as described further below. Most fluorenylmethoxycarbonyl (Fmoc) amino acids were purchased from Bachem, Torrance, Calif. Fmoc-γ-γ-di-t-bu-γ-carboxyglutamic acid (Gla) was synthesized as described by Rivier et al. (1987) Side chain protection of Fmoc amino acids included Glu(γ-tbu), Lys(ε-Boc), Arg(MTR), Cys(S-trityl) and Tyr(O-but).

Example 2

Purification of Conantokin R

Specimens of *Conus radiatus* were collected by trawlers in Manila Bav. Venom ducts were dissected, and crude venom was harvested and fractionated using reverse phase HPLC chromatography as described under Methods. The various fractions were examined for sleep-inducing activity. Several such fractions were identified, including a major fraction referred to as the "sleeper-I peptide." The sleeper-I peptide was purified to homogeneity.

The amino acid sequence of the sleeper-I peptide was determined by standard Edman methods. Two sequencing runs were carried out on the native material. A number of blank positions were detected on the first run, because of the homology of the sequence obtained with previously characterized conantokins T and G, we hypothesized that some of the blank positions might be γ-carboxyglutamate (Gla) residues which would be consistent with a small of amount of Glu detected. In the second sequencing run, the peptide was first reduced and alkylated in order to convert cvsteines to the pyridylethylated derivative using 4-vinylpyridine. Two of the blank positions (21 and 25) from the first sequencing run yielded pyridylethylated Cys. This suggested that the remaining blank positions (3, 4, 11, 15) might be Gla residues.

Mass spectrometry was also used to assess the status of the missing residues; electrospray mass spectrometry was used, yielding a monoisotopic mass (MH$^+$) at mlz=3097.6. This value is consistent with the amino acid sequence if all remaining positions were indeed γ-carboxyglutamate residues, with the two cysteine residues in disulfide linkage and a free carboxyl C-terminus (predicted monoisotopic mass is 3097.4).

Together, the data are consistent with the structure of the sleeper-I peptide shown in SEQ ID NO:4, wherein the Cys residues are in disulfide linkage. Because of the clear homology of the peptide to conantokins G and T, this peptide was designated as conantokin R (for radiatus).

Example 3

Synthesis of Conantokin R and Conantokin R Amide

The proposed sequence assignment above was directly confirmed by chemical synthesis. Solid phase synthesis of both peptides on 3 g of the Fmoc-Pro-palkoxybenzylalcohol resin and 1 g of the 2,4-dimethoxybenzhydryl-amine resin (Rivier et al., 1987) was done manually (0.5–3.0 mmol of amino acid/g of resin). Monitoring of coupling/deblocking for each cycle was done using the Kaiser test. (Kaiser, 1970) Removal of the Fmoc group was effected by treatment with 0.1 M TBAF (tetrabutylammonium fluoride) in dimethylformamide (DMF) in the case of the peptide acid and with two treatments (3+7) min of a 20% solution (v/v) of piperidine in DMF for the peptide amide. Resin washing was accomplished by repeated application of DMF and/or dichloromethane (DCM) and methanol (MeOH). Couplings were mediated by 1,3-diisopropylcarbodiimide (DIC) in DCM/DMF in the presence of 0.60.7 eq of 1-hydroxybenzotiriazole (HOBt). Fmoc-Asn was incorporated into the peptide with the side chain unprotected, in the presence of 0.6 to 2 equivalent of HOBT in dimethylsulfoxide (DMSO)-DCM/DMF. The crude peptides were purified using preparative HPLC techniques as previously described (Rivier et al., 1984). Peptides were dissolved in 0.1 M sodium borate buffer in the presence of 10 mM CaCl$_2$ in order to obtain sharp absorbances for CZE at pH 8.5 and HPLC at pH 7.4.

Conantokin R. Cleavage and deprotection of the peptide (2×2.0 g peptido-resin) was achieved by treatment with a freshly prepared mixture of trifluoroacetic acid, thioanisole, H$_2$O, ethanedithiol and DCM (40:8:1:2:49) (20 ml/g) at 37° C. for 7.25 hr. Trial cleavages of small amounts (10 mg of peptide resin had demonstrated that the peptide would be freed from the resin and all side chains deprotected, while the Gla would remain intact under these conditions. The peptide was precipitated from the cleavage solution and washed by the addition of tert-butyl methyl ether (5×100 ml) in centrifuge tubes. The solid was suspended in water (60 ml) and the suspension filtered. The tubes and resin were washed with 40% acetic acid. The extracts were immediately cooled, and then dissolved and diluted to 4 l (in the presence of 10 g ammonium acetate pH 4.3). The pH was adjusted to 7.8 with NH$_4$OH and the solution was allowed to slowly stir and air oxidize at 4° C. for 3 d. The progress of oxidation was followed by the Ellman test and HPLC analysis as the oxidized product formed. After acidification of the solution to pH 5 with acetic acid, the solution (2×≈1.5 l) was applied directly to a preparative HPLC cartridge. The gradient of acetonitrile applied to the preparative cartridge in 0.1% TFA was 23–35% in 1 hr, with a flow rate of 100 ml/min. Analysis of the generated fractions was achieved using isocratic conditions (24% acetonitrile, in 0.1% TFA) on a 5 μm Vydac column. Peptide-containing fractions were then lyophilized to yield 120 mg. The powder was re-applied to the preparative cartridge in TEAP pH 2.3 and a gradient of acetonitrile 12–24% eluted the peptide. Desalting was carried out using an acetonitrile gradient from 23–35% in 0.1% TFA in 30 min, then re-application and elution using acetonitrile from 12–57% in 10 min. Purified fractions were pooled and lyophilized yielding conantokin R as the trifluoroacetate (36 mg). Results of the HPLC and capillary zone electrophoresis (CZE) analyses of this material are given in Tables 1 and 2, respectively. Amino acid analysis after acid hydrolysis gave the following ratios with expected values in parentheses: Asp (2), 1.96; Glu (5) including presence of four Gla residues, 4.91; Pro (1) 1.26; Gly (2), 1.95; Ala (5) 5.00, Cys (2), 1.65; Val (2) 1.97; Met (1), 0.88; Ile (1), 0.097; Leu (1), 1.01; Tyr (1), 0.98; Lys (3), 3.03; Arg (1), 0.98.

Conantokin R amide: Cleavage, deprotection and cyclization of the peptide (1.6 g peptido-resin) was achieved as described above. However, after acidification of the oxidized solution to pH 5 with acetic acid, the solution was passed through two columns packed with cation-exchange resin (2.5×7 cm) Bio-Rex 70 (H$^+$ form). Eluent was checked by HPLC to verify absence of the peptide. The column was then washed with 1% aqueous acetic acid (250 ml) and the desired oxidized peptide was eluted with 50% aqueous acetic acid. Fractions were collected (5 ml) and tested with ninhydrin. Peptide-containing fractions were combined and diluted 5× with H$_2$O, shell frozen and lyophilized (yield 300 mg). The gradient of acetonitrile applied to the preparative cartridge in TEAP pH 2.25 was 15–30% in 1 hr, with a flow rate of 100 ml/min. Analysis of the generated fractions was achieved using isocratic conditions (21% acetonitrile in TEAP pH 2.25) on a 5 μm Vydac column. Peptide-containing fractions were then re-applied to the preparative cartridge in TEAP pH 5.2 and the same gradient of acetonitrile applied. Desalting was carried out using an acetonitrile gradient from 9–36% in 0.1% TFA in 45 min. Purified fractions were pooled and lyophilized yielding conantokin R amide as the trifluoroacetate (12.5 mg). The purified material was analyzed by HPLC and capillary zone electrophoresis (see Tables 2 and 3). Amino acid analysis of the synthetic material was consistent with the conantokin R sequence. The synthetic material exhibited the same biological activity as the native material, and a mixture of synthetic and native material gave a single homogeneous peak on HPLC.

A conantokin R analog with an amidated C-terminus was also synthesized. This material did not co-elute with the native conantokin R, verifying that in the natural peptide, the C-terminal Pro residue had a free carboxyl group. Nevertheless, this material was also biologically active with similar activity shown by conantokin R. Electrospray mass spectrometry (MS) for conantokin R and conantokin R-amide, showed protonated molecular ion $[MH]^+$ at m/z= 3097.6 and m/z=3096.7, corresponding to the calculated monoisotopic peptide acid of 3097.4 and 3096.4, respectively. FAB MS was also performed for conantokin R and the spectrum showed an intact ion at m/z=3098.4.

TABLE 2

HPLC Analysis of Conantokin R (A) and Conantokin R-Amide (B)

| Solvent System | Flow Rate | Gradient | Retention Vol (ml) | % Purity |
|---|---|---|---|---|
| A. TEAP pH 7.4/$CH_3CN^a$ | 0.2 | 18–36% $CH_3CN$ in 30' | 2.0 | 85 |
| A. 0.1% TFA/$CH_3CN^b$ | 2.0 | 6–42% $CH_3CN$ in 45' | 54.0 | ≈90 |
| B. TEAP pH 7.4/$CH_3CN^a$ | 0.2 | 18–36% $CH_3CN$ in 30' | 2.3 | 90 |
| B. TEAP pH 2.3/$CH_3CN^b$ | 2.0 | 15–30% $CH_3CN$ in 20' | 31.0 | 90 |

[a]UV monitoring at 214 nm, 0.12 absorbance unit at full scale. Column was Vydac (0.21 × 15 cm) packed with $C_{18}$ 5 μm particles, 300 Å pore size.
[b]UV monitoring at 210 nm, 0.10 absorbance unit at full scale. Column was Vydac (0.46 × 25 cm) packed with $C_{18}$ 5 μm particles, 300 Å pore size.

TABLE 3

CZE Analysis of Conantokin R (A) and Conantokin R-Amide (B)

| Buffer System | Voltage (kV) | Migration time (min) | % Purity |
|---|---|---|---|
| A. 0.1 M sodium borate in (85 $H_2O$:15 $CH_3CN$) pH 8.5[a] | 15 | 9.0 | ≈95 |
| A. 0.1 M phosphate pH 1.5[b] | 12 | 15.5 | 95 |
| B. 0.1 M sodium borate in (85 $H_2O$:15 $CH_3CN$) pH 8.5[a] | 15 | 8.4 | ≈90 |
| B. 0.1 M phosphate pH 1.5[b] | 12 | 15.7 | 96 |

[a]UV monitoring at 214 nm, 0.01 absorbance unit at full scale. Capillary was Beckman eCAP fused silica (75 μm × 60 cm). Temperature was maintained at 30° C.
[b]UV monitoring at 214 nm, 0.01 absorbance unit at full scale. Capillary was Beckman eCAP fused silica (75 μm × 50 cm). Temperature was maintained at 30° C.

Example 4
Isolation of DNA Encoding Conantokins

DNA coding for the conantokins was isolated and cloned in accordance with conventional techniques using the general procedures and probes or primers set forth below.

Con G: The DNA was isolated using the toxin sequence degenerate probe DHOG108: CARGARAAYCARGARYT (SEQ ID NO:44) by Southern hybridization from a library of *C. geographus* DNA. The sequence of the DNA and its corresponding amino acid sequence are set forth in SEQ ID NO:45 and SEQ ID NO:46, respectively. The mature peptide sequence prior to Gla modification (residues 81 to 97 of SEQ ID NO:46) contains a Val at position 5 instead of Leu identified in the isolated peptide. The C-terminal GKR are processed to a C-terminal amide in the mature peptide.

Con R: The DNA was initially isolated using the probe DHOG424: CCYTTNGCDATRTTYTC (SEQ ID NO:47) by Southern hybridization from a library of *C. radiatus* DNA. The full length clone was obtained by Southern Hybridization using the signal sequence probe DHOG450: GCCGTGCCTAGGATTA (SEQ ID NO:48). The sequence of the DNA and its corresponding amino acid sequence are set forth in SEQ ID NO:49 and SEQ ID NO:50, respectively. The mature peptide sequence prior to Gla modification corresponds to residues 81 to 107 of SEQ ID NO:50.

Con Oc: The DNA was isolated using PCR with the signal sequence and 3' untranslated primers DHOG474: TGCTCGAATAAACATGAAAGATTTGGGGAA (SEQ ID NO:51) and DHOG475: TCTGCGATGCAACTGTACACGTATCTG (SEQ ID NO:52). The sequence of the DNA and its corresponding amino acid sequence are set forth in SEQ ID NO:53 and SEQ ID NO:54, respectively. The mature peptide sequence prior to Gla modification corresponds to residues 74 to 96 of SEQ ID NO:54. The C-terminal GR are processed to a C-terminal amide in the mature peptide.

Con S1: The DNA was isolated using PCR with the signal sequence and 3' untranslated primers DHOG474 and DHOG475. The sequence of the DNA and its corresponding amino acid sequence are set forth in SEQ ID NO:55 and SEQ ID NO:56, respectively. The mature peptide sequence prior to Gla modification corresponds to residues 80 to 103 of SEQ ID NO:56.

Con L: The DNA was isolated using PCR with the signal sequence and 3' untranslated primers DHOG474 and DHOG475. The sequence of the DNA and its corresponding amino acid sequence are set forth in SEQ ID NO:57 and SEQ ID NO:58, respectively. The mature peptide sequence prior to Gla modification corresponds to residues 74 to 92 of SEQ ID NO:58. The C-terminal GK are processed to a C-terminal amide in the mature peptide.

Con Gm: The DNA was isolated using PCR with the signal sequence and 3' untranslated primers DHOG474e: GGAATTCAATAAACATGAAAGATTTGGGGAA (SEQ ID NO:59) and DHOG475E: GGAATTCGCGATGCAACTGTACACGTATCTG (SEQ ID NO:60). The sequence of the DNA and its corresponding amino acid sequence are set forth in SEQ ID NO:61 and SEQ ID NO:62, respectively. The mature peptide sequence prior to Gla modification corresponds to residues 74 to 92 of SEQ ID NO:62. The C-terminal GKR are processed to a C-terminal amide in the mature peptide.

Con Ca2: The DNA was isolated using PCR with the signal sequence and 3' untranslated primers DHOG474e and DHOG475e. The sequence of the DNA and its corresponding amino acid sequence are set forth in SEQ ID NO:63 and SEQ ID NO:64, respectively. The mature peptide sequence prior to Gla modification corresponds to residues 74 to 91 of SEQ ID NO:64. The C-terminal GK are processed to a C-terminal amide in the mature peptide.

Con Qu: The DNA was isolated using PCR with the signal sequence and 3' untranslated primers DHOG474e and DHOG475e. The sequence of the DNA and its corresponding amino acid sequence are set forth in SEQ ID NO:65 and SEQ ID NO:66, respectively. The mature peptide sequence prior to Gla modification corresponds to residues 74 to 91 of SEQ ID NO:66. The C-terminal GKRK are processed to a C-terminal amide in the mature peptide.

On the basis of the peptide sequences for these conantokins, the consensus N-terminal peptide Met-Xaa$_1$-Leu-Tyr-Thr-Tyr-Leu-Tyr-Leu-Leu-Val-Xaa$_2$-Leu-Val-Xaa$_3$-Xaa$_4$(SEQ ID NO:67), where Xaa$_1$ is His or Gln, Xaa$_2$ is Pro or Ser. Xaa$_3$ is Thr or Ala and Xaa$_4$ is Leu or Phe is derived. Primers and/or probes are made on the basis of this sequence and used alone or in combination with the primers and/or probes described above to isolate additional conantokin peptides from other species of Conus.

Example 5

Specificity of Conantokin R for NMDA Receptor Subtypes

Conantokins G and T were previously shown to inhibit NMDA receptors in a variety of systems. The efficacy of conantokin R was compared to conantokin G using cloned NMDA receptor subunit combinations expressed in oocytes.

The NR1 subunits can be functionally expressed as a homomeric NMDA receptor complex in oocytes. From a comparison of the effects of conantokin R and conantokin G on such homomeric NR1 subunit complex, it is clear that while conantokin G inhibits both of the major splice variants tested, conantokin R is selective. At the concentrations tested, the peptide only inhibited the NR1.1 B subtype, with no effect on the corresponding A subtype. Specifically, Conantokin R at a concentration of 3 $\mu$M inhibited approximately 95% of the current produced by the NR1-1b/NR2B NMDA subtype in response to glutamate and glycine. The use of lower concentrations of Conantokin R gave a K$_i$ of 0.14 $\mu$M for the NR1-1b/NR2B subtype. The affinity of Conantokin R appears to be greater than 50-fold higher for this subtype than for the NR1-1b/NR2D combination, which was not affected even at 10 $\mu$M peptide. Conantokin R was found not to inhibit the AMPA receptor GluR1 and kainate receptors (GluR6).

The effect of conantokins G and R on heteromeric complexes containing both NR1 and NR2 subunit combinations was also examined. In the combinations of NR1:NR2B examined, the currents being elicited by the presumptive heteromeric combination are much larger than when homomeric NR1 subunits are expressed. Conantokin R and conantokin G both inhibited such complexes if the B splice variant of the NR1 subunit was used. However, conantokin R proved to be selective for the B splice variant of the NR subunit, even in these heteromeric complexes, while conantokin G was not. The results indicate that conantokin R is a subtype-specific antagonist of the NMDA receptor, and has a preference for the B splice variant which contains an additional 21 amino acids.

Example 6

In vivo Activity of Conantokins in Frings Audiogenic Seizure Susceptible Mice In vivo anticonvulsant activity of conantokins was analyzed in Frings audiogenic seizure susceptible mice as described by White et al. (1992). The results for conantokin R are shown in Tables 4, 5 and 6.

TABLE 4

Effect of Conantokin R on the Audiodenic Seizure Susceptibility of Frings Mice Following i.c.v. Administration

| Dose | # Protected/# Tested | | # Protected/# Tested | |
|---|---|---|---|---|
| (pmol, i.c.v) | 15 min. | 60 min. | 15 min. | 60 min. |
| 90 | 4/4 | 4/4 | 1/4 | 4/4 |
| 360 | 4/4 | 4/4 | 4/4 | 3/4 |

Ref: SW1:154

TABLE 5

Time Effect of Conantokin R Against Augiogenic Seizure Susceptibility of Frings Mice Following i.c.v. Administration

| | | Time (hrs) | | | | | |
|---|---|---|---|---|---|---|---|
| | Dose | 1/4 | 1/2 | 1 | 2 | 4 | Reference |
| # Prot./# Tested | 9 pmol | 2/4 | 2/3 | 3/4 | 1/4 | 0/4 | SW1:155, 159 |
| # Toxic/# Tested | 9 pmol | 1/8 | 0/4 | 1/8 | 0/4 | 0/4 | SW1:154, 160 |

TABLE 6

Effect of Conantokin R on the Audiogenic Seizure Susceptibility of Frings Mice Following i.c.v. Administration

| Dose (pmol, i.c.v.) | Seizure Score ± S.E.M. | # Protected/ # Tested (at 1 hr) | ED$_{50}$ (pmol, i.c.v.) | # Toxic/ # Tested (at ¼ hr) | TD$_{50}$ (pmol) |
|---|---|---|---|---|---|
| 2.27 | 5 ± 0 | 0/4 | | | |
| 4.50 | 4.4 ± 0.62 | 1/8 | | | |
| 9 | 2.75 ± 0.86 | 4/8 | 9.00 | | |
| 1.8 | 1.125 ± 0.58 | 7/8 | (5.98–14.3)* | | |
| 9 | 0 ± 0 | 4/4 | | 1/8 | 164 |
| 18.0 | — | — | | 4/8 | (111–233)* |
| 36.0 | 0 ± 0 | 4/4 | | 8/8 | |

*95% confidence interval
Ref: SW1:153, 154, 159–161

Conantokin R yielded an effective dose (ED$_{50}$) of 9 pmol. The ED$_{50}$ for conantokin-T was 5.1 pmol (95% CI=3.3–9.5 pmol). The ED$_{50}$ for conantokin G was 1.0 pmol (95% CI=1.0–2.0 pmol). Furthermore, conantokin R yielded a toxic dose (TD$_{50}$) of 164 pmol. The dose required to elicit neurotoxicity was 18 times greater than the effective dose ($TD_{50}$/($ED_{50}$—164/9=18=Protective Index, PI). The $TD_{50}$ for conantokin G was 28 pmol (95% CI=22–35 pmol), yielding a protective index of 27. Moreover, the PI of 18 for conantokin R and 27 for conantokin G exceeds that of other anti-seizure medications tested in this model. The therapeutic dose of typical anti-seizure medications is close to the toxic dose (typical PI=2–3). Since the protective index is high for conantokin R and conantokin G, these peptides will be better tolerated than previous anti-convulsant agents.

Similar results are obtained for conantokin S1, G, T, L, Gm, Ca2 and Qu and analogs of these peptides in which the γ-carboxyglutamic acid residues other than at positions 3 and 4 are substituted by other amino acid residues, including Ser, Ala, Glu and Tyr. These results are consistent with the finding that several Con G synthetic analogs possess high affinities for non-competitive inhibition of polyamine enhanced [$^3$H]MK-801 binding (Zhou et al., 1996).

Example 7

Figure 2:
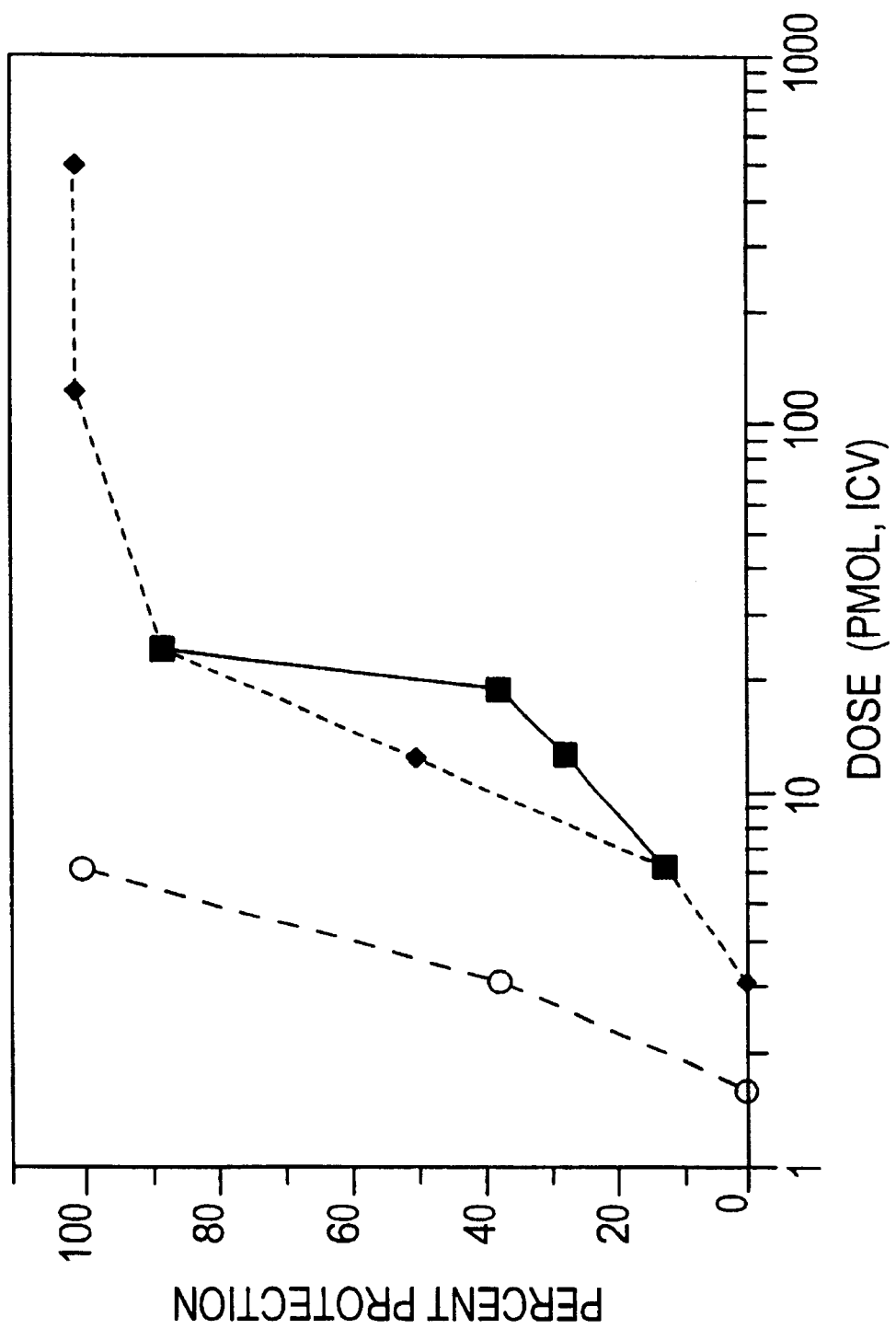
FIG. 2 shows the ability of conantokins (Con R (♦), Con T (■) Con G (○)) to block audiogenic seizures in a dose-dependent manner following i.c.v. administration to Frings audiogenic mice.
Figure 3:
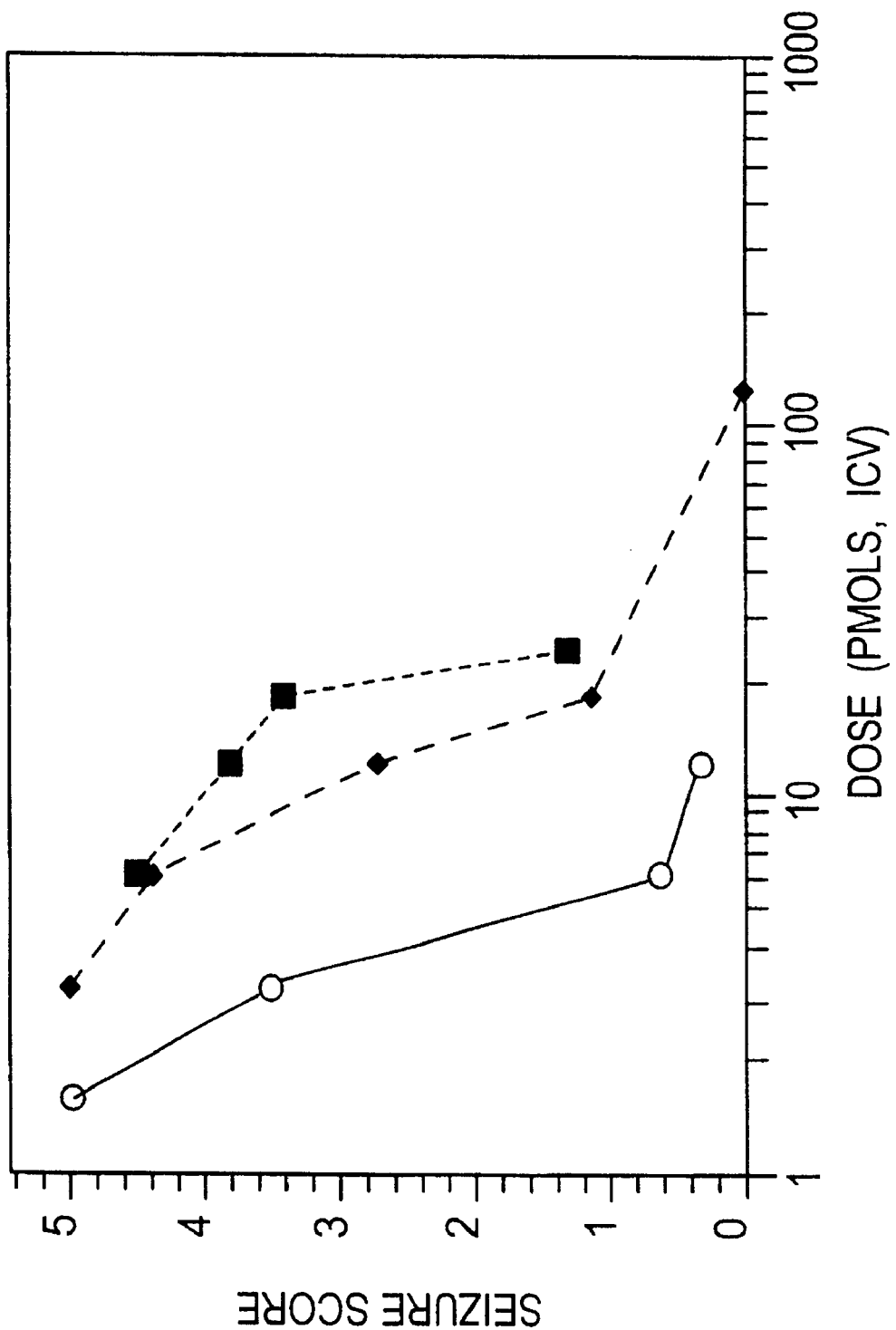
FIG. 3 shows the dose-dependent reduction in seizure severity following i.c.v. administration to Frings audiogenic mice for conantokins (Con R (♦), Con T (■) Con G (○)).
Figure 4:
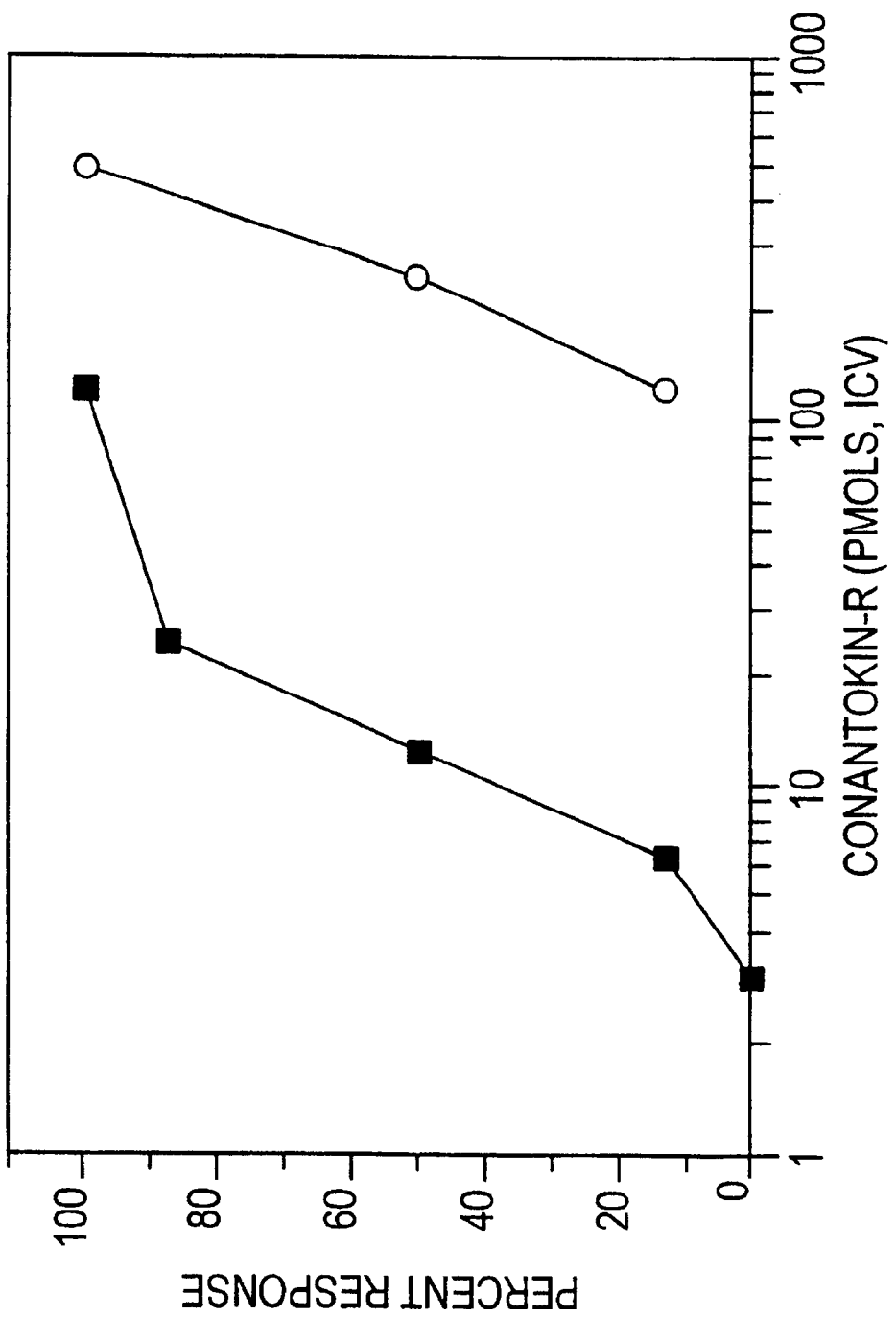
FIG. 4 shows the dose-dependent blockage of audiogenic sequences by Con R at non-toxic doses. Protection (■) and impairment (○) for Con R are shown.

Comparison of In vivo Activity of Conantokins and Standards in Frings Audiogenic Seizure Susceptible Mice The anticonvulsant profile of several conantokins and the standards dizocilpine (MK-801), ifendropil and valproic acid was determined using Frings audiogenic seizure-susceptible mice (25–30 g body weight) obtained from the house colony of the University of Utah. All intracerebroventricularly (i.c.v.) injections were made free-handed into the lateral ventricle (approximately 1 mm lateral, 1 mm anterior from bregma and to a depth of 3 mm from the surface of the skull) of awake mice with a 10 μl Hamilton syringe. Varying doses of the compounds were tested. At the predetermined time of peak anticonvulsant effect, individual mice were placed into a round Plexiglas chamber (diameter, 15 cm; height, 18 cm) pitted with an audio transducer (Model A5-ZC; FET Research & Development, Salt Lake City, Utah) and exposed to a high intensity sound stimulus (110 decibels, 11 KHz) for 25 seconds. Animals not displaying tonic forelimb or hindlimb extension were considered protected. The effect of the test compounds on motor performance was assessed by the rotorod test (Dunham and Miya, 1957). For this procedure, mice were tested for their ability to maintain balance on a rotating (6 rpm) knurled Plexiglas rod (1 inch diameter) for one minute. Mice unable to maintain balance in three successive trials during the test period were considered toxic. The median effective dose ($ED_{50}$) and the median toxic dose ($TD_{50}$) was calculated by probit analysis (Finney, 1971). For these studies, the dose of each test substance was varied between the limits of 0 and 100% protection and toxicity. The protective index (PI) is $TD_{50}/ED_{50}$. The results are shown in Tables 7 and 8. The time-dependent inhibition of audiogenic seizures by Con R following i.c.v. administration is shown in FIG. 1. The ability of conantokins (Con R (♦), Con T (■) Con G (○)) to block audiogenic seizures in a dose-dependent manner following i.c.v. administration is shown in FIG. 2. The dose-dependent reduction in seizure severity following i.c.v. administration for conantokins (Con R (♦), Con T (■) Con G (○)) is shown in FIG. 3. The dose-dependent blockage of audiogenic seizures by Con R at non-toxic doses is shown in FIG. 4. Protection (■) and impairment (○) are shown with an $ED_{50}$ of 9 pmol and a $TD_{50}$ of 164 pmol.

TABLE 7

Comparative Anticonvulsant Efficacy, Minimal Motor Impairment and Protective Index of Conantokins R, T, and G and Ifenprodil Following I.C.V. Administrations

| Test Substance | Time of Test[a] (min) | nmols, i.c.v. | | |
|---|---|---|---|---|
| | | $ED_{50}$[b] | $TD_{50}$[b] | P.I. |
| Con R | 60, 15 | 0.013[c] (0.0083–0.020) | 0.228[d] (0.154–0.323) | 17 |
| Con T | 30, 15 | 0.017 (0.011–0.032) | 0.228 (0.154–0.323) | 13 |
| Con G | 30, 15 | 0.0035 (0.002–0.005) | 0.094 (0.073–0.116) | 27 |
| Ifenprodil | 5, 5 | ~25 | <25 | <1 |

[a]First time, $ED_{50}$; Second time, $TD_{50}$
[b]95% confidence interval in parentheses
[c]The values for $ED_{50}$ and $TD_{50}$ for Con R, Con T, and Con G are the raw data. These numbers are multiplied by 0.72 for Con R and by 0.3 for Con G and Con T to obtain values corrected for peptide content. The PI numbers do not change.

TABLE 8

Comparative Anticonvulsant Efficacy, Minimal Motor Impairment and Protective Index of Conantokin R, MK801, Ifenprodil and Valproic Acid Following I.C.V. Administration

| Test Substance | Time of Test[a] (min) | nmols, i.c.v. | | |
|---|---|---|---|---|
| | | $ED_{50}$[b] | $TD_{50}$[b] | P.I. |
| Con R | 60, 15 | 0.013[c] (0.0083–0.020) | 0.228[d] (0.154–0.323) | 17 |
| MK801 | 5, 5 | 0.641 (0.415–0.933) | 1.227 (0.639–4.532) | 1.9 |
| Valproic Acid | 5, 5 | 5644 (3707–7759) | >6000 <12,000 | 1.1–2.2 |
| Ifenprodil | 5, 5 | ~25 | <25 | <1 |

[a]First time, $ED_{50}$; Second time, $TD_{50}$
[b]95% confidence interval in parentheses
[c]The values for $ED_{50}$ and $TD_{50}$ for Con R are the raw data. These numbers are multiplied by 0.72 for Con R to obtain values for peptide content. The PI number does not change.

Example 8

In vivo Activity of Conantokins in CF No. 1 Mice

In vivo anticonvulsant activity of conantokins R, S1, G, T, L, Gm, Ca and Qu are analyzed in CF No. 1 mice as described by White et al. (1995), using the maximal electroshock, subcutaneous pentylenetetrazole (Metrazol) seizure threshold and threshold tonic extension test. Each of the conantokins tested are found to have anticonvulsant activity. Specifically, the activity of Conantokins R and G in this model animal are shown in Table 9.

TABLE 9

Anticonvulsant Efficacy, Minimal Motor Impairment and
Protective Index of Conantokins G and R Following I.C.V. Administration

| Test Substance | Frings Audiogenic Mice | | | CF #1 Mice | | |
|---|---|---|---|---|---|---|
| | $ED_{50}{}^a$ | $TD_{50}{}^a$ | P.I.[b] | MES $ED_{50}{}^a$ | $TD_{50}{}^a$ | P.I.[b] |
| Con G | 0.0035[c] | 0.094[c] | 27 | 0.026 | 0.066 | 2.5 |
| | (0.002–0.005) | (0.073–0.116) | | (0.013–0.038) | (0.048–0.091) | |
| Con R | 0.013 | 0.228 | 17 | 0.083 | ~0.300 | 3.6 |
| | (0.0083–0.020) | (0.154–0.323) | | (0.029–0.117) | | |

[a] nmols; 95% confidence intervals in parentheses
[b] Protective Index ($TD_{50}/ED_{50}$)
[c] The values for $ED_{50}$ and $TD_{50}$ for Con R and Con G are the raw data. These numbers are multiplied by 0.72 for Con R and by 0.3 for Con G to obtain values corrected for peptide content. The PI numbers do not change.

Example 9

In vivo Activity of Conantokin T in Frings Audiogenic Audiogenic Seizure-Susceptible Mice Following I.V. Administration

In vivo anticonvulsant activity of Con T was analyzed in Frings audiogenic seizure-susceptible mice as described above except that the peptide was administered intravenously (IV) at 12 mg/kg. The peptide was administered to naive mice and pre-stimulated mice. The mice were dosed i.v. and stimulated at the indicated time intervals and the protection was measured. The pre-stimulated mice were stimulated at 1 minute as a pre-stimulation and then stimulated at the indicated time intervals. The results are shown in Tables 10 and 11. No animals exhibited behavioral toxicity at this dose, as determined by the rotorod test as described above.

TABLE 10

Anticonvulsant (Frings Audiogenic Seizure-Susceptibile Mouse Model) Activity of Conantokin T Following Intravenous (IV) Administration: Naive Animals

| Time of Test (min) | Con-T # Protected/ # Tested | % Protected | Saline Control # Protected/ # Tested | % Protected |
|---|---|---|---|---|
| 1 | | | | |
| 10 | 0/9 | 0% | 0/5 | 0% |
| 20 | 1/2 | 50% | 0/2 | 0% |
| 30 | 2/6 | 33% | 0/5 | 0% |
| 60 | 4/6 | 67% | | |
| 240 | 1/6 | 17% | | |

TABLE 11

Anticovulsant (Frings Audiogenic Seizure-Susceptible Mouse Model) Activity of Conantokin T Following Intravenous (IV) Administration: Pre-Stimulated Animals

| Time of Test (min) | Con-T # Protected/ # Tested | % Protected | Saline Control # Protected/ # Tested | % Protected |
|---|---|---|---|---|
| 1 | 1/2 | 50% | 0/2 | 0% |
| 10 | | | | |
| 20 | 1/2 | 50% | 0/2 | 0% |
| 30 | 3/5 | 60% | | |
| 60 | 6/7 | 86% | 6/12 | 50% |
| 240 | 6/11 | 55% | 0/4 | 0% |

Table 10 shows 67% protection for the naive animals at 60 minutes following the i.v. of Conantokin T. The pre-stimulation sometimes results in erratic protection which may be to compromising the blood-brain-barrier, thus, allowing CNS penetration by compounds otherwise would not penetrate. Alternatively, the result in the pre-stimulated animals could be due to making the animals refractory to subsequent seizures. Nevertheless, the present experiment demonstrates the bioavailability of Conantokin T, since it protected the naive animals following i.v. dose. Similar results were obtained with Conantokin G.

Example 10

In vivo Activity of Conantokin G in Frings Audiogenic Seizure-Susceptible Mice Following I.C.V. Administration

In vivo anticonvulsant activity of conantokin G was analyzed in Frings audiogenic seizure susceptible mice as described above, except that the peptide was administered i.c.v. at 0.0038 nmol or 0.0056 nmol. Table 12 shows the time to onset of the anticonvulsant activity of Con G following i.c.v. administration.

TABLE 12

Time to Onset of Anticonvulsant Activity of Conantokin G: Seizure Protection Following I.C.V. Administration to Frings Audiogenic Mice

| Test Substance | Dose nmol, i.c.v. | Percent Protection (at time of test, min) | | | | | |
|---|---|---|---|---|---|---|---|
| | | 1 | 2 | 3 | 4 | 5 | 60 |
| Con G[1] | 0.0038 | 0 | 0 | 0 | 100 | 100 | 87.5 |
| Con G[2] | 0.0056 | 25 | 50 | 100 | — | — | 100 |

[1] N = 16;
[2] N = 8

At a Con G dose of 0.038 nnol, seizure protection was observed in 100% of the animals tested at four minutes. As a control, at the same dose of Con G, 87.5% of the animals were protected at 60 minutes. Moreover, at a Con G dose of 0.0056 nmol, seizure protection was observed in 25% of the animals tested at one minute, 50% at two minutes and 100% at three minutes. As a control, at the same dose of Con G, 100% of the animals were protected at 60 minutes. No animals exhibited behavioral toxicity (rotorod minimal motor impairment) at the doses of Con G and the times tested. Thus, Con G elicits a very rapid time to onset (within one to three minutes) of anticonvulsant activity, with high-potency and low behavioral toxicity, following i.c.v. administration to Frings audiogenic mice.

Figure 5:
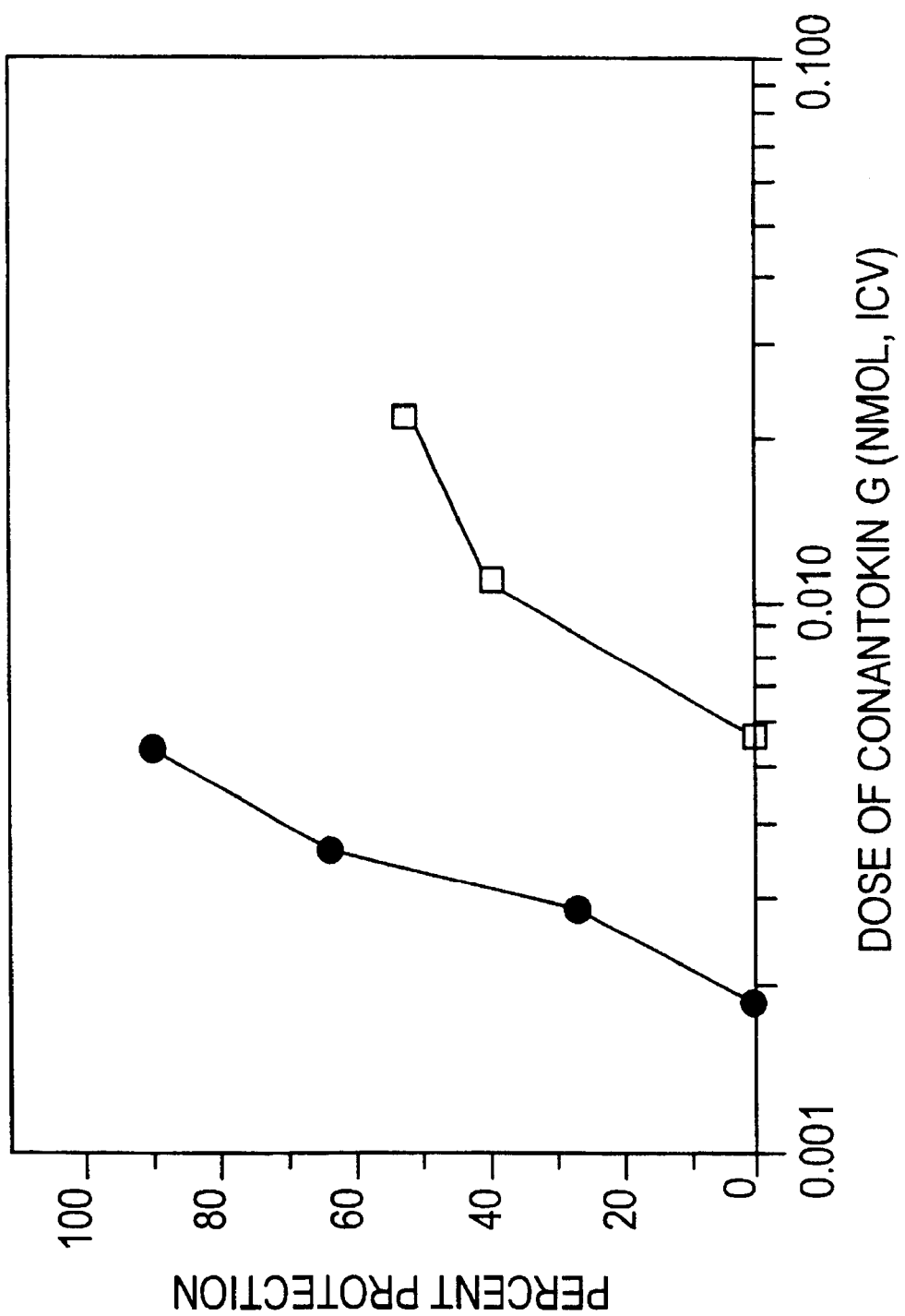
FIG. 5 shows the dose-response of the anticonvulsant activity of Con G at one (□) and three (●) minutes following i.c.v. administration to Frings audiogenic mice.

A dose-response of the anticonvulsant activity of Con G at one and three minutes following i.c.v. administration in this model is shown in FIG. 5. These data demonstrate that the median effective dose ($ED_{50}$) for anticonvulsant activity of Con G at one and three minutes was 0.023 nmol 0.004 mnol, respectively.

Example 11

In vivo Activity of Conantokin G in Frings Audiogenic Seizure-Susceptible Mice Following I.C.V. Administration In vivo anticonvulsant activity of Conantokin G was analyzed in Frings audiogenic seizure susceptible mice as described above with i.c.v. administration. Table 13 compares the median effective dose ($ED_{50}$), the median toxic dose ($TD_{50}$), rotorod minimal motor impairment and protective index ($PI=TD_{50}ED_{50}$) of Con G at one, three and thirty minutes following i.c.v. administration. In these studies, all rotorod minimal motor impairment tests were performed at 30 minutes.

TABLE 13

Time to Onset of Anticonvulsant Activity of Conantokin G: Efficacy, Minimal Motor Impairment and Protective Index Following I.C.V. administration to Frings Audiogenic Mice

| Test Substance | Time of Test (min) | Dose (nmol, i.c.v.) | | |
|---|---|---|---|---|
| | | $ED_{50}$ | $TD_{50}$ | PI |
| Con G | $1^{1,2}$ | 0.023 | 0.028 (0.022–0.035)[3] | 1.2 |
| Con G | 3 | 0.004 (0.003–0.004) | 0.028 (0.022–0.035) | 7.8 |
| Con G | 30 | 0.001 (0.001–0.002) | 0.028 (0.022–0.035) | 27 |

[1]N = 8 animals/group
[2]No animals exhibited minimal motor impairment at indicated doses at the time of test.
[3]95% confidence interval in parentheses.

At one minute following Con G administration, the $ED_{50}$, $TD_{50}$ and PI for anticonvulsant activity were 0.023 nmol, 0.028 nmol and 1.2, respectively. At three minutes following Con G administration, the $ED_{50}$, $TD_{50}$ and PI for anticonvulsant activity were 0.004 nmol, 0.028 nmol and 7.8, respectively. At 30 minutes following Con G administration, the $ED_{50}$, $TD_{50}$ and PI for anticonvulsant activity were 0.001 nmol, 0.028 nmol and 27, respectively. These data clearly show that the time to onset of Con G anticonvulsant activity following i.c.v. administration to Frings audiogenic mice was very rapid (within one to three minutes) with very low behavioral toxicity compared to prototypical antiseizure drugs in testing or on the market.

Example 12

In vivo Phencyclidine-Like Behavioral Effects of Conantokin G Following I.C.V. Administration The in vivo phencyclidine-like behavioral effects of Con G was assessed by the elevated platform test as described by Evoniuk et al. (1991). The platform test is a rapid method for evaluating the behavioral effects of phencyclidine-like dissociative anesthetics in mice. At 15 minutes following a Con G dose of 0.0225 nmol (i.c.v.) to mice, no drug-induced falls from the elevated platform were observed. Alternatively, as a control, a 44.5 nmol dose of MK 801 (dizocilpine) elicited 87.5% drug-induced falls from the elevated platform. Thus, Con G does not induce phencyclidine-like behavioral effects in mice. The results are shown in Table 14.

TABLE 14

Absence of Phencyclidine-Like Behavioral Effects Using Conantokin G Compared to MK 801: Activity in the Elevated Platform Test

| Test Substance | Maximum Dose Tested (nmol) | Percent Drug-Induced Falls from Elevated Platform |
|---|---|---|
| Con G | $0.0225^1$ (i.c.v.) | 0 |
| MK 801 | $44.5^2$ (i.p.) | 87.5 |
| MK 801 | 118.6 (i.p.) | 100 |
| $H_2O$ | 50 μl (i.p.) | 0 |

[1]$ED_{50}$, $TD_{50}$, PI as noted in Example 11.
[2]Dose used in these studies was the same as the minimum effective dose that induced ≧50% of animals to fall from elevated platform in Evoniuk et al. (1991).

Example 13

Comparison of Modes of Administration of Conantokin G

Figure 6:
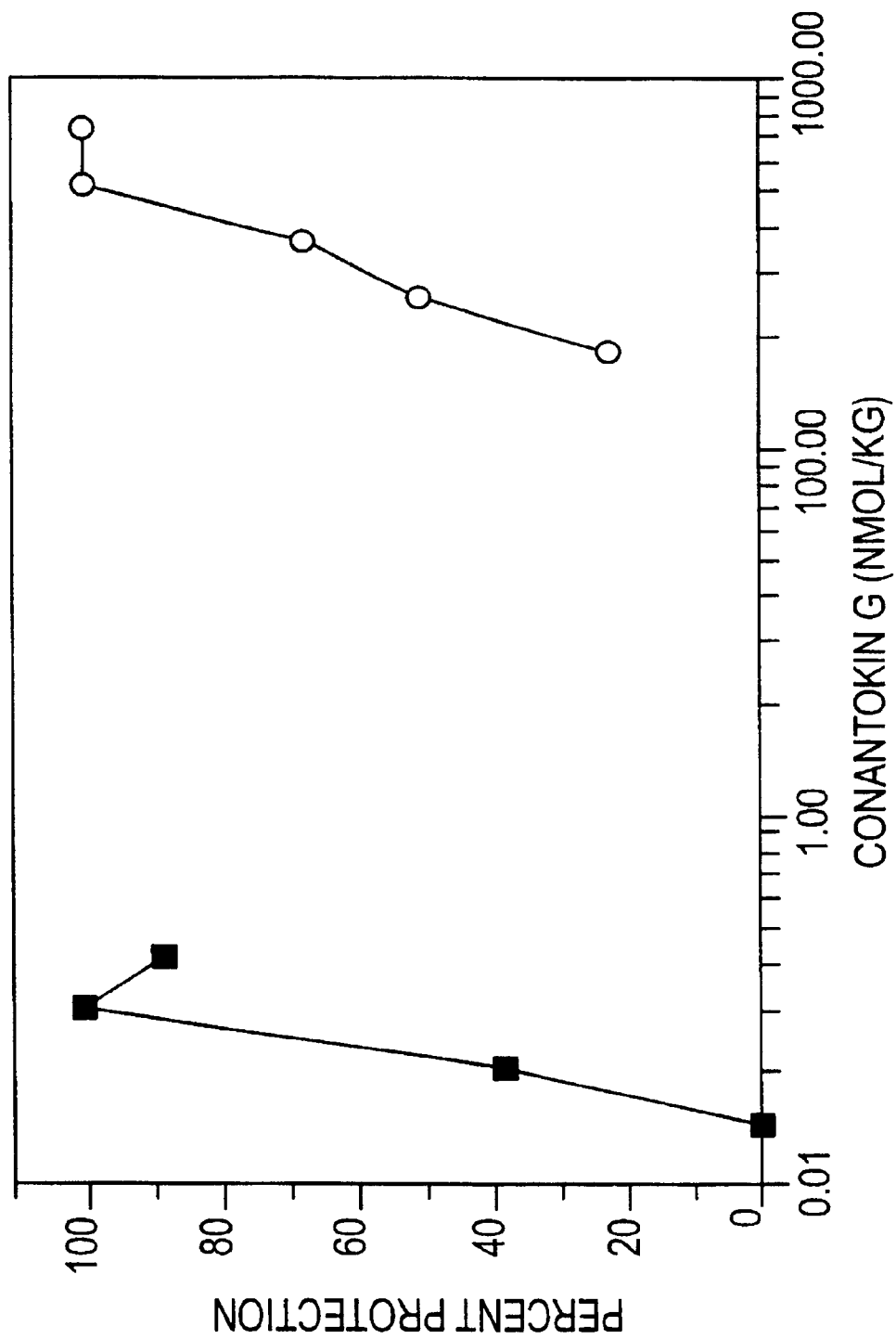
FIG. 6 shows the dose-dependent inhibition of audiogenic seizures following i.c.v. (■) or intravenous (i.v.) (○) administration of conantokin G.
Figure 7:
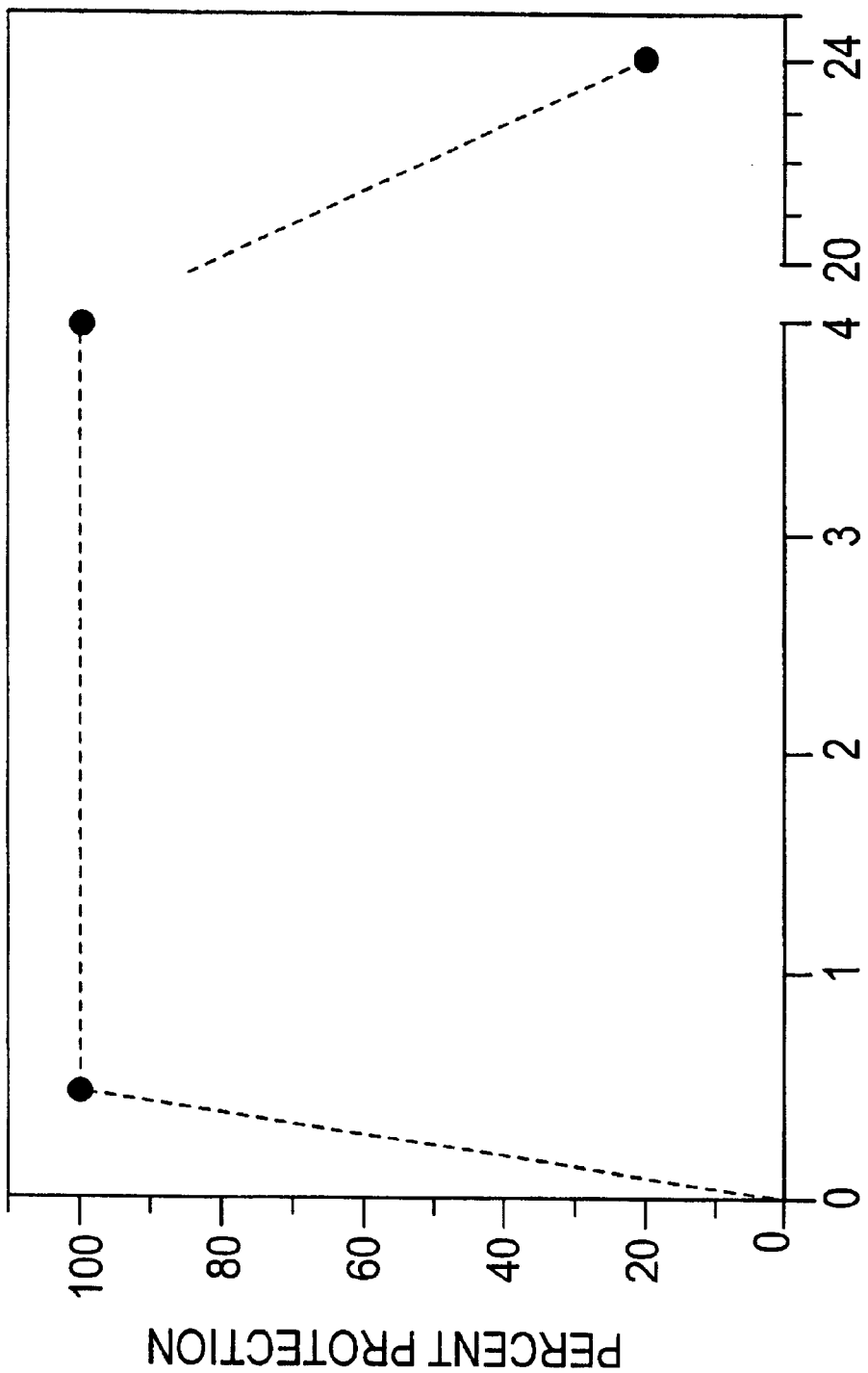
FIG. 7 shows the time-dependent inhibition of audiogenic seizures following i.v. administration of conantokin G.
Figure 8:
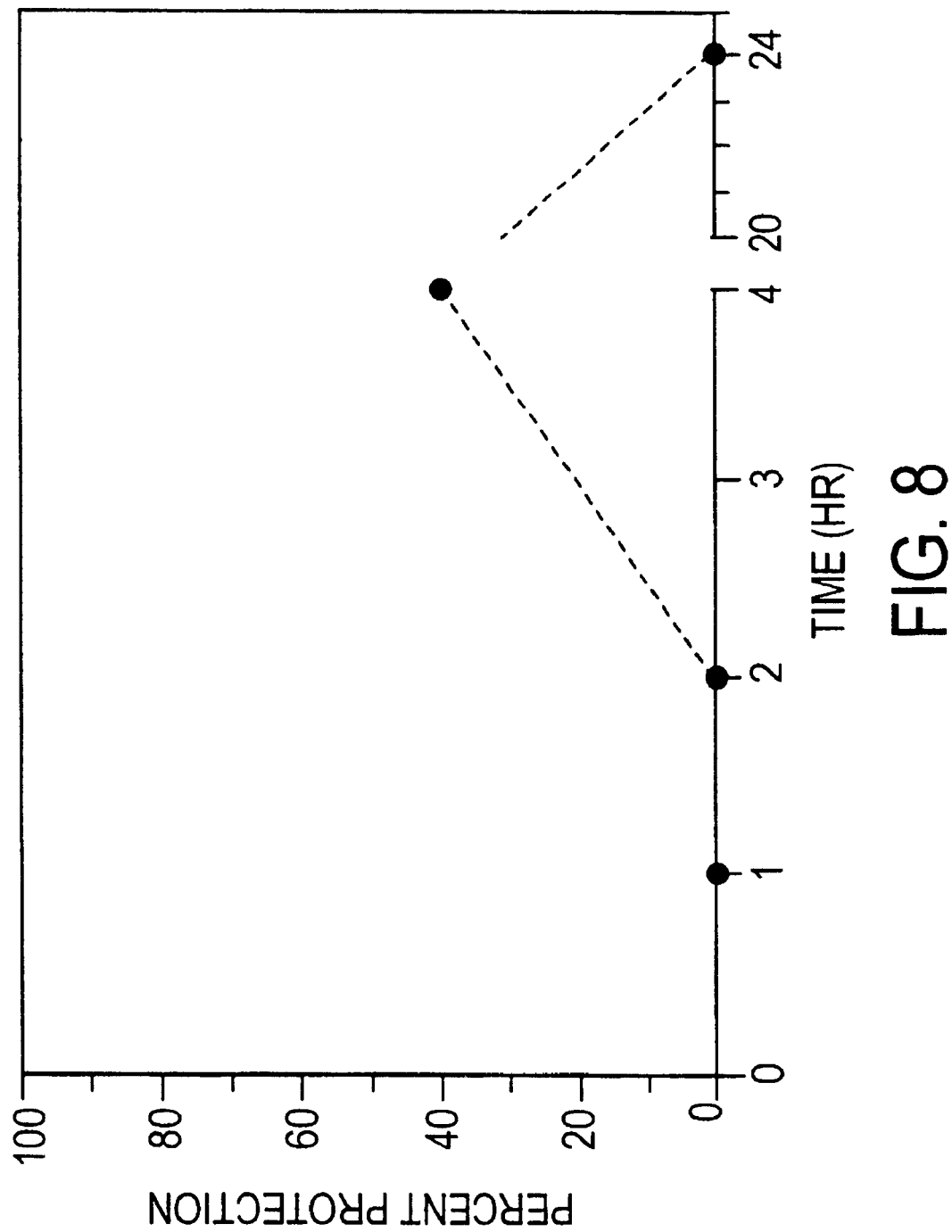
FIG. 8 shows the time-dependent inhibition of audiogenic seizures following per oral (p.o.) administration of conantokin G.

In vivo anticonvulsant activity of conantokin G when administered i.c.v., i.v. or p.o. was analyzed in Frings audiogenic mice as described above. The $ED_{50}$ at 30 minutes was determined to be 0.048 nmol/kg for the i.c.v. administration and 702 nmol/kg for the i.v. administration. The 95% confidence interval for these values are 0.027–0.072 for i.c.v. administration and 341–1246 for i.v. administration. FIG. 6 shows the dose-dependent inhibition of audiogenic seizures for i.c.v. and i.v. administration of Con G. The time-dependent inhibition of audiogenic seizures by Con G when administered i.v. (2650 nmol/kg) or p.o. (6623 nmol/kg) is shown in FIGS. 7 and 8, respectively.

Example 14

Comparison of In Vivo Activity of Conantokin G with Prototype Antiepileptic Drugs The in vivo anticonvulsant activity of Con G was compared to the anticonvulsant activities of several prototype antiepileptic drugs (AED) with i.c.v. administration in Frings audiogenic mice, as described above. The results are shown in Table 15. The protective index (PI) of Con G was significantly higher than the PI for the other drugs tested.

TABLE 15

Effect of Conantokin G Compared to Prototype Antiepileptic Drugs (AED) on Audiogenic Seizure-Sesceptibility Following i.c.v. Administration to Frings Mice

| Prototype AEDs | Time of Test (min)* | ED$_{50}$ nmol | TD$_{50}$ nmol | PI |
|---|---|---|---|---|
| Con G | 30, 15 | 0.001 (0.001–0.002) | 0.028 (0.022–0.035) | 27 |
| Con G | 3, 15 | 0.004 (0.003–0.004) | 0.028 (0.022–0.035) | 7.8 |
| Phenobarbitol | 5, 15 | 145 (105–186) | 68.8 (42.9–93.5) | 0.5 |
| Valproic Acid | 5, 5 | 566 (3707–7759) | >6000– <12,000 | 1.1–2.2 |
| Lamotrigine | 30, 15–60 | 146 (101–195) | >290 limit ofsolubility | >2.0 |
| Felbamate | 30, 15–60 | 5/8 protected at 525 4/8 protected at 630 | no up marked to | toxicity 630 | unable to determine |
| Topiramate | 15–240, 15–240 | >150 nmol | no limit marked ofsolubility | toxicity | unable to determine |

TD$_{50}$ = rotrod performance, minimal motor impairment measure of behavioral toxicity
95% confidence interval in parenthesis
PI = Protective Index (PI =TD$_{50}$/ED$_{50}$)
* = 1st time ED$_{50}$; 2nd time TD$_{50}$

Example 15

In Vivo Activity of Conantokin G in Pentylenetetrazole-Induced Threshold Seizure Model The in vivo activity of Con G was analyzed using timed intravenous infusion of pentylenetetrazole (White et al., 1995). At time to peak effect, the convulsant solution (0.5% pentylenetetrazole in 0.9% saline containing 10 U.S.P. units/ml heparin sodium) is infused into the tail vein at a constant rate of 0.34 ml/min. The time in seconds from the start of the infusion to the appearance of the first twitch and the onset of clonus is recorded for each drug treated or control animal. The times to each endpoint are converted to mg/kg of pentylenetetrazole for each mouse, and mean and standard error of the mean are calculated. The results are shown in Table 16. Administration of Con G i.c.v. at 18.75 pmol elevates the i.v. pentylenetetrazole seizure threshold.

TABLE 16

Conantokin G Elevates i.v. Pentylenetetrazole (PTZ) Seizure threshold

| | | PTZ, mg/kg | |
|---|---|---|---|
| Treatment | Dose, pmol | First Twitch | Clonus |
| Control | 0 | 29.9 ± 2.5 | 41.9 ± 4.8 |
| Conantokin G | 18.75 | 47.3 ± 7.8 | 75.8 ± 11.1 |

N = 7 (Control, 8 (Conantokin G)

Example 16

In Vivo Activity of Conantokin G in Parkinson's Disease Animal Model

Figure 9:
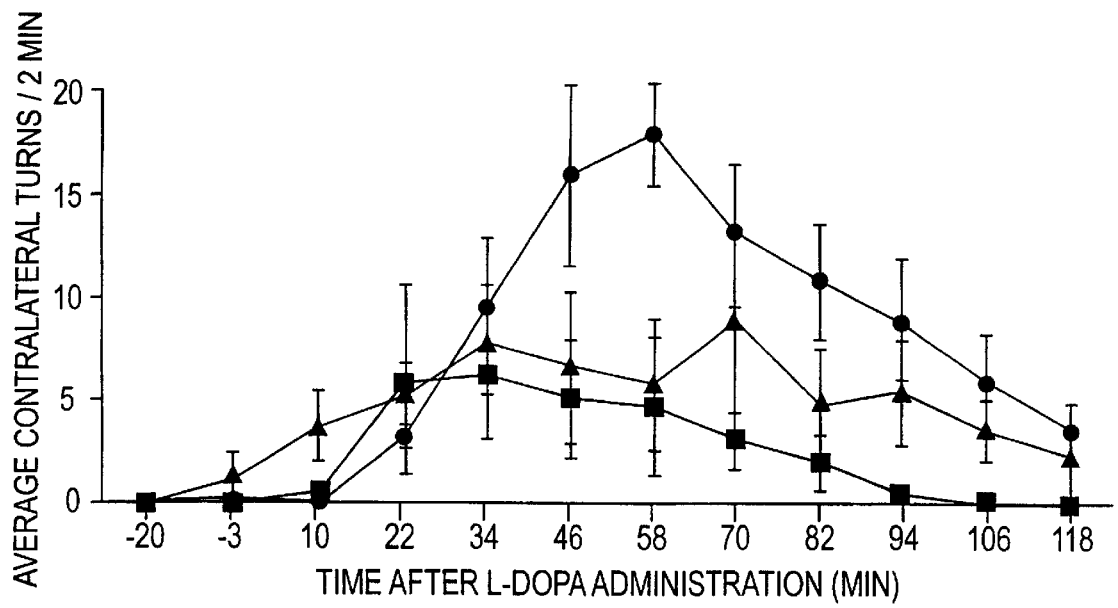
FIG. 9 shows the contralateral rotations following administration of 4 mg/kg L-DOPA (■), 4 mg/kg L-DOPA and 0.5 mM Con G (●) and 4 mg/kg L-DOPA and 5 mM Con G (▲) in a Parkinson's disease animal model.
Figure 10:
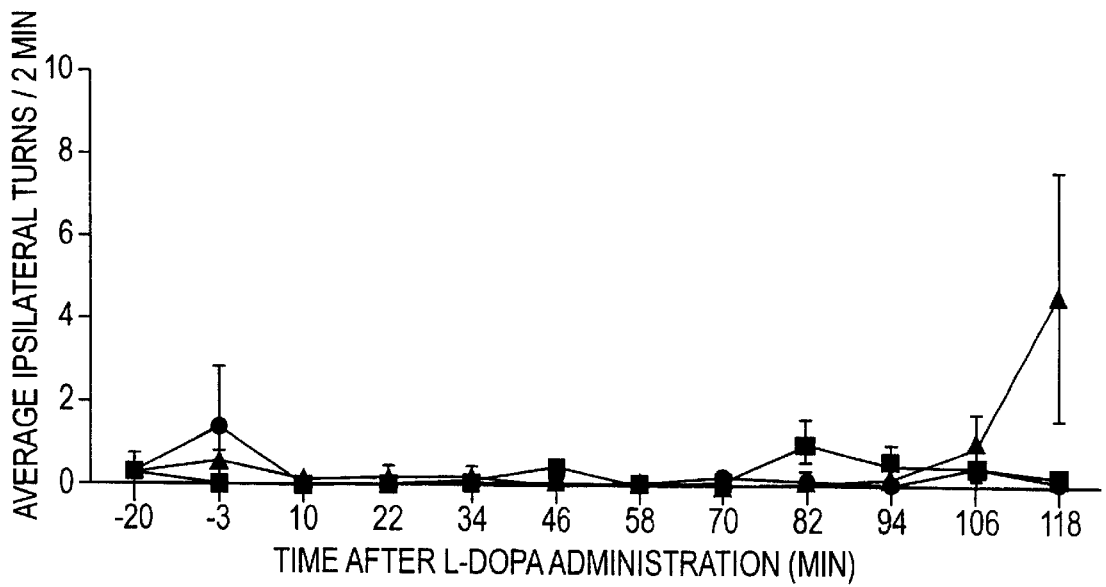
FIG. 10 shows the ipsilateral rotations following administration of 4 mg/kg L-DOPA (■), 4 mg/kg L-DOPA and 0.5 mM Con G (●) and 4 mg/kg L-DOPA and 5 mM Con G (▲) in a Parkinson's disease animal model.
Figure 11:
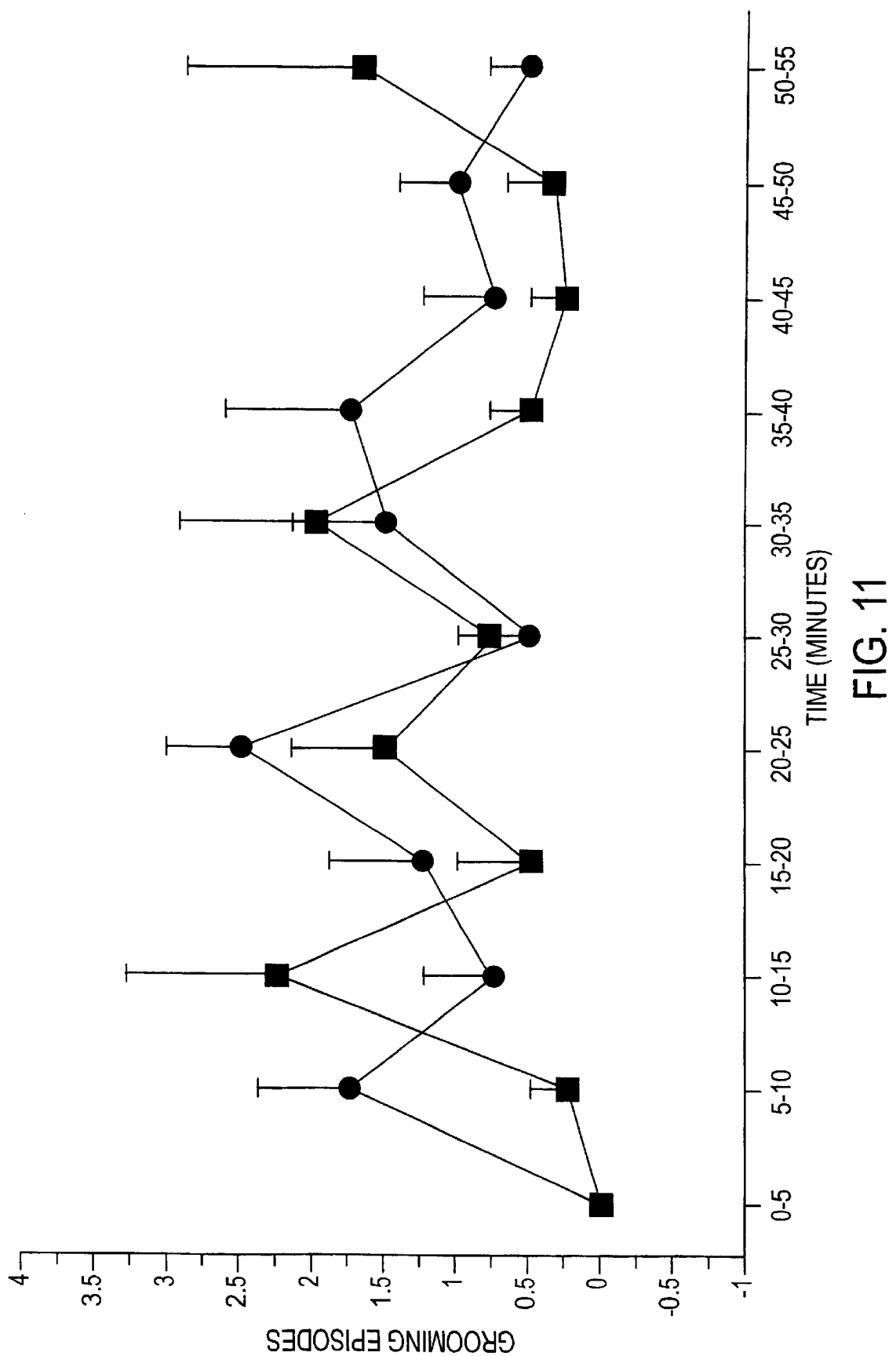
FIG. 11 shows the number of grooming episodes following administration of SKF 38393 (■) or the combination of SKF 38393 and Con G (●).
Figure 12:
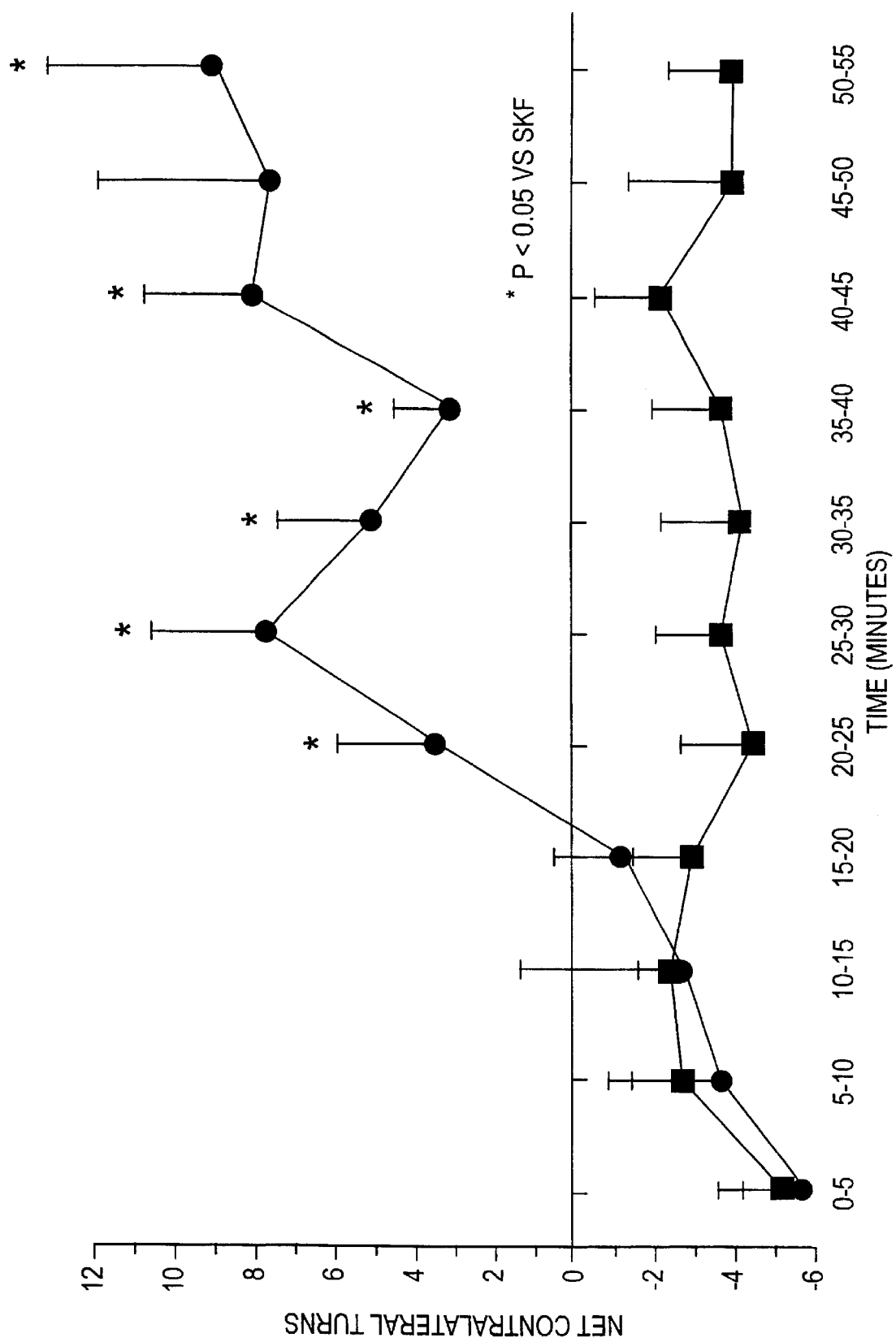
FIG. 12 shows the number of net contralateral turns following administration of SKF 38393 (■) or the combination of SKF 38393 and Con G (●). The asterisks indicate statistical significance at $p<0.05$.
Figure 13:
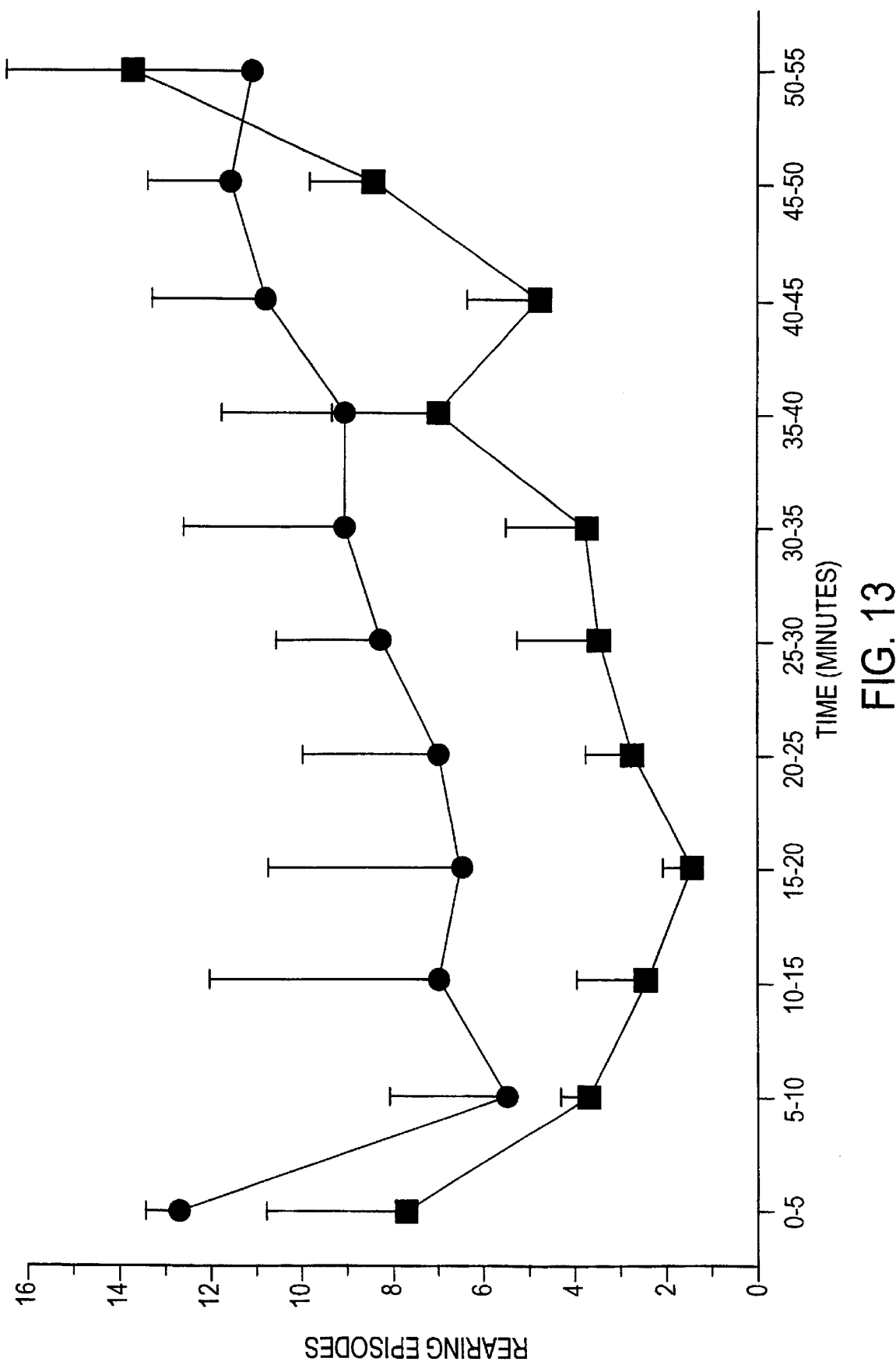
FIG. 13 shows the number of rearing episodes following administration of SKF 38393 (■) or the combination of SKF 38393 and Con G (●).
Figure 14:
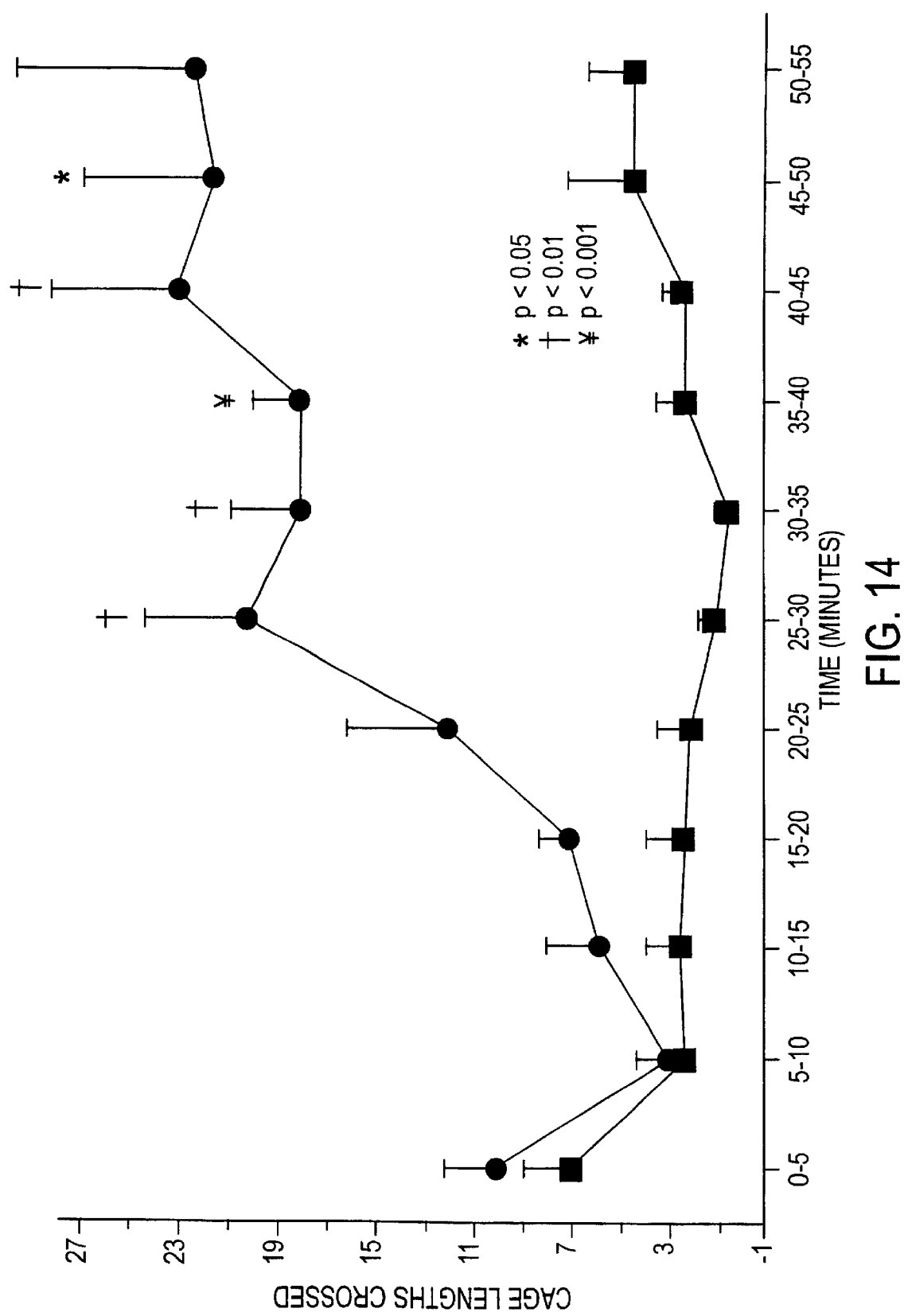
FIG. 14 shows the number of cage lengths crossed following administration of SKF 38393 (■) or the combination of SKF 38393 and Con G (●). Statistical significance is shown at $p<0.05$ (*), $p<0.01$ (†) or $p<0.01$ (¥).
Figure 15:
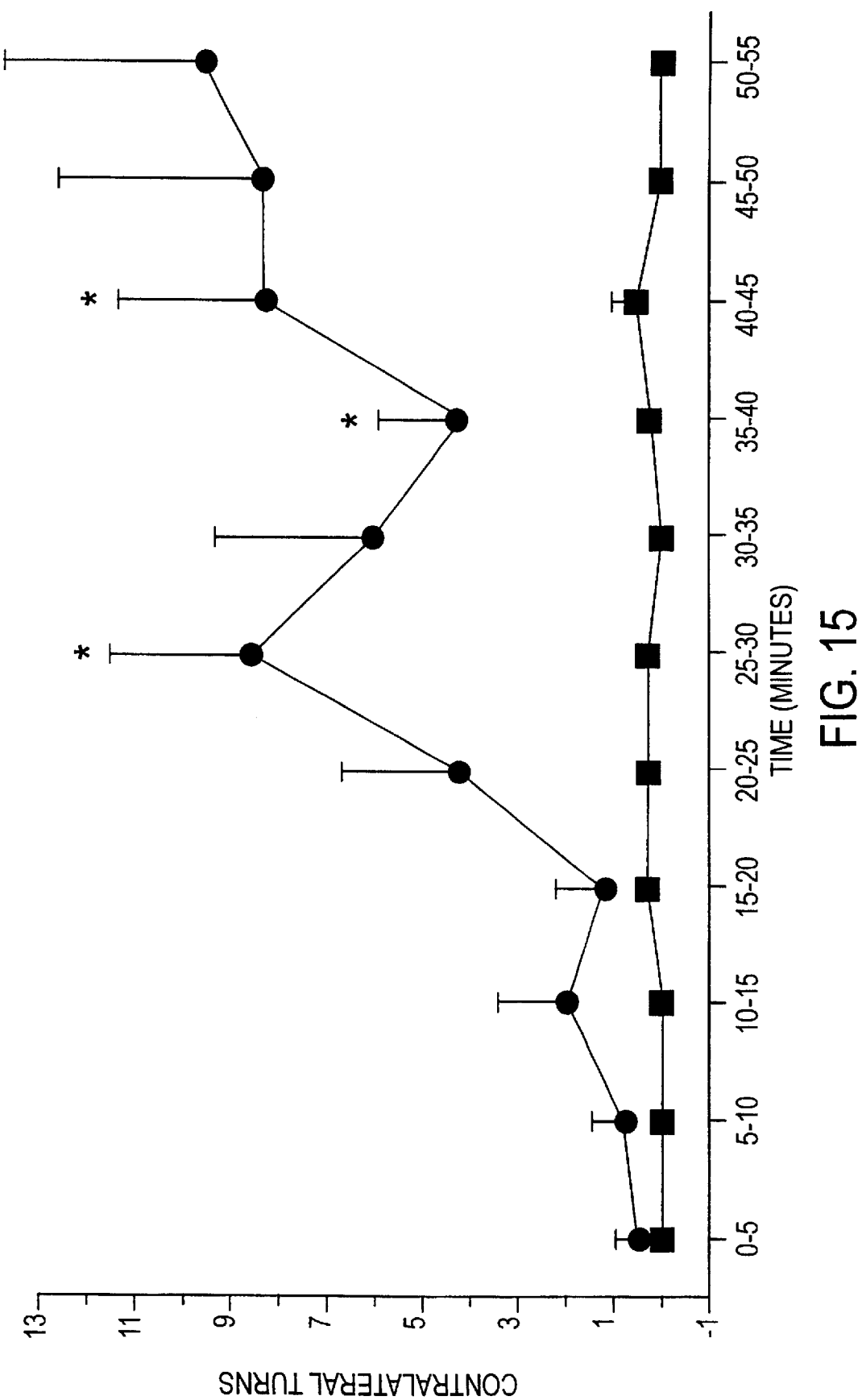
FIG. 15 shows the number of contralateral turns following administration of SKF 38393 (■) or the combination of SKF 38393 and Con G (●). The asterisks indicate statistical significance at $p<0.05$.
Figure 16:
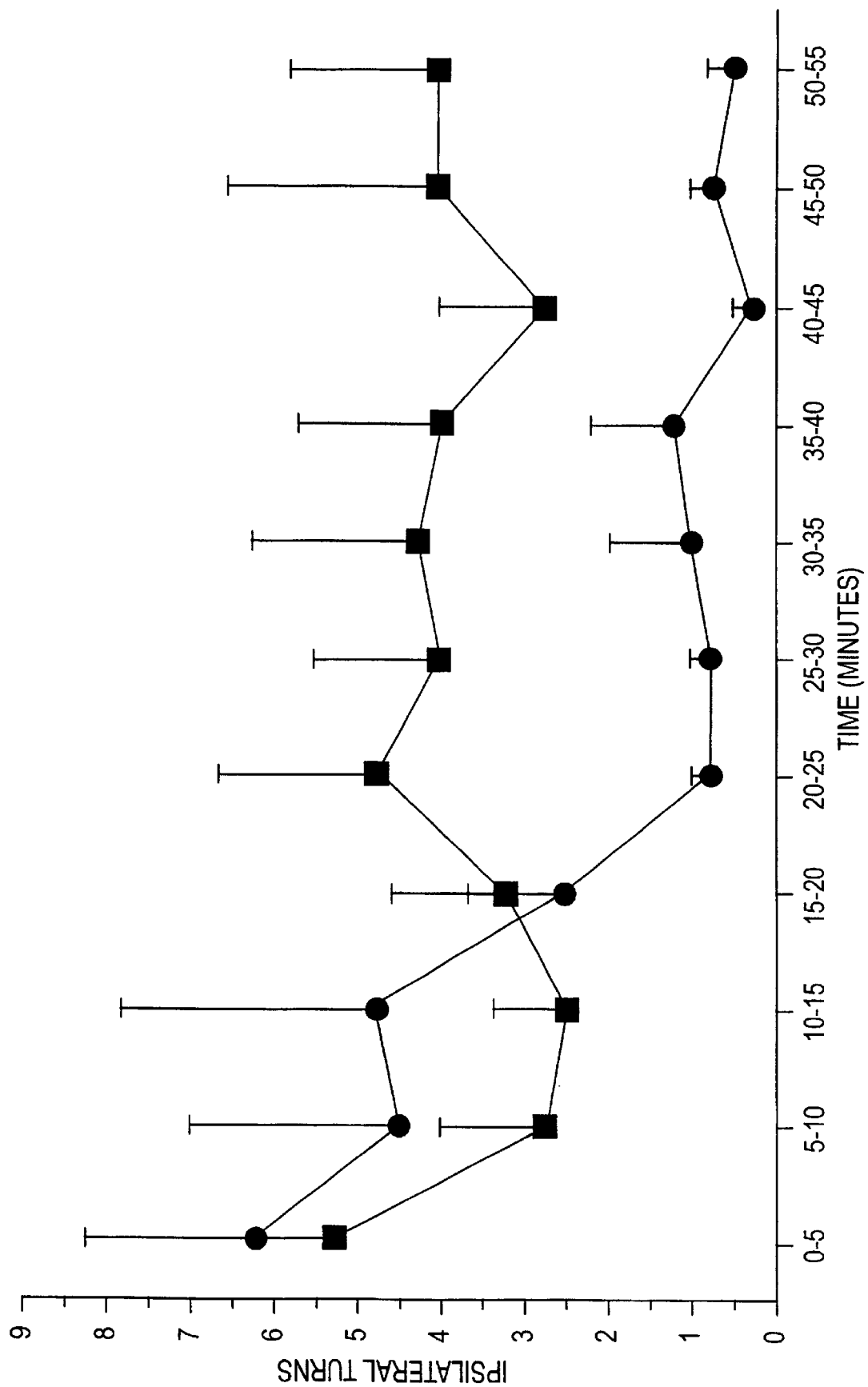
FIG. 16 shows the number of contralateral turns following administration of SKF 38393 (■) or the combination of SKF 38393 and Con G (●).

The anti-Parkinsonian potential of conantokin G was examined in rats with unilateral lesions of the nigrostriatal dopamine system. The unilateral lesions are created by local infusion of the neurotoxin 6-hydroxydopamine (6-OHDA) into the right substantia nigra of anesthetized rats. The rats recovered for two weeks at which time they are anesthetized and guide cannulae implanted into the brain, ending in the right lateral ventricle. The guide cannulae are kept patent with a stylet placed in the guide cannula. One week later, the rats are placed in a cylindrical Plexiglas® cage, the stylet is removed, and an infusion cannula is inserted into the guide. The infusion cannula is attached to a syringe on an infusion pump which delivered conantokin G (0.5 mM or 5.0 mM) or control vehicle at a rate of 1 μl/min for a total injection of 2 μl (1 nmol/2 μl). Fifteen minutes after the injection of conantokin G, L-Dopa (4 mg/kg ip) is injected. The number of full rotations contralateral and ipsilateral to the dopamine-depleted hemisphere is then counted for 2 minutes, every 10 minutes, for 2 hours. A video of the rats is also made to follow the behavioral potentiation of the treatment. The results are shown in FIGS. 9 and 10. These results show that there is clear potentiation of the L-Dopa activity with Con G. The video showed that the behavioral potentiation by Con G is very dramatic, especially the locomotor activity. The ability to elicit contralateral rotation in this animal model leads to the conclusion that the tested compounds reverse the behavioral deficits induced by dopamine depletion. In addition to the above tests, the in vivo activity of Con G in combination with SKF 38393 was compared with that of SKF 38393 alone. The results are shown in FIGS. 11–16. The combination of Con G and SKF 38393 demonstrated increased activity.

Example 17

Regulation of Striatal Output Pathways by NMDA-2B Receptors

Experimental Parkinsonism results in altered functional activity of striatal output pathways. Neurons projecting to the globus pallidus (indirect pathway) become overactive, resulting in increased inhibition of cortical regions involved in movement and movement initiation via processing through the basal ganglia-thalamo-cortical loop. Treatment with non-selective NMDA antagonists (Klockgether and Turski, 1990) or lesions of the glutamergic neurons of the subthalamic nucleus alleviate Parkinsonian symptoms in experimental models (Bergman et al., 1990). The identification of multiple subtypes of NMDA receptor subunits and their differential expression throughout the basal ganglia nuclei offers the potential of altering glutamatergic transmission with specific nuclei. Of the primary basal ganglia nuclei, the NR2B subunit is expressed almost exclusively in their striatum (Standaert et al., 1994).

The recent discovery of a class of conantokins with remarkable selectivity for NDMA receptors expressing the NR2B subunit offers a unique pharmacological tool for the investigation of the role of this NMDA receptor subtype in the regulation of basal ganglia circuits, and its potential as a target for the treatment of movement disorders such as Parkinsonism. Con R will be administered i.c.v. alone or in combination with SKF 38393 in unilateral 6-hydroxydopamine-lesioned rats, or in combination with eticlopride in uniesioned rats, to precisely examine the role of NR2B receptors on immediate early gene induction in striatonigral and striatopallidal neurons which specifically express dopamine DI or D2 receptors, respectively

Example 18

In Vivo Activity of Conantokin G in Animal Model of Urinary Incontinence

Female Wistar rats are anesthetized with urethane and, following tracheotomy (for ventilation after skeletal muscle paralysis) and jugular and carotid cannulation (for drug delivery and blood pressure recording, respectively), laminectomies are performed at C7-T2 and T11-S1 through a midline dorsal incision. The back is temporarily closed and the animal is placed abdomen up. A midline incision is made from the sternum to the pubis. The ureters are isolated, ligated and cut proximally, and saline soaked gauze wicks are positioned at the cut end to exit the abdominal incision for urine elimination.

A double lumen urethral catheter is passed through a cystotomy at the dome of the bladder and seated in the urethral opening at the level of the internal sphincter. A second, single lumen catheter is positioned, through its own cystotomy, into the bladder. Both catheters are tied in with suture, and connected to pressure recording transducers and filling/perfusion syringes via three-way stopcocks.

Following closing of the abdomen, the rat is placed onto its abdomen and the back incision reopened and sutured to a metal ring to form a pocket for oxygenated Krebs solution. The spinal cord is cut at C7 and L3. Silver wire electrodes are introduced into the cut ends at C7 (inserted caudally) and L3 (inserted rostrally) for sympathetic preganglionic stimulation. Spinal roots L6 and S1 are placed on a hook electrode for stimulation of parasympathetic preganglionic axons. A continuously oxygenated Krebs solution fills the dorsal pocket and bathe the spinal cord and roots.

Simultaneous, independent electrical stimulation is delivered a low levels to both sets of preganglionic pathways and independent adjustment of stimulus parameters is made to achieve maximal responses from the blood pressure (sympathetic preganglionic stimulus driven) and the bladder (parasympathetic preganglionic driven).

Conantokins are introduced intrathecally and changes in blood and bladder pressure responses under constant drive are monitored, recorded and taped. Control studies are made with hexamethonium bromide and all studies finish with hexamethoniun bromide administration.

Conatokin G was administered intrathecally at 0.3 nmol, 3.0 nmol and 30 nmol. The 0.3 nmol dose had no effect. The 3.0 nmol dose had no effect on bladder contraction amplitude, but increased frequency. This means that voiding was hampered at the level of the urethra. The 30 nmol dose eliminated all lower urinary tract activity. Similar effects were seen for conantokin T.

Figure 17:
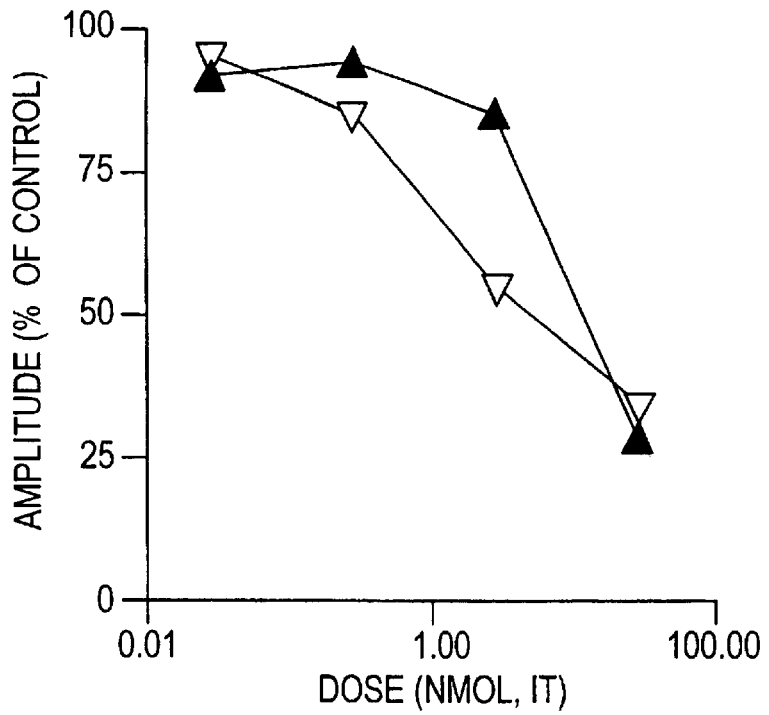
FIG. 17 shows the effect of Con G (▲) and Con T (▽) on bladder contraction amplitude.
Figure 18:
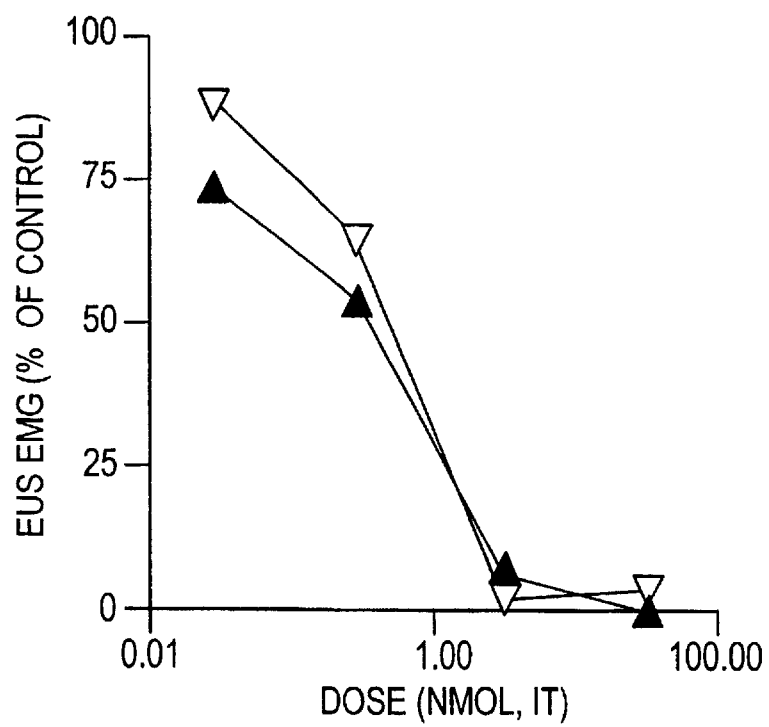
FIG. 18 shows the effect of Con G (▲) and Con T (▽) on EUS EM G activity.
Figure 19:
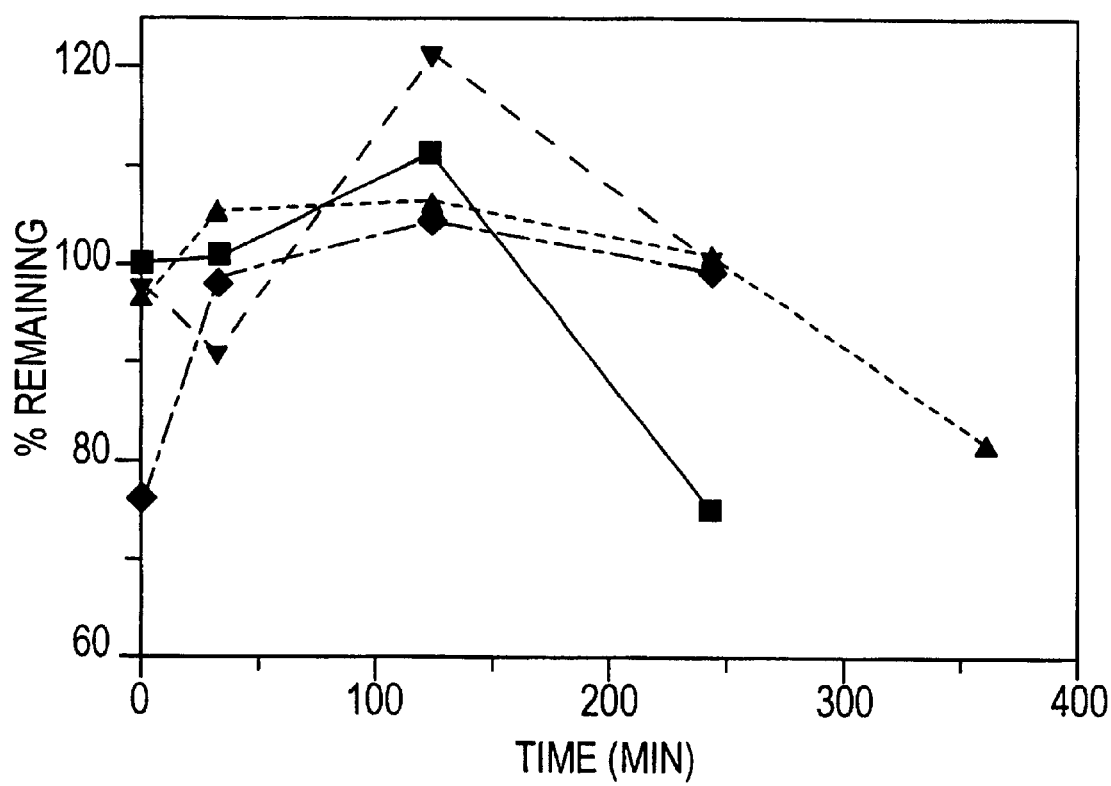
FIG. 19 shows the peptide stability of ECon G (■), Con G (▲), Con R (▼) and Con T (♦) in 20% Frings mouse serum.
Figure 20:
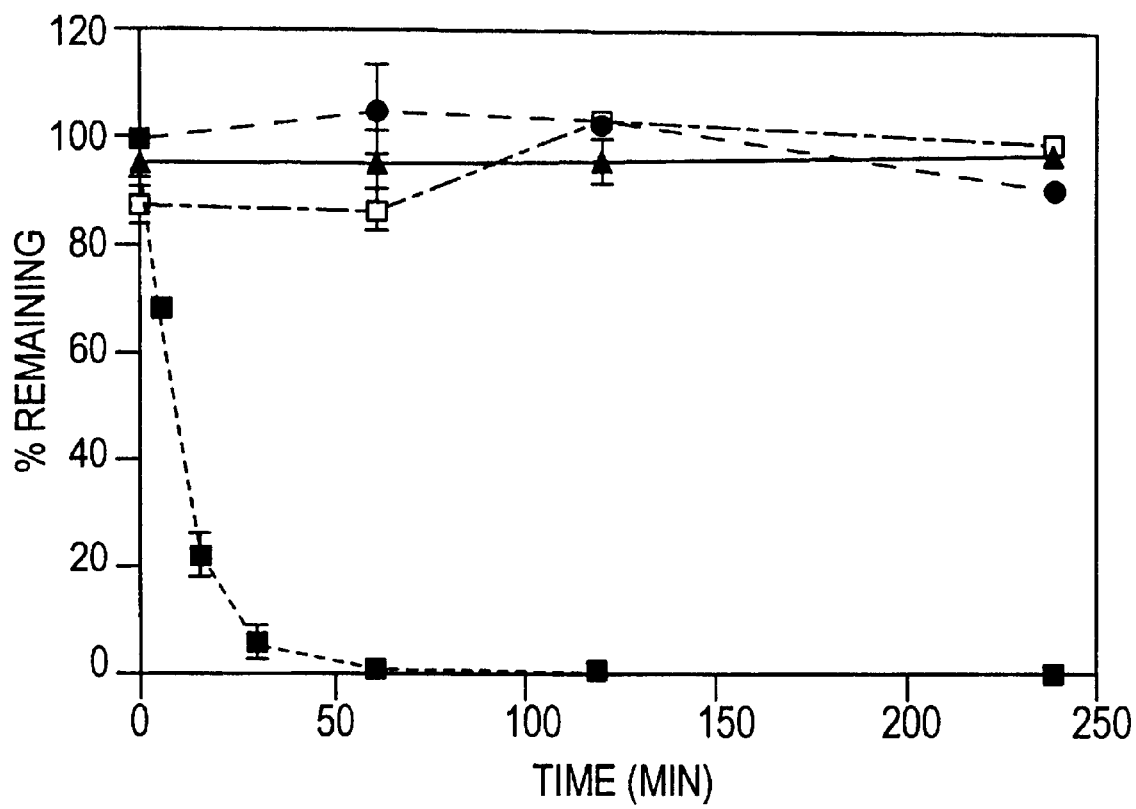
FIG. 20 shows the peptide stability of ECon G (■), Con G (▲), Con R (●) and Con T (□) in 20% Frings mouse liver homogenate.
Figure 21:
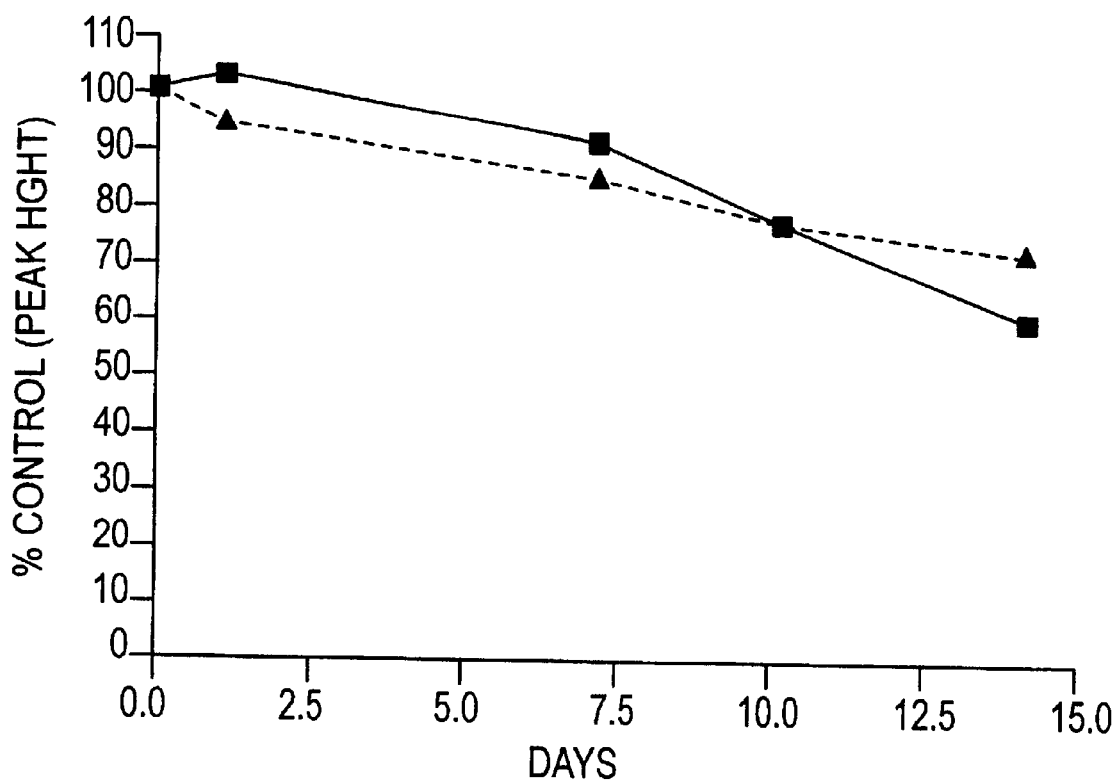
FIG. 21 shows the stability of conantokin G in physiological saline at pH 6.0 at 37° C. (■) and (▲).

Further effects of Con G and Con T on bladder contraction amplitude and on EUS EM G activity are shown in FIGS. 17 and 18. The conantokins appear to be more discriminatory in their inhibitory effect on striated sphincter than on bladder, compared to other NMDA antagonists. Thus, it is possible to dose the conantokins in such a manner to selectively decrease bladder/ sphincter dyssynergia in spinal cord-injured patients.

Example 19

Biological Activity of Conantokin Peptide Derivatives and Conantokin Peptide Chimeras Several conantokin peptide derivatives and conantokin peptide chimeras were prepared using conventional techniques and their inhibitory activity was measured using the spermine-stimulated [$^3$H]MK-801 binding assay as described by Zhou et al. (1996). The results are shown in Table 17. A value for $IC_{50}$ of <100 $\mu$M has been found to have activity in the in vivo assays described herein.

TABLE 17

Inhibitory Activity of Con G Derivatives and Chimeras

| Test Substance | Sequence | | | | | | | | | | | | | | | | | $IC_{50}$ ($\mu$M) |
|---|---|---|---|---|---|---|---|---|---|---|---|---|---|---|---|---|---|---|
| Con G | G | E | γ | γ | L | Q | γ | N | Q | γ | L | I | R | γ | K | S | N | 0.195 |
| $A^3$ | | | A | | | | | | | | | | | | | | | 9.1 |
| $Y^3$ | | | Y | | | | | | | | | | | | | | | 0.96 |
| $S^3$ | | | S | | | | | | | | | | | | | | | 3.6 |
| $S_p^3$ | | | $S_p$ | | | | | | | | | | | | | | | 0.9 |
| $A^4$ | | | | A | | | | | | | | | | | | | | ≥20 |
| $S^4$ | | | | S | | | | | | | | | | | | | | ≥20 |
| $S_p^4$ | | | | $S_p$ | | | | | | | | | | | | | | ≥20 |
| $E^4$ | | | | Y | | | | | | | | | | | | | | ≥20 |
| $A^7$ | | | | | | | A | | | | | | | | | | | 0.045 |
| $Y^7$ | | | | | | | Y | | | | | | | | | | | 0.96 |
| $S^7$ | | | | | | | S | | | | | | | | | | | 0.25 |
| $S_p^7$ | | | | | | | $S_p$ | | | | | | | | | | | 1.2 |
| $A^{10}$ | | | | | | | | | | A | | | | | | | | 1.1 |
| $S^{10}$ | | | | | | | | | | S | | | | | | | | 1.8 |
| $S_p^{10}$ | | | | | | | | | | $S_p$ | | | | | | | | 0.56 |
| $A^{14}$ | | | | | | | | | | | | | | A | | | | 0.16 |

TABLE 17-continued

Inhibitory Activity of Con G Derivatives and Chimeras

| Test Substance | Sequence | | | | | | | | | | | | | | | | | $IC_{50}$ ($\mu M$) |
|---|---|---|---|---|---|---|---|---|---|---|---|---|---|---|---|---|---|---|
| $S^{14}$ | | | | | | | | | | | | | | | S | | | 0.16 |
| $S_p^{14}$ | | | | | | | | | | | | | | | $S_p$ | | | 1.59 |
| $A^7,Y^{10}$ | | | | | | A | | | Y | | | | | | | | | 0.079 |
| $A^{7,10,14}$ | | | | | | A | | | A | | | | | | A | | | 0.088 |
| $E^{7,10,14}$ | | | | | | E | | | E | | | | | | E | | | ≧20 |
| $A^{2,7,10,14}$ | | A | | | | A | | | A | | | | | | A | | | ND |
| $A^{3,7,10,14}$ | | | A | | | A | | | A | | | | | | A | | | ND |
| $A^{4,7,10,14}$ | | | | A | | A | | | A | | | | | | A | | | ND |
| $Y^3,S^4,A^{7,10,14}$ | | | Y | S | | A | | | A | | | | | | A | | | ND |
| Con G | G | E | γ | γ | L | Q | γ | N | Q | γ | L | I | R | γ | K | S | N | 0.195 |
| (1–10) | | | | | | | | | | | Δ | Δ | Δ | Δ | Δ | Δ | Δ | ND |
| $(A^{7,10,14})$5–17 | Δ | Δ | Δ | Δ | | A | | | A | | | | | A | | | | ND |
| 5–17 | Δ | Δ | Δ | Δ | | | | | | | | | | | | | | ND |
| $(A^{10,14})$6–17 | Δ | Δ | Δ | Δ | Δ | | | | A | | | | | A | | | | ND |
| $(A^{14})$12–17 | Δ | Δ | Δ | Δ | Δ | Δ | Δ | Δ | Δ | Δ | Δ | | | A | | | | ND |
| 12–17 | Δ | Δ | Δ | Δ | Δ | Δ | Δ | Δ | Δ | Δ | Δ | | | | | | | ND |
| $(A^{7,10,14})$1–16 | | | | | | A | | | A | | | | | A | | | Δ | 0.037 |
| $(A^{7,10,14})$1–15 | | | | | | A | | | A | | | | | A | | Δ | Δ | 0.034 |
| $(A^{7,10,14})$1–14 | | | | | | A | | | A | | | | | A | Δ | Δ | Δ | 0.232 |
| $(A^{7,10})$1–13 | | | | | | A | | | A | | | | | Δ | Δ | Δ | Δ | 0.253 |
| $(A^{7,10})$1–12 | | | | | | A | | | A | | | | Δ | Δ | Δ | Δ | Δ | 0.30 |
| $(A^{7,10,14})$2–17 | Δ | | | | | A | | | A | | | | | A | | | | inactive |
| $(A^{7,10,14})$3–17 | Δ | Δ | | | | A | | | A | | | | | A | | | | inactive |
| $(A^{7,10,14})$4–17 | Δ | Δ | Δ | | | A | | | A | | | | | A | | | | inactive |
| $(A^{7,10,14})$5–17 | Δ | Δ | Δ | Δ | | A | | | A | | | | | A | | | | inactive |
| $(A^{7,10,14})$6–17 | Δ | Δ | Δ | Δ | Δ | A | | | A | | | | | A | | | | inactive |
| Con G(T)$_2$ | | Y | Q | K | M | L | | | | | | | | | | | | ND |
| Con G(L)$_4$ | | | | | | | | | | | | | D | A | V | N | | ND |
| Con G(T)$_{2-3}$ | | Y | Q | K | M | L | N | L | | | | | | | | | | ND |
| Con G(R)$_{2-3}$ | | V | A | K | M | AA | | A | | | | | | | | | | ND |

All derivatives have an amide C-terminal. γ is γ-carboxyglutamic acid. $S_p$ is phosphoserine. Δ indicates a deletion of residue. ND is not determined.

Example 20

Biological Stability of Conantokins

The stability of Con G, Con T, Con R and several synthetic derivatives was determined in different biological media comprising serum (FS, 20%) and homogenates of liver (FL, 5%), kidney (FK, 25%) and brain (FB, 25%) from Frings audiogenic mice. The stability of Con G in normal saline as pH ≈6 was also examined The biological fluid was diluted to appropriate percentage with RPMI-1640 cell culture media and preincubated for 15 min at 37° C. in water bath. Peptides (1 mg/ml stock) were added to the biological media to a concentration of 50 $\mu$g/ml and incubated at 37° C. Peptide aliquots (100 $\mu$l) were removed at timed intervals and added to 200 $\mu$l of ice cold 6% trifluoroacetic acid (TFA) and chilled on ice at least 15 min. Supernatant was recovered following centrifugation at 14,000×g for 3 min and frozen until analysis. Two hundred $\mu$l sample was injected into a HPLC system comprising 2 Dynamax Model SD-300 solvent delivery pumps, Rheodyne injection port, 5 ml injection loop, mixer and bubble suppression unit (Dynamax), Vydac T18TPS4 protein and peptide $C_{18}$ column with precolumn and prefilter, Dynamax absorbance detector Model UV-D11 and Dell Pentium computer with Dynamax chromatography software. The mobile phase used 0.1% TFA/$H_2O$ as Buffer A and 0.1% TFA/acetonitrile as Buffer B. The following gradient was utilized:

| Time (min) | Flow Rate (ml/min) | % Buffer A | % Buffer B |
|---|---|---|---|
| 0 | 1 | 95 | 5 |
| 3 | 1 | 95 | 5 |
| 25 | 1 | 45 | 55 |
| 27 | 1 | 45 | 55 |
| 29 | 1 | 5 | 95 |
| 33 | 1 | 5 | 95 |

The peak height and retention time was measured with Dynamax software. The results are shown in FIGS 19 and 20. Con G, [$Ala^7$]Con G, Con-T and Con R were stable in all biological media for up to 4 hours. The derivatives ECon G and ECon R (Gla residues replaced by Glu residues demonstrated rapid degradation in FL ($T_{1/2}$=25.5 sec and 2.4 min, respectively). The derivative ECon G demonstrated rapid degradation in FB ($T_{1/2}$=1.6 min). The results for the stability of Con G in normal saline is shown in FIG. 21. Approximately 60% of the Con G is left after 14 days.

Example 21

In vivo Activity of Conantokins on Preliminary Screening

The conantokins were originally described as producing a sleep-like state in mice younger than two weeks old (Haack et al., 1990). The conantokins are screened for biological activity using a modified form of this test. Several measures are assessed to measure the degree of the sleep-like state. Catalepsy, sleepy and righting reflex tests are designed to quantify the "sleep-like" behavior noted by Rivier et al.

(1987). In all three assays, young (<2 weeks old) mice are given a free-hand i.c.v. dose (100 pmol/g in 10 μl) of a compound. Behaviors are assessed at 30 and 60 minutes post-injection.

Catalepsy Test: Young mice are positioned such that the two front paws are placed on an overturned Petri dish. A mouse is considered cataleptic if it fails to remove its paws in a 30 second period. Sleepy Test: Young mice are observed without interference. If no activity is noted, the animal is nudged with a gloved finger. A mouse is considered "sleepy" if it makes no attempt to move away from the finger. Righting Reflex: Young mice are positioned on their backs with legs in the air. A mouse is considered to have lost its "righting reflex" if it fails to right itself (return to its normal position with paws on the floor) in 10 seconds, thus "3/4" means three out of four mice lost righting reflex. In general, the ability of relatively high doses of conantokins to induce a sleep-like state is correlated with affinity and efficacy in the spermine-stimulated [$^3$H]MK-801 binding assay described in Example 19. The results are shown in Table 18.

TABLE 18

| Conantokin dose[1] | Catalepsy Test[a] | | Sleepy Test[b] | | Righting Reflex[c] | |
|---|---|---|---|---|---|---|
| | 30 min | 60 min | 30 min | 60 min | 30 min | 60 min |
| Con G | 4/4 | 2/4 | 4/4 | 4/4 | 2/4 | 2/4 |
| Con T | 3/4 | 1/4 | 4/4 | 4/4 | 2/4 | 2/4 |
| Con R | 2/3 | 2/3 | 2/3 | 2/3 | 2/3 | 2/3 |
| Con L | 4/4 | 3/4 | 4/4 | 4/4 | 2/4 | 3/4 |
| Con Oc | 0/3 | 0/3 | 2/3 | 0/3 | 0/3 | 0/3 |
| Saline | 0/2 | 0/2 | 0/2 | 0/2 | 0/2 | 0/2 |

[1]~2 week old mice, 5–7 g, sex not checked, i.c.v. dose of 100 pmol/g (600 pmol in 12 μl) or 12 μl of normal 0.9%) saline
[a]positive if mice leave forepaws on Petri dish for >30 s
[b]positive if mice do not respond by moving away or sniffing after a finger poke
[c]positive if mice fail to right themselves in <10 s Example 22

In vivo Activity of Conantokins in Pain Models

The anti-pain activity of conantokin is shown in several animal models. These models include the nerve injury model (Chaplan, et al., 1997), the nocioceptive response to s.c. formalin injection in rats (Codene, 1993) and an NMDA-induced persistent pain model (Liu, et al., 1997). In each of these models it is seen that the conantokin peptides, conantokin peptide derivatives and conantokin peptide chimeras have analgesic properties.

More specifically, this study evaluates the effect of intrathecal administration of conantokins in mice models of nocioceptive and neuropathic pain. For nocioceptive pain, the effect of the conantokins is studied in two different tests of inflammatory pain. The first is the formalin test, ideal because it produces a relatively short-lived, but reliable pain behavior that is readily quantified. There are two phases of pain behavior, the second of which is presumed to result largely from formalin-evoked inflammation of the hind paw. Conantokins are administered 10 minutes prior to injection of formalin. The number of flinches and/or the duration of licking produced by the injection is monitored. Since the first phase is presumed to be due to direct activation of primary afferents, and thus less dependent on long term changes in the spinal cord, the conantokins are presumed to have greatest effect on the magnitude of pain behavior in the second phase.

The mechanical and thermal thresholds in animals that received an injection of complete Freund's adjuvant into the hind paw are also studied. This produces a localized inflammation including swelling of the hind paw and a profound decrease in mechanical and thermal thresholds, that are detected within 24 hours after injection. The changes in thresholds in rats that receive the conantokins are compared with those of rats that receive vehicle intrathecal injections.

To evaluate the contribution of long term, NMDA receptor-mediated changes to neuropathic (i.e., nerve injury-induced) behavior, a modification of the Seltzer model of pain that has been adapted for the mouse is used. A partial transection of the sciatic nerve is first made. This also produces a significant drop in mechanical and thermal thresholds of the partially denervated hind paw. In general, the mechanical changes are more profound. They peak around 3 days after surgery and persist for months.

An important issue is whether the drugs are effective when administered after the pain model has been established, or whether they are effective only if used as a pretreatment. Clearly, the clinical need is for drugs that are effective after the pain has developed. To address this issue, animals are studied in which the conantokin is administered repeatedly, after the inflammation (CFA) or nerve injury has been established. In these experiments, the conantokins are injected daily by the intrathecal (i.t.) route. The mechanical and thermal thresholds (measured, respectively, with von Frey hairs in freely moving animals and with the Hargreave's test, also in freely moving animals) are repeated for a 2 to 4 week period after the injury is induced and the changes in pain measured monitored over time.

It will be appreciated that the methods and compositions of the instant invention can be incorporated in the form of a variety of embodiments, only a few of which are disclosed herein. It will be apparent to the artisan that other embodiments exist and do not depart from the spirit of the invention. Thus, the described embodiments are illustrative and should not be construed as restrictive.

LIST OF REFERENCES

Abiko, H. et al. (1986). Protective effect of phenytoin and enhancement of its action by combined administration of mannitol and vitamin E in cerebral ischemia. *Brain Res.* 38:328–335.

Aldrete, J. A. et al. (1 979). Effect of pretreatment with thiopental and phenytoin on postischemic brain damage in rabbits. *Crit. Care Med.* 7:466–470.

Ascher, P. and Nowak, L. (1986). Calcium permeation of the channels activated by N-methyl-D-aspartate (NMDA) in mouse central neurons. *J. Physiol.* 377:35p.

Bach, F. W. (1994). Studies on the spinal pharmacology of a new model of allydonia. *Ann. Neurol.* 36:288A.

Bergman, H. et al. (1990). Reversal of experimental Parkinsonism by lesions of the subthalamic nucleus. *Science* 249:1436–1438.

Bilsky E. J., et al. (1996). Competitive and non-competitive NMDA antagonists block the development of antinociceptive tolerance to morphine, but not to selective mu or delta opioid agonists in mice. *Pain* 68:229–237.

Bliss, et al. (1993). *Nature* 361:31.

Bodansky et al. (1966). *Chem. Ind* 38:1597–98.

Bormann, J. (1989). Memantine is a potent blocker of N-methyl-D-aspartate (NMDA) receptor channels. *Euro. J. Pharmacol.* 166:591–592.

Bowyer, J. F. (1982). Phencyclidine inhibition of the rate of kindling development. *Esp. Neurol.* 75:173–175.

Chandler, P. et al. (1993). Polyamine-like Actions of Peptides Derived from Conantokin-G, an N-methyl-D- aspartate (NMDA) Antagonist. *J. Biol. Chem.* 268:17173–17178.

Chaplan S. R. (1997). Efficacy of spinal NMDA receptor antagonism in formalin hyperalgesia and nerve injury evoked allodynia in the rat. *J Pharmacol. Exp. Ther.* 280:829–838.

Chapman, V. (1994). Bi-directional effects of intrathecal NMDA and substance P on rat dorsal dorn neuronal responses. *Neurosci. Lett.* 178:90–94.

Cline, H. T. et al. (1987). N-Methyl-D-aspartate receptor antagonist desegregates eye-specific stripes. *Proc. Natl. Acad. Sci. USA* 84:4342–4345.

Codere, T. J. (1993). *Eur. J. Neurosci.* 5:390–393.

Codere, T. J. and Meizack, R. (1992). The contribution of excitatory amnio acids to central sensitization and persistent nociception after formalin-induced tissue injury. *J Neurosci.* 12:3665–3670.

Coderre, T. J. and Van Emple, I. (1992). The utility of excitatory amino acid (EAA) antagonists as analgesic agents. I. Comparison of the antinociceptive activity of various classes of EAA antagonists in mechanical, thermal and chemical nonciceptive tests. *Pain* 59:345–352.

Collinridge, G. L. et al. (1983). Excitatory amino acids in synaptic transmission in the Schaffer collateral-commissural pathway of the rat hippocampus. *J. Physiol.* 334:3446.

Cruz, L. J. et al. (1987). Conus geographus toxins that discriminate between neuronal and muscle sodium channels. *J. Biol. Chem.* 260:9280–9288.

Davies, S. N. and Lodge, D. (1987). Evidence for involvement of N-methylaspartate receptors in "wind up" of class 2 neurones in the dorsal horn of the rat. *Brain Res.* 424:402–406.

Dickenson, A. H. and Sullivan, A. F. (1987). Evidence for a role of the NMDA receptor in the frequency dependent potentiation of deep rat dorsal horn nociceptive neurones following C fibre stimulation. *Neuropharmacology* 26:1235–1238.

Dougherty, P. M. and Willia, W. D. (1991). Modification of the responses of primate spinothalamic neurons to mechanical stimulation by excitatory amino acids and an N-methyl-D-aspartate antagonist. *Brain Res.* 542:15–22.

Doyle, D. D. et al. (1993). Divalent cation competition with [$^3$H]saxitoxin binding to tetrodotoxin-resistant and -sensitive sodium channels. *J. Gen. Physiol.* 101:153–182.

Dudley, S. C. et al. (1995). A $\mu$-Conotoxin-Insensitive Na$^+$ Channel Mutant: Possible Localization of a Binding Site at the Outer Vestibule. *Biophys. J.* 69:1657–1665.

Dunbar, S. and Yaksh, T. L. (1996). Concurrent spinal infusion of MK801 blocks spinal tolerance and dependence induced by chronic intrathecal morphine in the rat. *Anesthesiology* 84:1177–1188.

Dunham, M. S. and Miya, T. A. (1957). *J. Am. Pharm. Ass. Sci. Ed.* 46:208.

Elliott, K. et al. (1994). The NMDA receptor antagonists, LY274614 and MK-801, and the nitric oxide synthase inhibitor, NG-nitro-L-arginine, attenuate analgesic tolerance to the mu-opioid morphine but not to kappa opioids. *Pain* 56:69–75.

Evoniuk et al. (1991). *Psychopharmacology* 105:125–128.

Finney, D. J. (1971). *Probit Analysis,* Cambridge University Press, London.

Gray, W. R. (1993). Disulfide Structures of Highly Bridged Peptides: A New Strategy for Analysis. *Protein Science* 2:1732–1748.

Greenamyre, J. T. and O'Brien, C. F. (1991). N-methyl-D-aspartate antagonists in the treatment of Parkinson's disease. *Arch. Neurol.* 48:977–981.

Gutstein, H. B. and Trujillo, K. A. (1993). MK-801 inhibits the development of morphine tolerance at spinal sites. *Brain Res.* 626:332–334.

Haack, J. A. et al. (1990). Conantokin-T: a gamma-carboxyglutamate containing peptide with N-methyl-d-aspartate antagonist activity. *J. Biol. Chem.* 265:6025–6029.

Harris, E. W. et al. (1984). Long-term potentiation in the hippocampus involves activation of N-methyl-D-aspartate receptors. *Brain Res.* 323:132–137.

Heyes, M. P., et al. (1989). Cerebrospinal fluid quinolinic acid concentrations are increased in acquired immune deficiency syndrome. *Ann. Neurol.* 26: 275–277.

Horiki, K. et al. (1978). *Chemistry Letters* 165–68.

Johnson, J. W. and Ascher, P. (1987). Glycine potentiates the NMDA response in cultured mouse brain neurons. *Nature* 325:529–531.

Johnson et al. (1990). *Ann. Rev. Pharmacol. Toxicol.* 30:707–750.

Kaiser et al. (1970). *Anal. Biochem.* 34:595.

Kapoor (1970). *J. Pharm. Sci.* 59:1–27.

Kest, B. et al. (1993). The NMDA receptor antagonist MK-801 protects against the development of morphine tolerance after intrathecal administration. *Proc. West Pharmacol. Soc.* 36:307–310.

Kleckner, N. W. and Dingledine, R. D. (1988). Requirement for glycine inactivation of NMDA receptors expressed in Xenopus oocytes. *Science* 241:835–837.

Klockgether, T. et al. (1990). NMDS antagonists potentiate antiparkinsonian actions of L-dopa in monoamine-depleted rats. *Ann. Neurol.* 28:539–546.

Kornreich, W. D. et al. (1986). U.S. Pat. No. 4,569,967.

Lipton, S. A. (1996). Similarity of neuronal cell injury and death in AIDS dementia and focal cerebral ischemia: potential treatment with NMDA open-channel blockers and nitric oxide-related species. *Brain Pathol* 6:507–517.

Lipton, S. A. (1994). Neuronal injury associated with HIV-1 and potential treatment with calcium-channel and NMDA antagonists. *Dav Neurosci.* 61:145–151.

Liu, H. et al. (1997). NMDA-receptor regulation of substance P release from primary afferent nociceptors. *Nature* 386:721–724.

Lutfy, K. et al. (1995). Blockade of morphine tolerance by ACEA-1328, a novel NMDA receptor/glycine site antagonist. *Eur. J. Pharmacol.* 273:187–189.

Lutfy, K. et al. (1996). Inhibition of morphine tolerance by NMDA receptor antagonists in the formalin test. *Brain Res.* 731:171–181.

Malmberg, A. B. and Taksh, T. L. (1995). The effect of morphine on formalin-evoked behavior and spinal release of excitatory amino acids and prostaglandin E2 using microdialysis in conscious rats. *Br. J. Pharmacol.* 114:1069–1075.

Malmberg, A. B. and Taksh, T. L. (1992). Hyperalgesia mediated by spinal glutamate or substance-P receptor blocked by spinal cyclooxygenase inhibition. *Science* 257:1276–1279.

Mao, J. et al. (1995). Experimental mononeuropathy reduces the antinociceptive effects of morphine: implications for common intracellular mechanisms involved in morphine tolerance and neuropathic pain. *Pain* 61:353–364.

Mao, J. et al. (1994). Thermal hyperalgesia in association with the development of morphine tolerance in rats: roles of excitatory amino acid receptors and protein kinase C. *J Neurosci.* 14:2301–2312.

Mayer, M. L. et al. (1987). Agonist- and voltage-gated calcium entry in cultured mouse spinal cord neurons under voltage clamp measured using arsenazo III. *J. Neurosci.* 7:3230–3244.

Mena, E. E. et al. (1990). Conantokin-G: a novel peptide antagonist to the N-methyl-D-aspartic acid (NMDA) receptor. *Neurosci. Lett.* 118:241–244.

McNamara, J. O. et al. (1988). Anticonvulsant and antiepileptogenic action of MK-801 in the kindling and electroshock models. *Neuropharmacology* 27:563–568.

*The Merck Manual of Diagnosis and Therapy,* 16 Ed., Berkow, R. et al., eds., Merck Research Laboratories, Rahway, N.J., pp. 1436–1445 (1992).

*Methoden der Organischen Chemie (Houben-Weyl): Synthese von Peptiden,* E. Wunsch (Ed.), Georg Thieme Verlag, Stuttgart, Ger. (1974).

Millian, M. J. and Seguin, L. (1994). Chemically-diverse ligands at the glycine B site coupled to N-methyl-D-asparatate (NMDA) receptors selectively block the late phase of formalin-induced pain in mice. *Neurosci. Lett.* 178:139–143.

Morris, R. G. M. et al. (1986). Selective impairment and blockade of long-term potentiation by an N-methyl-D-aspartate receptor antagonist, AP5. *Nature* 319:774–776.

Muller, W. E. et al. (1996). Neurotoxicity in rat cortical cells caused by N-methyl-D-aspartate (NMDA) and gp 120 of HIV-1: induction and pharmacological intervention. *Prog Mol Subcell Biol.* 16:44–57.

Nehlig, A. et al. (1990). Effects of phenobarbital in the developing rat brain. In *Neonatal Seizures,* Wasterlain, C. G. and Vertt, P. (eds.), Raven Press, New York, pp. 285–194.

Neugebauer, V. et al. (1993). N-methyl-D-aspartate (NMDA) and non-NMDA receptor antagonist block the hyperexcitability of dorsal horn neurons during development of acute arthritis in rat's kneejoint. *J Neurophysiol.* 70:1365–1377.

Nishida, K. et al. (1996). Increased brain levels of platelet-activating factor in a murine acquired immune deficiency syndrome are NMDA receptor-mediated. *J Neurochem* 66:433–435.

Nishiuchi, Y. et al. (1993). Synthesis of gamma-carboxyglutanic acid-containing peptides by the Boc strategy. *Int. J. Pept. Protein Res.* 42:533–538.

Nowak, L. et al. (1984). Magnesium gates glutamic-activated channels in mouse central neurons. *Nature* 307:462–465.

Olney, J. W. et al. (9187). Antiparkinsonian agents are phencyclidine agonists and N-methyl-D-aspartate antagonists. *Eur. J. Pharmacol.* 142:319–320.

Olivera, B. M. et al. (1984). U.S. Pat. No. 4,447,356.

Olivera, B. M. et al. (1985). Peptide neurotoxins from fish-hunting cone snails. *Science* 230:1338–1343.

Park, C. K. et al. (1988). The glutamate antagonist MK-801 reduces focal ischemia brain damage in the rat. *Ann. Neurol.* 24:543–551.

Popik, P. et al. (1995). 100 years of ibogaine: neurochemical and pharmacological actions of a putative anti-additive drug. *Pharmacol. Rev.* 47:235–253.

Raber, J. et al. (1996). Central nervous system expression of HIV-1 Gp 120 activates the hypothalamic-pituitary-adrenal axis: evidence for involvement of NMDA receptors and nitric oxide synthase. *Virology* 226:362–373.

Rall T. W. and Schleifer, L. S. in *Goodman and Gilman's The Pharmacological Basis of Therapeutics,* Seventh Ed., Gilman, A. G. et al., eds., Macmillan Publishing Co., New York, pp. 446–472 (1985).

Reynolds, I. J. et al. (1987). $^3$H-Labeled MK-801 binding to excitatory amino acid receptor complex from rat brain is enhance by glycine. *Proc. Natl. Acad. Sci. USA* 84:7744–7748.

Rice, A. S. and McMahon, S. B. (1994). Pre-emptive intrathecal administration of an NMDA receptor antagonist (AP-5) prevents hyper-reflexia in a model of persistent visceral pain. *Pain* 57:335–340.

Rivier, J. R. et al. (1978). *Biopolymers* 17:1927–38.

Rivier, J. R. et al. (1987). *Biochemistry,* 26:8508–8512.

Rivier, J. R. et al. (1987). Total synthesis and further characterization of the gamma-carboxyglutamate-containing 'sleeper' peptide from *Conus geographus.* *Biochem.* 26:8508–8512.

Roberts et al. (1983). *The Peptides* 5:342–429.

Rytik, P. G. et al. (1991). Susceptibility of primary human glial fibrillary acidic protein-positive brain cells to human immunodeficiency virus infection in vitro. Anti-HIV activity of memantine. *AIDS Res Hum Retrovir* 7:89–95.

Sambrook, J. et al. (1979). *Molecular Cloning: A Laboratory Manual,* 2nd Ed., Cold Spring Harbor Laboratory, Cold Spring Harbor, N.Y.

Schroder & Lubke (1965). *The Peptides* 1:72–75, Academic Press, NY.

Sei, Y. et al. (1996). Quinolinic acid levels in an murine retrovirus-induced immunodeficiency syndrome. *J Neurochem.* 66:296–302.

Shimoyama, N. et al. (1996). Ketamine attenuates and reverses morphine tolerance in rodents. *Anesthesiology* 85:1357–1366.

Simon, R. P. et al. (1984). Blockade of N-methyl-D-aspartate receptors may protect against ischemic damage in the brain. *Science* 226:850–852.

Skolnick, P. et al. (1992). Noncompetitive Inhibition of N-Methyl-D-Aspartate by Conantokin-G: Evidence for an Allosteric Interaction at Polyamines Sites. *J. Neurochem.* 59:1526–1521.

Sluka, K. A. and Westland, K. N. (1992). An experimental arthritis in rats: dorsal horn aspartate and glutamate increases. *Neurosci. Lett.* 145:141–144.

Spanagel, R. and Zieglgansberger, W. (1997). Anti-craving compounds for ethanol: new pharmacological tools to study addictive processes. *Trends Pharmacol. Sci.* 18:54–59.

Standaert, D. C. et al. (1994). Organization of N-methyl-D-aspartate glutamate receptor gene expression in the basal ganglia of the rat. *J. Comp. Neurol.* 343:1–16.

Sweetman, P. M. (1993). The envelope glycoprotein of HIV-1 alters NMDA receptor function. *Eur. J. Neurosci.* 5:276–283.

Starr, M. S. (1995). Antiparkinsonian actions of glutamate antagonists—alone and with L-Dopa: A review of evidence and suggestions for possible mechanisms. *J. Neural Tans.[P-D Sect]* 10:141–185.

Stewart and Young, *Solid-Phase Peptide Synthesis,* Freeman & Co., San Francisco, Calif. (1969).

Thompson, S. W. N. et al. (1990). Activity-dependent changes in rat ventral horn neurones in vitro; summation of prolonged afferent evoked postsynaptic depolarizations produce a d-APV sensitive windup. *Eur. J Neurosci.* 2:638–649.

Tiseo, P. J. et al. (1994). Modulation of morphine tolerance by the competitive N-methyl-D-aspartate receptor antagonist LY274614: assessment of opioid receptor changes. *J. Pharmacol. Exp. Ther.* 268:195–201.

Tiseo, P. J. and Inturrisi, C. E. (1993). Attenuation and reversal of morphine tolerance by the competitive N-methyl-D-Aspartate receptor antagonist, LY274614. *J Pharmacol Exp. Ther.* 264:1090–1096.

Troupin, A. S. et al. (1986). MK-801. In *New Anticonvulsant Drugs, Current Problems in Epilepsy* 4, Meldrum, B. S. and Porter, R. J. (eds.), John Libbey, London, pp. 191–202.

Trujillo, K. A. and Akil, H. (1994). Inhibition of opiate tolerance by non-competitive N-methyl-D-aspartate receptor antagonists. *Brain Res.* 633:178–188.

Trujillo, K. A. and Akil, H. Excitatory acids and drugs of abuse: a role for N-methyl-D-aspartate receptors in drug tolerance, sensitization and physical dependence. *Drug Alcohol Depend.* 38:139–154.

Ungerstedt, U. et al. (1973). Animal Models of Parkinsonism. In *Advances in Neurology: Progress in the Treatment of Parkinsonism,* Calne, D. B., Ed., Raven Press, New York, pp 257–271.

Vale et al. (1978). U.S. Pat. No. 4,105,603.

White, H. S., et al. (1992). Anticonvulsant profile of MDL 27,266: an orally active, broad-spectrum anticonvulsant agent. *Epilepsy Res.* 12:217–226.

White, H. S., et al. (1995). Experimental Selection, Quantification, and Evaluation of Antiepileptic Drugs. In *Antiepileptic Drugs,* 4th Ed., Levy, R. H., eds., Raven Press, N.Y., pp. 99–110.

Williams, K. et al. (1991). Modulation of the NMDA receptor by polyamines (Minireview). *Life Sci.* 48:469–498.

Wong, C. S. et al. (1996). Effects of NMDA receptor antagonists on inhibition of morphine tolerance in rats: binding at mu-opioid receptors. *Eur. J Pharmacol* 297:27–33.

Wong, E. H. P. et al. (1986). The anticonvulsant MK-801 is a potent NMDA antagonist. *Proc. Natl. Acad. Sci. USA* 83:7104–7108.

Wroblewski, J. T. et al. (1989). Glycine and D-serine act a positive modulators of signal transduction at N-methyl-D-aspartate sensitive glutamate receptors in cultured cerebellar granule cells. *Neuropharmacology* 28:447452.

Yamamoto, T. and Yaksh, T. L. (1992). Comparison of the antinociceptive effects of pre- and posttreatment with intrathecal morphine and MK-801, an NMDA antagonist, on the formalin test in the rat. *Anesthesiology* 77:757–763.

Zhou L. M., et al. (1996). Synthetic Analogues of Conantokin-G: NMDA Antagonists Acting Through a Novel Polyamine-Coupled Site. *J. Neurochem.* 66:620–628.

Zigmond, M. J. et al. (1987). Parkinsonism: Insights from animal models utilizing neurotoxic agents. In *Animal Models of Demential,* Coyle, J. T., Ed., Alan R. Liss, Inc., pp 1–38.

U.S. Pat. No. 3,972,859 (1976).
U.S. Pat. No. 3,842,067 (1974).
U.S. Pat. No. 3,862,925 (1975).
U.S. Pat. No. 5,550,050 (1996).
Published PCT Application WO 92/19195 (1992).
Published PCT Application WO 94/25503 (1994).
Published PCT Application WO 95/01203 (1995).
Published PCT Application WO 95/05452 (1995).
Published PCT Application WO 96/02286 (1996).
Published PCT Application WO 96/02646 (1996).
Published PCT Application WO 96/40871 (1996).
Published PCT Application WO 96/40959 (1996).
Published PCT Application WO 97/12635 (1997).

What is claimed is:

1. A substantially pure conantokin comprising a first, second, third and fourth domain, said first, second, third and fourth domains being contiguous, said first domain selected from the group consisting of GEγγ (SEQ ID NO:12), GDγγ (SEQ ID NO:27), GYγγ (SEQ ID NO:34), GAKγ (SEQ ID NO:40) and GNDV (SEQ ID NO:69), said second domain selected from the group consisting of LQγNQγ(SEQ ID NO:13), YQKMLγ (SEQ ID NO:15), VAKMAAγ (SEQ ID NO:18), LQANQA (SEQ ID NO:22), LQANQγ (SEQ ID NO:24), LQSNQγ (SEQ ID NO:25), LQTNQγ (SEQ ID NO:26), YSKFIγ (SEQ ID NO:28), YRKAMAγ (SEQ ID NO:31), DRγVAγ (SEQ ID NO: 35), DRγIAγ (SEQ ID NO:38), DRNNAγ (SEQ ID NO:41) and DRKLAγ (SEQ ID NO: 70), said third domain selected from the group consisting of NLRγ (SEQ ID NO:16), LARγ (SEQ ID NO:19), RERγ (SEQ ID NO:29), LEAKKAQγ (SEQ ID NO:32), TVRγ (SEQ ID NO:36), AVRγ (SEQ ID NO:42) and Lγγ, and said fourth domain selected from the group consisting of KSN, DAVN (SEQ ID NO:21), AGRLDLSKFP (SEQ ID NO:30), ALKA (SEQ ID NO:33), LDAA (SEQ ID NO:37), LEEA (SEQ ID NO:39), RLEEI (SEQ ID NO(:43) and LYγI (SEQ ID NO:71), and wherein each of said γ residues in said second domain, said third domain and said fourth domain may independently be substituted by Ala, Ser, Glu, Tyr or phospho-Ser (pSer).

2. The substantially pure conantokin of claim 1 selected from the group consisting of conantokin L having the amino acid sequence Gly-Glu-Xaa$_1$-Xaa$_1$-Val-Ala-Lys-Met-Ala-Ala-Xaa$_2$-Leu-Ala-Arg-Xaa$_2$-Asp-Ala-Val-Asn (SEQ ID NO:3), conantokin S1 having the amino acid sequence Gly-Asp-Xaa$_1$-Xaa$_1$-Tyr-Ser-Lys-Phe-Ile-Xaa$_2$-Arg-Glu-Arg-Xaa$_2$-Ala-Gly-Arg-Leu-Asp-Leu-Ser-Lys-Phe-Pro (SEQ ID NO:5), conantokin Oc having the amino acid sequence, Gly-Glu-Xaa$_1$-Xaa$_1$-Tyr-Arg-Lys-Ala-Met-Ala-Xaa$_2$-Leu-Glu-Ala-Lys-Lys-Ala-Gln-Xaa$_2$-Ala-Leu-Lys-Ala (SEQ ID NO:6), conantokin Gm having the amino acid sequence Gly-Ala-Lys-Xaa$_1$-Asp-Arg-Asn-Asn-Ala-Xaa$_1$-Ala-Val-Arg-Xaa$_2$-Arg-Leu-Glu-Glu-Ile (SEQ ID NO:7), conantokin Ca2 having the amino acid sequence Gly-Tyr-Xaa$_1$-Xaa$_1$-Asp-Arg-Xaa$_2$-Ile-Ala-Xaa$_2$-Thr-Val-Arg-Xaa$_2$-Leu-Glu-Glu-Ala (SEQ ID NO:8), conantokin Qu having the amino acid sequence Gly-Tyr-Xaa$_1$-Xaa$_1$-Asp-Arg-Xaa$_2$-Val-Ala-Xaa$_2$-Thr-Val-Arg-Xaa$_2$-Leu-Asp-Ala-Ala (SEQ ID NO:9), and conantokin Ca1 (Con Ca1) having the amino acid sequence Gly-Asn-Asp-Val-Asp-Arg-Lys-Leu-Ala-Xaa$_2$-Leu-Xaa$_2$-Xaa$_2$-Leu-Tyr-Xaa$_2$-Ile (SEQ ID NO:68), wherein Xaa$_1$ and Xaa$_2$ are γ-carboxyglutamic acid.

3. The substantially pure conantokin of claim 2, wherein said conantokin is modified by deleting one to five of the C-terminal amino acid residues.

4. The sustantially pure conantokin of claim 2 having the amino acid sequence Gly-Asp-Xaa$_1$-Xaa$_1$-Tyr-Ser-Lys-Phe-Ile-Xaa$_2$-Arg-Glu-Arg-Xaa$_2$-Ala-Gly-Arg-Leu-Asp-Leu-Ser-Lys-Phe-Pro (SEQ ID NO:5).

5. The sustantially pure conantokin of claim 1 having the amino acid sequence Gly-Glu-Xaa$_1$-Xaa$_1$-Tyr-Arg-Lys-Ala-Met-Ala-Xaa$_2$-Leu-Glu-Ala-Lys-Lys-Ala-Gln-Xaa$_2$-Ala-Leu-Lys-Ala (SEQ ID NO:6).

6. The sustantially pure conantokin of claim 1 having the amino acid sequence Gly-Glu-Xaa$_1$-Xaa$_1$-Val-Ala-Lys-Met-Ala-Ala-Xaa$_2$-Leu-Ala-Arg-Xaa$_2$-Asp-Ala-Val-Asn (SEQ ID NO:3).

7. The sustantially pure conantokin of claim 2 having the amino acid sequence Gly-Ala-Lys-Xaa$_1$-Asp-Arg-Asn-Asn-Ala-Xaa$_2$-Ala-Val-Arg-Xaa$_2$-Arg-Leu-Glu-Glu-Ile (SEQ ID NO:7).

8. The sustantially pure conantokin of claim 2 having the amino acid sequence Gly-Tyr-Xaa$_1$-Xaa$_1$-Asp-Arg-Xaa$_2$-Ile-Ala-Xaa$_2$-Thr-Val-Arg-Xaa$_2$-Leu-Glu-Glu-Ala (SEQ ID NO:8).

9. The sustantially pure conantokin of claim 1 having the amino acid sequence Gly-Tyr-Xaa$_1$-Xaa$_1$-Asp-Arg-Xaa$_2$-Val-Ala-Xaa$_2$-Thr-Val-Arg-Xaa$_2$-Leu-Asp-Ala-Ala (SEQ ID NO:9).

10. The substanially pure conantokin of claim 1 having the amino acid sequence Gly-Asn-Asp-Val-Asp-Arg-Lys-Leu-Ala-Xaa$_2$-Leu-Xaa$_2$-Xaa$_2$-Leu-Tyr-Xaa$_2$-Ile (SEQ ID NO:68).

11. The substantially pure conantokin of claim 1 selected from the group consisting of conantokin L having the amino acid sequence Gly-Glu-Xaa$_1$-Xaa$_1$-Val-Ala-Lys-Met-Ala-Ala-Xaa$_2$-Leu-Ala-Arg-Xaa$_2$-Asp-Ala-Val-Asn (SEQ ID NO:3), conantokin S1 having the amino acid sequence Gly-Asp-Xaa$_1$-Xaa$_1$-Tyr-Ser-Lys-Phe-Ile-Xaa$_1$-Arg-Glu-Arg-Xaa$_2$-Ala-Gly-Arg-Leu-Asp-Leu-Ser-Lys-Phe-Pro (SEQ ID NO:5), conantokin Oc having the amino acid sequence Gly-Glu-Xaa$_1$-Xaa$_1$-Tyr-Arg-Lys-Ala-Met-Ala-Xaa$_2$-Leu-Glu-Ala-Lys-Lys-Ala-Gln-Xaa$_1$-Ala-Leu-Lys-Ala (SEQ ID NO:6), conantokin Gm having the amino acid sequence Gly-Ala-Lys-Xaa$_1$-Asp-Arg-Asn-Asn-Ala-Xaa$_2$-Ala-Val-Arg-Xaa$_2$-Arg-Leu-Glu-Glu-Ile (SEQ ID NO:7), conantokin Ca2 having the amino acid sequence Gly-Tyr-Xaa$_1$-Xaa$_1$-Asp-Arg-Xaa$_2$-Ile-Ala-Xaa$_2$-Thr-Val-Arg-Xaa$_2$-Leu-Glu-Glu-Ala (SEQ ID NO:8), conantokin Qu having the amino acid sequence Gly-Tyr-Xaa$_1$-Xaa$_1$-Asp-Arg-Xaa$_2$-Val-Ala-Xaa$_2$-Thr-Val-Arg-Xaa$_2$-Leu-Asp-Ala-Ala (SEQ ID NO:9), and conantokin Ca1 (Con Ca1) having the amino acid sequence Gly-Asn-Asp-Val-Asp-Arg-Lys-Leu-Ala-Xaa$_2$-Leu-Xaa$_2$-Xaa$_2$-Leu-Tyr-Xaa$_2$-Ile (SEQ ID NO:68), wherein Xaa$_1$ is γ-carboxyglutamic acid and Xaa$_2$ is selected from the group consisting of Ser, Ala, Glu, Tyr and phospho-Ser (pSer).

12. The substantially pure conantokin of claim 11, wherein said conantokin is modified by deleting one to five of the C-terminal amino acid residues.

13. The substantially pure conantokin of claim 11, wherein said conantokin is modified by deleting one to five of the C-terminal amino acid residues.

14. A substantially pure conantokin selected from the group consisting of conantokin T having the amino acid sequence Gly-Glu-Xaa$_1$-Xaa$_1$-Tyr-Gln-Lys-Met-Leu-Xaa$_2$-Asn-Leu-Arg-Xaa$_2$-Ala-Glu-Val-Lys-Lys-Asn-Ala (SEQ ID NO:2) and conantokin R having the amino acid sequence Gly-Glu-Xaa$_1$-Xaa$_1$-Val-Ala-Lys-Met-Ala-Ala-Xaa$_2$-Leu-Ala-Arg-Xaa$_2$-Asn-Ile-Ala-Lys-Gly-Cys-Lys-Val-Asn-Cys-Tyr-Pro (SEQ ID NO:4), wherein Xaa$_1$ is γ-carboxyglutamic acid and Xaa$_2$ is selected from the group consisting of Ser, Ala, Glu, Tyr and phospho-Ser (pSer).

15. The substantially pure conantokin of claim 14, wherein said conantokin is modified by deleting one to five of the C-terminal amino acid residues.

16. A substantially pure conantokin comprising a first, second, third and fourth domain, said first, second, third and fourth domains being contiguous, said first domain selected from the group consisting of GEγγ (SEQ ID NO:12), GDγγ (SEQ ID NO:27), GYγγ (SEQ ID NO:34), GAKγ (SEQ ID NO:40) and GNDV (SEQ ID NO:69), said second domain selected from the group consisting of LQγNQγ (SEQ ID NO:13), YQKMLγ (SEQ ID NO:15), VAKMAAγ (SEQ ID NO:18), LQANQA (SEQ ID NO:22), LQANQγ (SEQ ID NO:24), LQSNQγ (SEQ ID NO:25), LQTNQγ (SEQ ID NO:26), YSKFIγ (SEQ ID NO:28), YRKAMAγ (SEQ ID NO:31), DRγVAγ (SEQ ID NO:35), DRγIAγ (SEQ ID NO:38), DRNNAγ (SEQ ID NO:41) and DRKLAγ (SEQ ID NO: 70), said third domain is LIRγ (SEQ ID NO:14), and said fourth domain selected from the group consisting of AEVKKNA (SEQ ID NO:17), NIAKGCKVNCYP (SEQ ID NO:20), DAVN (SEQ ID NO:21), AGRLDLSKFP (SEQ ID NO:30), ALKA (SEQ ID NO:33), LDAA (SEQ ID NO:37), LEEA (SEQ ID NO:39), RLEEI (SEQ ID NO:43) and LYγI (SEQ ID NO:71), and wherein each of said γ residues in said second domain, said third domain and said fourth domain may independently be substituted by Ala, Ser, Glu, Tyr or phospho-Ser (pSer).

17. The substantially pure conantokin of claim 16, wherein said conantokin is modified by deleting one to five of the C-terminal amino acid residues.

\* \* \* \* \*